(12) United States Patent
Kopetzki et al.

(10) Patent No.: US 9,802,952 B2
(45) Date of Patent: Oct. 31, 2017

(54) METHOD AND APPARATUS FOR THE SYNTHESIS OF DIHYDROARTEMISININ AND ARTEMISININ DERIVATIVES

(71) Applicant: MAX-PLANCK-GESELLSCHAFT ZUR FÖRDERUNG DER WISSENSCHAFTEN E.V., Munich (DE)

(72) Inventors: Daniel Kopetzki, Berlin (DE); David Tyler McQuade, Tallahassee, FL (US); Peter H. Seeberger, Kleinmachnow (DE); Kerry Gilmore, Brewster, MA (US)

(73) Assignee: Max-Plank-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/904,671

(22) PCT Filed: Jul. 14, 2014

(86) PCT No.: PCT/EP2014/065053
§ 371 (c)(1),
(2) Date: Jan. 12, 2016

(87) PCT Pub. No.: WO2015/007693
PCT Pub. Date: Jan. 22, 2015

(65) Prior Publication Data
US 2016/0145265 A1    May 26, 2016

(30) Foreign Application Priority Data
Jul. 15, 2013 (EP) .................................... 13176539

(51) Int. Cl.
C07D 493/18    (2006.01)
B01J 19/24    (2006.01)

(52) U.S. Cl.
CPC .......... *C07D 493/18* (2013.01); *B01J 19/245* (2013.01); *B01J 2219/24* (2013.01)

(58) Field of Classification Search
CPC .................................................. C07D 493/18
See application file for complete search history.

(56) References Cited

U.S. PATENT DOCUMENTS 6,750,356 B1    6/2004    Bhakuni et al.

FOREIGN PATENT DOCUMENTS

| WO | WO 2008/087666 A1 | 7/2008 |
| WO | WO 2008/087667 A1 | 7/2008 |
| WO | WO 2013/030247 A1 | 3/2013 |
| WO | WO 2013/038206 A1 | 3/2013 |

OTHER PUBLICATIONS

"Alkali Metals." © 2017. Available at: < https://www.hobart.k12.in.us/ksms/PeriodicTable/alkalimetals.htm >.*
Gray, R. "Examples of Salts in Chemistry." © 2017. Available from: <http://education.seattlepi.com/examples-salts-chemistry-1381.html>.*
"List of Metals." © 2017. Available at: < http://sciencenotes.org/list-metals/>.*
"Alkaline Earth Metals." © 2017. Available at: < https://www.hobart.k12.in.us/ksms/PeriodicTable/alkalineearthmetals.htm >.*
Brown et al., "Convenient Procedure for the Conversion of Sodium Borohydride into Lithium Borohydride in Simple Ether Solvents" *Inorg. Chem.* (1981) 20:4454-4456.
Wallaart, et al., "Isolation and Identification of Dihydroartemisinic Acid from *Artemesia annua* and Its Possible Role in the Biosynthesis of Artemisinin" *J. Nat. Prod.* (1999) 62:430-433.
World Malaria Report 2010, WHO Geneva, 2010.
International Search Report and Written Opinion dated Sep. 11, 2014 for PCT Application No. PCT/EP2014/065053, filed Jul. 14, 2014.

* cited by examiner

*Primary Examiner* — Noble Jarrell
*Assistant Examiner* — John S Kenyon
(74) *Attorney, Agent, or Firm* — Knobbe, Martens, Olson & Bear, LLP

(57) ABSTRACT

The present invention is directed to a method for continuous production of dihydroartemisinin and also artemisinin derivatives derived from dihydroartemisinin by using artemisinin or dihydroartemisinic acid (DHAA) as starting material as well as to a continuous flow reactor for producing dihydroartemisinin as well as the artemisinin derivatives. It was found that the reduction of artemisinin to dihydroartemisinin in a continuous process requires a special kind of reactor and a special combination of reagents comprising a hydride reducing agent, at least one activator such as an inorganic activator, at least one solid base, at least one aprotic solvent and at least one $C_1$-$C_5$ alcohol.

19 Claims, 10 Drawing Sheets

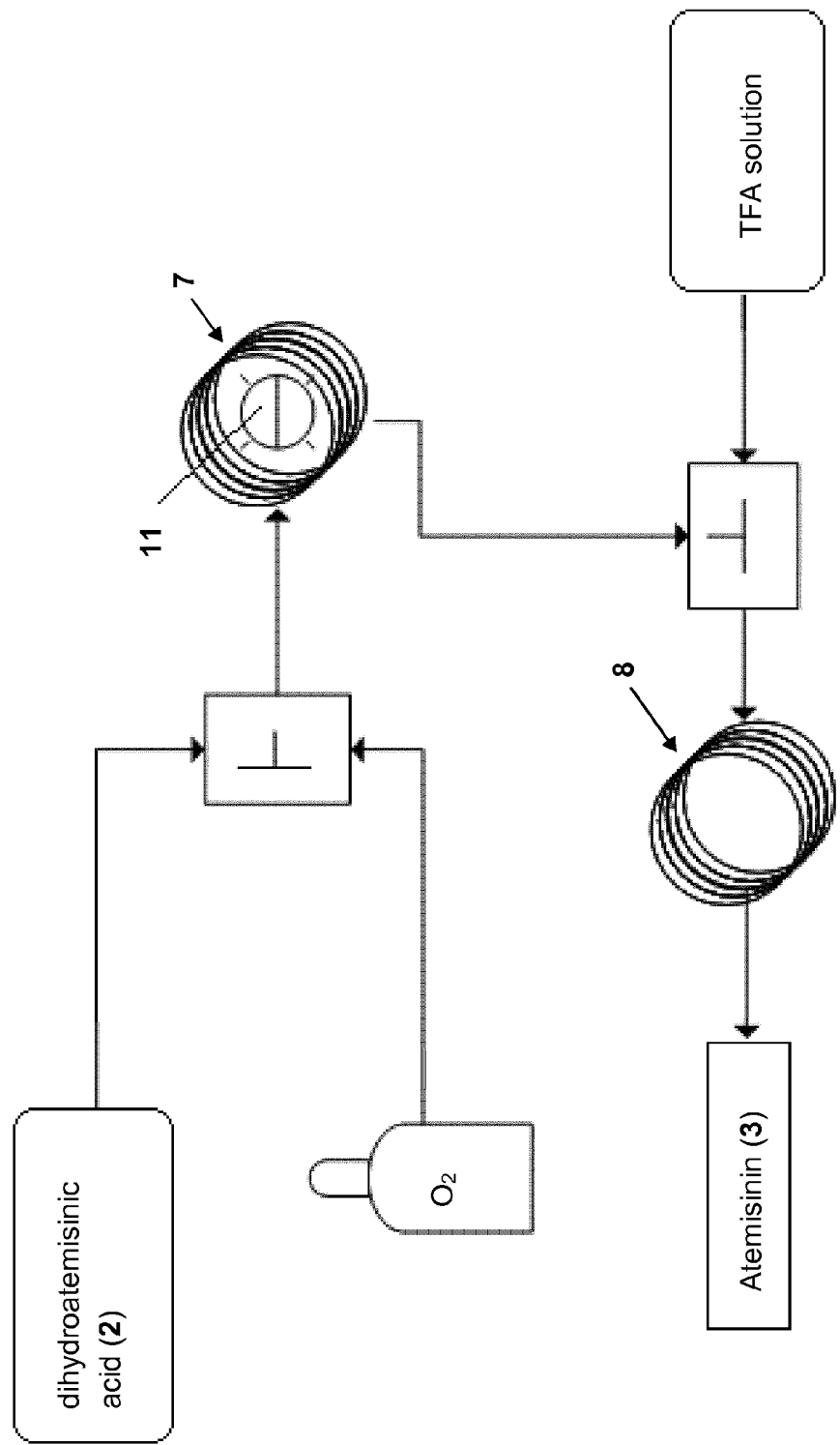

Figure 2

METHOD AND APPARATUS FOR THE SYNTHESIS OF DIHYDROARTEMISININ AND ARTEMISININ DERIVATIVES

The present invention is directed to a method for continuous production of dihydroartemisinin and also artemisinin derivatives derived from dihydroartemisinin by using artemisinin or dihydroartemisinic acid (DHAA) as starting material as well as to a continuous flow reactor for producing dihydroartemisinin as well as the artemisinin derivatives. It was found that the reduction of artemisinin to dihydroartemisinin in a continuous process requires a special kind of reactor and a special combination of reagents as disclosed herein in detail.

BACKGROUND OF THE INVENTION

Malaria, caused by the protozoan parasite *Plasmodium falciparum*, remains a major global health problem that kills almost one million people each year. Artemisinin and its derivatives are currently the most effective treatment against multi-drug resistant *Plasmodium* species and artemisinin combination treatments (ACTs) are now first-line drugs (World Malaria Report 2010, WHO Geneva, 2010). Artemisinin belongs to the group of sesquiterpenes and has an uncommon trioxane ring structure and a peroxide bridge.

Artemisinin has a poor bioavailability. Therefore, artemisinin derivatives such as artemether, arteether, artelinic acid and artesunate have been developed. Dihydroartemisinin (DHA or arteminol) is also used as an antimalarial drug. Dihydroartemisinin is available as a fixed drug combination with piperaquine. Artemether, arteether (Artemotil) and artelinic acid are ether derivatives of artemisinin. Artemether and arteether have more potential as compared to artemisinin and are ideal antimalarial drugs, especially for treating multi drug resistant and complicated strains of *Plasmodium falciparum*.

Artesunate is an ester derivative of artemisinin that is water-soluble and may therefore be given by injection. According to WHO intravenous artesunate is the drug of choice for severe malaria both in children and adults where there is low transmission.

Artesunate is hydrolyzed within minutes to its active metabolite, dihydroartemisinin, which is considered to be responsible for the antimalarial activity. In vitro data provide evidence for CYP2A6 as the major metabolizing enzyme for artesunate. Artemether is rapidly demethylated to the active metabolite dihydroartemisinin (DHA) by CYP3A4 and CYP3A5.

In vitro studies using human recombinant cytochrome P450 enzymes showed that primarily CYP3A4 is involved in the metabolism of arteether to its active metabolite, dihydroartemisinin (DHA).

Some synthetic methods of ether derivatives of artemisinin are known. U.S. Pat. No. 6,750,356 discloses a single pot conversion of artemisinin to arteether. Artemisinin is reduced to dihydroartemisinin by sodium borohydride in presence of polyhydroxy catalyst and conversion to arteether is carried out in presence of acid catalyst. But this method is time consuming and tedious as it involves purification step by column chromatography.

WO 2008087666 A1 discloses another synthetic method for synthesis of the ether derivative of artemisinin. In this method, artemisinin is reduced to dihydroartemisinin by a mixture of sodium borohydride and a dihydroxy compound. Etherification is carried out in presence of an acid catalyst and an alcohol. After isolating the alpha and beta compounds, recrystallization is to be performed in a hydroalcoholic solution to obtain pure beta ether compound.

WO 2008087667 A1 discloses a method for synthesis of artesunate from artemisinin in one-pot. This method comprises reducing artemisinin to dihydroartemisinin with a mixture of sodium borohydride and a dihydroxy compound; esterifying dihydroartemisinin in the presence of succinic anhydride and imidazole or its derivative as a catalyst in an aprotic solvent and isolating the artesunate by crystallization.

Intending to utilize continuous flow chemistry as a means to scale-up photochemical transformations the inventors examined the transformation of artemisinic acid (1) or dihydroartemisinic acid (2) to artemisinin (3) mindful of the necessity to create a simple, scalable and inexpensive process.

The above-mentioned conversion reactions in the state of art from artemisinin to artemisinin derivatives are performed with batch methods. As already mentioned, batch method has disadvantages such as scale-up, high cost and elaborate purification steps. Most of all in the state of the prior art, for producing each of artemisinin derivative, respective batch procedure and corresponding batch equipment are necessary.

In the state of the art so far only batch methods are known for the synthesis of ester and ether derivatives of artemisinin. However it has been found that the reduction of artemisinin to dihydroartemisinin and further conversion of the dihydroartemisinin to ether or ester derivatives is quite problematic when a certain scale is reached.

Thus objective of the present invention is to provide a more efficient method for the reduction of artemisinin as well as for the synthesis of artemisinin derivatives. The objective of the present invention is solved by the teaching of the independent claims. Further advantageous features, aspects and details of the invention are evident from the dependent claims, the description, the figures, and the examples of the present application.

DESCRIPTION OF THE INVENTION

It was found that the reduction of artemisinin and the preparation of artemisinin derivatives can be readily scaled up by the means of a continuous process using a column containing a hydride reducing agent, at least one activator and especially at least one inorganic activator and at least one solid base or by using a combination of two columns wherein the first column contains at least one solid base and the second column contains a hydride reducing agent and at least one activator.

Thus, the present invention is directed to a method for reducing artemisinin in a continuous manner or in other words the present invention is directed to a continuous method for reducing artemisinin comprising the following steps:

1) providing a column containing a hydride reducing agent, at least one activator and at least one solid base or providing a first column containing at least one solid base and a second column containing a hydride reducing agent and at least one activator,
2) providing a continuous flow of a solution of artemisinin in at least one aprotic solvent containing at least one $C_1$-$C_5$ alcohol through the column containing the hydride reducing agent, the at least one activator and the at least one solid base or through the first column containing the at least one solid base and the second column containing the hydride reducing agent and the at least one activator,
3) thereby reducing artemisinin in a continuous manner to dihydroartemisinin of the following formula

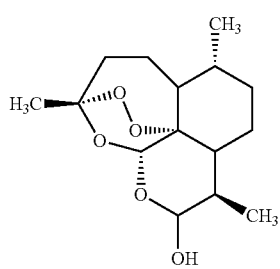

Since the embodiment using one single column instead of two columns is preferred, the present invention is directed to a method for continuously reducing Artemisinin comprising the following steps:
1) providing a column containing a hydride reducing agent, at least one activator and at least one solid base,
2) providing a continuous flow of a solution of artemisinin in at least one aprotic solvent containing at least one $C_1$-$C_5$ alcohol through the column containing the hydride reducing agent, the at least one activator and the at least one solid base,
3) thereby reducing artemisinin in a continuous manner to dihydroartemisinin of the following formula

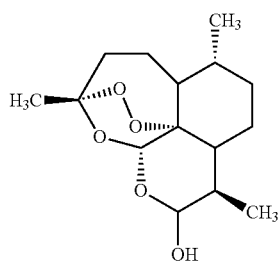

Since the activator is preferably an inorganic activator, the present invention is directed to the following continuous method for reducing artemisinin comprising the following steps:
1) providing a column containing a hydride reducing agent, at least one inorganic activator and at least one solid base or providing a first column containing at least one solid base and a second column containing a hydride reducing agent and at least one inorganic activator,
2) providing a continuous flow of a solution of artemisinin in at least one aprotic solvent containing at least one $C_1$-$C_5$ alcohol through the column containing the hydride reducing agent, the at least one inorganic activator and the at least one solid base or through the first column containing the at least one solid base and the second column containing the hydride reducing agent and the at least one inorganic activator,
3) thereby reducing artemisinin in a continuous manner to dihydroartemisinin of the following formula

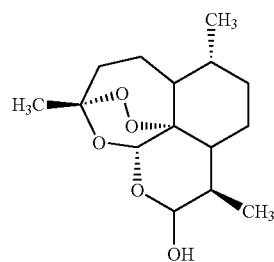

Since the embodiment using one single column instead of two columns is preferred, the present invention is directed to a method for continuously reducing Artemisinin comprising the following steps:
1) providing a column containing a hydride reducing agent, at least one inorganic activator and at least one solid base,
2) providing a continuous flow of a solution of artemisinin in at least one aprotic solvent containing at least one $C_1$-$C_5$ alcohol through the column containing the hydride reducing agent, the at least one inorganic activator and the at least one solid base,
3) thereby reducing artemisinin in a continuous manner to dihydroartemisinin of the following formula

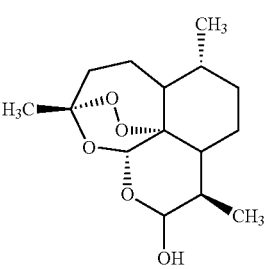

The artemisinin used in the present methods can be obtained from dihydroartemisinic acid in accordance to known procedures which are, for instance, disclosed in WO2013030247A1 which is an earlier application of the present inventors.

Thus the preparation of artemisinin from dihydroartemisinic acid can be performed before the reduction step of artemisinin to dihydroartemisinin. Consequently the present invention is also directed to an above-mentioned method for continuously reducing artemisinin further comprising the following steps A) and B) before step 1):
A) providing dihydroartemisinic acid represented by the following formula

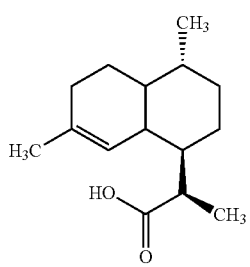

B) performing the following reactions
  i) photooxidation of dihydroartemisinic acid with singlet oxygen,
  ii) followed by an acid mediated cleavage, and
  iii) subsequent oxidation with triplet oxygen
  in order to obtain artemisinin of the following formula:

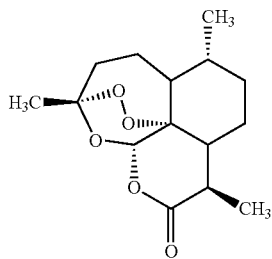
3

Moreover it is preferred that the obtained dihydroartemisinin is further converted to an artemisinin derivative (5) which is most preferably an ether or ester derivative. Accordingly the above-mentioned methods comprising the steps 1), 2) and 3) or A), B), 1), 2) and 3) preferably comprise the following step 4) after the step 3):
  4) converting the dihydroartemisinin obtained from step 3) to an artemisinin derivative of the following formula

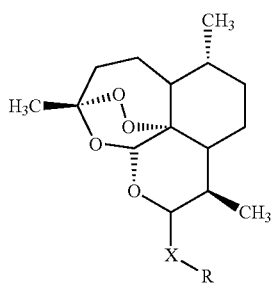
5 wherein X is O or S and
R is $—R^1$, $—COR^1$, $—CONHR^1$, $—CSNHR^1$, or $—SO_2R^1$; and
$R^1$ represents a $C_1$-$C_{10}$ alkyl, $C_1$-$C_{10}$ halogenalkyl, hydroxyalkyl, $C_2$-$C_{10}$ alkoxyalkyl, $C_2$-$C_{10}$ carboxyalkyl, $C_6$-$C_{14}$ aryl, $C_7$-$C_{16}$ alkylaryl, $C_7$-$C_{16}$ alkoxyaryl, $C_7$-$C_{16}$ arylalkyl, $C_8$-$C_{16}$ arylalkoxyalkyl, $C_8$-$C_{16}$ alkylarylalkyl, $C_8$-$C_{16}$ alkylarylalkoxyalkyl, $C_2$-$C_{10}$ alkenyl, $C_2$-$C_{10}$ alkynyl, $C_3$-$C_8$ cycloalkyl, $C_4$-$C_{10}$ alkylcycloalkyl, $C_4$-$C_{10}$ alkoxyalkylcycloalkyl, $C_4$-$C_{12}$ cycloalkylalkyl, $C_4$-$C_{16}$ cycloalkylalkoxyalkyl, $C_1$-$C_5$ heterocyclyl, $C_3$-$C_{10}$ alkoxycarbonylalkyl, $C_2$-$C_{10}$ acyloxyalkyl, $C_3$-$C_{12}$ heterocyclylalkyl, $C_3$-$C_{10}$ alkylcarbonylaminoalkyl, $C_3$-$C_{10}$ alkoxycarbonylaminoalkyl, $C_1$-$C_{10}$ aminoalkyl, $C_2$-$C_{10}$ alkylaminoalkyl, $C_3$-$C_{10}$ dialkylaminoalkyl, $C_3$-$C_{10}$ alkylaminocarbonylalkyl, or $C_4$-$C_{10}$ dialkylaminocarbonylalkyl.

At step 4) converting the dihydroartemisinin 4 obtained from step 3 to an artemisinin derivative of the formula (5) is performed by reacting the dihydroartemisinin 4 with an appropriate precursor compound as follows:
  if R is $—R^1$, then the precursor compound is $R^1$—X—H or $R^1$-$L_1$;
  if R is $—COR^1$ and $R^1$ is not $C_2$-$C_{10}$ carboxylalkyl, then the precursor compound is $R^1$—$CO_2H$, or $R^1$—CO—O—OC—$R^1$;
  if R is $—COR^1$ and $R^1$ is $C_2$-$C_{10}$ carboxylalkyl, then the precursor compound is $C_3$-$C_{11}$ cyclic anhydride of the formula

or $C_3$-$C_{11}$ alkyl carboxylic acid $C_1$-$C_4$ alkyl ester;
  if R is $—CONHR^1$, then the precursor compound is $R^1$—N=C=O;
  if R is $—CSNHR^1$, then the precursor compound is $R^1$—N=C=S;
  if R is $–SO_2R^1$, then the precursor compound is $R^1SO_3H$, $R^1SO_2$—O—$SO_2R^1$, or $R^1SO_2Cl$;
wherein $R^1$ has the same meaning as defined herein; and
$L_1$ is a leaving group selected from the following list consisting of —F, —Cl, —Br, —I, —$OSO_2Me$, —$OSO_3Me$, —$OSO_2CF_3$, —$OSO_2CF_2CF_3$, —$OSO_2$(p-Tol).

Optionally, the carboxylic acid (—$CO_2H$) of the precursors compounds "$R^1$—$CO_2H$" and "$C_3$-$C_{11}$ alkyl carboxylic acid $C_1$-$C_4$ alkyl ester" may be converted to an activated form (—CO-$A_1$) before used within step 4). A suitable activating group "$A_1$" is preferably selected from the following group consisting of —F, —Cl, —Br, —I,

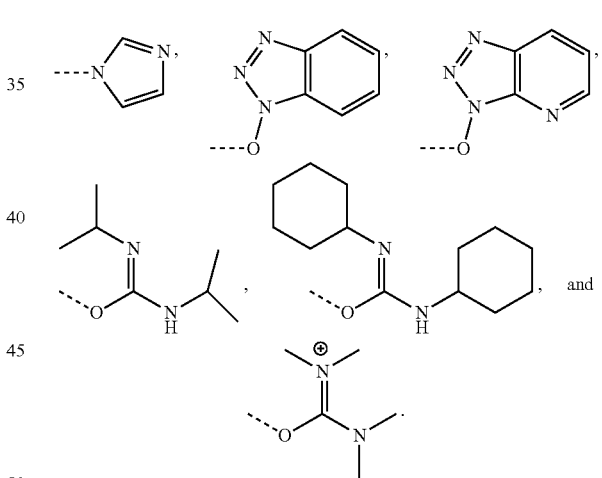

It is preferred that not only steps 1), 2) and 3) are performed in a continuous manner but also step 4). Consequently it is preferred that all steps 1) to 4) are performed in a continuous manner. Moreover the purification step of the artemisinin derivative (5) can be performed in a continuous manner. It is still more preferred if the steps A), B), 1), 2) and 3) are performed in a continuous manner and most preferred if steps A), B), 1), 2), 3) and 4) are performed in a continuous manner optionally together with a continuous purification step of the artemisinin derivative (5).

The term "continuous" as used herein means, for instance, that there is provided a flow of a solution or mixture containing the reaction components such as dihydroartemisinic acid (2) or artemisinin (3) to the reactor which is continuously converted while flowing through the reactor system in the direction from an inlet to an outlet such that a reaction product can be continuously derived at the outlet of the reactor without dividing the reaction mixture into parts. The term "continuous" or "continuously" in regard to the synthesis of artemisinin (3) can be defined as a movement of the solution or mixture containing dihydroartemisinic acid (2) through the photochemical reactor (7) while irradiated or while exposed to the light of the light source (11). This movement should only be in one direction, namely from the inlet to the outlet of the photochemical reactor (7) or in other words from the mixing device or from the reservoir containing the starting materials (e.g. containing the solution of dihydroartemisinic acid (2) and optionally also the photosensitizer) to the feed of the acidic solution or to the reactor (8). The movement could also temporarily stop (velocity of the movement is zero) during a part of the time of the photooxidation. Thus during the time of the photooxidation, there must be a movement for a certain time in the direction described above.

The term "continuous" or "continuously" in regard to the reduction of artemisinin (3) to dihydroartemisinin (4) can be defined as a movement of the solution or mixture containing artemisinin (3) through the column (9) or through the columns (10A and 10B) while the reduction takes place. This movement should only be in one direction, namely from the inlet to the outlet of the column (9) or from the inlet to the outlet of the column (10A) to the inlet of column (10B) and to the outlet of column (10B). The movement could also temporarily stop (velocity of the movement is zero) during a part of the time of the reduction reaction. Thus during the time of the reduction, there must be a movement for a certain time in the direction described above.

It is preferred that artemisinin (3) is converted in a continuous manner to the artemisinin derivatives (5). Thus, in regard to the artemisinin derivatives (5) the term "continuous" or "continuously" refers to a movement of the solution or mixture containing artemisinin (3) through the column (9) or through the columns (10A and 10B) wherein the reduction takes place to the reactor (12) for converting dihydroartemisinin (4) to the artemisinin derivatives (5). This movement should only be in one direction, namely from the inlet to the outlet of the column (9) and than to the inlet of reactor (12) or from the inlet to the outlet of the column (10A) to the inlet of column (10B) and to the outlet of column (10B) and than to the inlet of reactor (12). The movement could also temporarily stop (velocity of the movement is zero) during a part of the time of the reduction and/or derivatization reaction. Thus during the time of the reduction and/or derivatization reaction, there must be a movement for a certain time in the direction described above.

The term "continuous" or "continuously" in regard to the whole process of converting dihydroartemisinic acid (2) to an artemisinin derivative (5) can be defined as a movement of the solution or mixture containing dihydroartemisinic acid (2) through the continuous flow reactor (6) in order to obtain dihydroartemisinin (4) or preferably directly the artemisinin derivative (5). The movement could temporarily stop (velocity of the movement is zero) during a part of the time of the complete reaction sequence. However although the flow of the reaction mixture might temporarily stop, the reaction mixture is processed through the continuous flow reactor (6) in a manner that not parts of the reaction mixture are in between processed batch-wise. Thus there is a continuous flow through the continuous flow reactor (6) which might be processed with different velocities and might also stop but is not divided into single batches which are processed separately and later on probably combined again. Thus if the continuous flow is theoretically divided into subsequent volume units it is still a continuous flow as long as the order of these theoretical volume units is not altered.

Thus, the continuous flow as described herein may occur at a steady or a fluctuating flow rate. In case of a fluctuating flow the reaction mixture may also stop intermediately or periodically, hence the flow rate may fall down to zero. However, if once stopped the continuous flow has to continue in the direction from the inlet to the outlet of the respective reactor. "Continuous" as used herein also means that a desired product such as dihydroartemisinin (4) or the artemisinin derivative (5) can be provided steadily without the necessity of starting a novel experiment or batch in order to increase the amount of the desired product after the reaction took place. The reaction set-up and the reactor design allow a steadily increasing amount of product when starting material is provided without upscaling the reactor dimensions. "Continuous" further means that if a starting material is constantly provided and converted, the conversion compound is consistently produced.

Thus if the steps 1), 2) and 3) and optionally 4) are performed in a continuous, the term "continuous" refers to an endless flow of a solution or mixture containing artemisinin (3) through the column (9) or through the columns (10A) and (10B).

If the steps A), B), 1), 2) and 3) and optionally 4) are performed in a continuous, the term "continuous" refers to an endless flow of a solution or mixture containing dihydroartemisinic acid (2) through the continuous flow reactor (6).

Of course the flow through the column (9) or the columns (10A) and (10B) or the continuous flow reactor (6) is theoretically endless and in practice will end after a certain time when for example the light source has to be replaced, the oxygen tank is empty, the column containing the hydride reducing agent or the column containing the solid base or any part of the continuous flow reactor (6) has to be repaired or replaced or the reservoir of the dihydroartemisinic acid (2) starting material is empty.

Preferably the substituent R is derived from a succinic acid monoester, a primary alcohol, a secondary alcohol, a tertiary alcohol, an alkoxy alcohol, a carboxylic acid, an alkoxycarbonyl carboxylic acid, an acyloxy carboxylic acid, cyclic anhydride, succinic anhydride, or a carboxyalkylester.

The residue —XR is preferably an ether residue or an ester residue, wherein R is any group containing up to 10 carbon atoms which is bond through one of these carbon atoms to the oxygen (ether residue) or R is any acyl group containing 2, 3, 4, 5, 6, 7, 8, 9, 10, or 11 carbon atoms which is bond through the carbonyl group to the oxygen (ester residue). The group R may further contain up to 5 hetero atoms selected from O, N, S, F, Cl, Br, and I.

The term "$C_1$-$C_{10}$ alkyl" as used herein refers to a saturated linear or branched carbon chain consisting of 1 to 10 carbon atoms. Examples are —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$CH(CH_3)$—$C(CH_3)_3$, —$C_7H_{15}$, —$C_3H_6$—$C(CH_3)_3$, —$C_4H_8$—$CH(CH_3)_2$, —$C_8H_{17}$, —$C_4H_8$—$C(CH_3)_3$, —$C_5H_{10}$—$CH(CH_3)_2$, —$C_9H_{19}$, —$C_5H_{10}$—$C$ $(CH_3)_3$, $-C_6H_{12}-CH(CH_3)_2$, $-C_{10}H_{21}$, $-C_6H_{12}-C(CH_3)_3$ and $-C_7H_{14}-CH(CH_3)_2$.

The term "$-C_1-C_9$ alkyl-" as used herein refers to a saturated linear or branched carbon chain consisting of 1 to 9 carbon atoms. Examples are $-CH_2-$, $-C_2H_4-$, $-C_3H_6-$, $-C(CH_3)_2-$, $-C_4H_8-$, $-CH_2-C(CH_3)_2-$, $-CH(CH_3)-C_2H_4-$, $-C_5H_{10}-$, $-CH(CH_3)-C_3H_6-$, $-CH(CH_2CH_3)-C_2H_4-$, $-CH_2-CH(CH_3)-C_2H_4-$, $-CH_2-CH(CH_3)-CH(CH_3)-$, $-CH_2-CH(CH_3)_2-CH_2-$, $-C(CH_3)_2-C_2H_4-$, $-CH(CH_3)-C(CH_3)_2-$, $-C(C_2H_5)_2-$, $-C_6H_{12}-$, $-CH(CH_3)-C_4H_8-$, $-C_2H_4-CH(CH_3)-C_2H_4-$, $-CH_2-CH(CH_3)-C_3H_6-$, $-CH(CH_3)-CH(CH_3)-C_2H_4-$, $-CH(CH_3)-CH_2-CH(CH_3)-CH_2-$, $-CH(CH_3)-CH_2-CH_2-CH(CH_3)-$, $-CH(CH_3)-CH_2-C(CH_3)_2-$, $-C_3H_6-C(CH_3)_2-$, $-CH_2-CH(CH_3)-C(CH_3)_2-$, $-CH_2-C(CH_3)_2-C_2H_4-$, $-C(CH_3)_2-C(CH_3)_2-$, $-C_7H_{14}-$, $-C_3H_6-CH(CH_3)-C_2H_4-$, $-C_2H_4-C(CH_3)_2-C_2H_4-$, $-C_4H_8-C(CH_3)_2-$, $-C_8H_{16}-$, $-C_4H_8-C(CH_3)_3$, $-C_5H_{10}-C(CH_3)_2-$, and $-C_9H_{18}-$.

The term "$C_1-C_{10}$ halogenalkyl" as used herein refers to a saturated linear or branched $C_1-C_{10}$ alkyl group which contains at least one halogen atom. Examples are: $-CH_2F$, $-CHF_2$, $-CF_3$, $-CH_2Cl$, $-CH_2Br$, $-CH_2I$, $-CH_2-CH_2F$, $-CH_2-CHF_2$, $-CH_2-CF_3$, $-CH_2-CH_2Cl$, $-CH_2-CH_2Br$, $-CH_2-CH_2I$, and $-CH_2-CF_2-CF_3$.

The term "$C_1-C_{10}$ hydroxyalkyl" as used herein refers to a saturated linear or branched $C_1-C_{10}$ alkyl group substituted by at least one hydroxyl group. It is clear to a skilled person that the term "substituted" refers to the replacement of a hydrogen atom by one of the substituents. Examples are $-CH_2OH$, $-CH_2CH_2OH$, $-CH_2CH_2CH_2OH$, $-CH_2CH_2CH_2CH_2OH$, $-CH_2CH_2CH_2CH_2CH_2OH$, $-CH(CH_3)CH_2OH$, $-CH(CH_3)CH_2CH_2OH$, $-CH(CH_2CH_3)CH_2CH_2OH$, $-CH_2CH(OH)CH_2OH$, $-CH(CH_2OH)CH_2CH_2OH$, $-CH_2CH(OH)CH_2CH_2OH$, $-CH_2CH(OH)CH(OH)CH_2OH$, $-CH_2CH_2CH_2CH(OH)CH_2OH$, $-CH_2CH_2CH(OH)CH_2CH_2OH$, $-CH_2CH(OH)CH(OH)CH_2CH_2OH$, $-CH_2CH(OH)CH_2CH(OH)CH_2OH$, $-CH_2CH(OH)CH(OH)CH(OH)CH_2OH$, $-C(CH_2OH)_3$, and $-CH_2C(CH_2OH)_3$.

The term "$C_2-C_{10}$ alkoxyalkyl" as used herein refers to a saturated linear or branched $C_1-C_{10}$ chain consisting of 1 to 9 carbon atoms and at least one $-O-$ bond. Examples are $-CH_2OCH_3$, $-CH_2OCH_2CH_3$, $-CH_2CH_2OCH_3$, $-CH_2CH_2OCH_2CH_3$, $-CH_2OCH_2CH_2CH_3$, $-CH_2CH_2CH_2OCH_3$, $-CH_2CH_2CH_2OCH_2CH_3$, $-CH_2CH_2OCH_2CH_2CH_3$, $-CH_2OCH_2CH_2CH_2CH_3$, $-CH_2CH_2CH_2CH_2OCH_3$, $-CH_2CH_2CH_2CH_2OCH_2CH_3$, $-CH_2CH_2CH_2OCH_2CH_2CH_3$, $-CH_2CH_2OCH_2CH_2CH_2CH_3$, $-CH_2OCH_2CH_2CH_2CH_2CH_3$, $-CH_2OCH_2OCH_3$, $-CH_2CH_2OCH_2OCH_3$, $-CH_2OCH_2CH_2OCH_3$, $-CH_2OCH_2CH_2OCH_2CH_3$, $-CH_2CH_2OCH_2CH_2OCH_2CH_3$, $-CH_2OCH(CH_3)_2$, $-CH_2CH_2OCH(CH_3)_2$, $-CH_2CH_2OC(CH_3)_3$, $-CH_2OCH(CH_2CH_3)_2$, $-CH(OCH_3)_2$, $-CH_2CH(OCH_3)_2$, $-CH_2CH(OCH_3)CH_2OCH_3$, $-CH(OCH_2CH_3)_2$, and $-CH_2CH(OCH_2CH_3)_2$.

The term "$C_2-C_{10}$ carboxyalkyl" as used herein refers to a linear or branched $C_1-C_9$ carbon chain substituted by at least one carboxy group. The carbon atom number of $C_2-C_{10}$ refers to the carbon atoms of the carbon chain and the carboxy group.

Examples are $-CH_2CO_2H$, $-CH_2CH_2CO_2H$, $-CH_2CH_2CH_2CO_2H$, $-CH_2CH_2CH_2CH_2CO_2H$, $-CH_2CH_2CH_2CH_2CH_2CO_2H$, $-CH_2CH_2CH_2CH_2CH_2CH_2CO_2H$, $-CH(CO_2H)_2$, $-CH_2CH(CO_2H)CH_2CO_2H$, $-CH(CO_2H)CH_2CH_2CO_2H$, and $-CH_2CH(CO_2H)CH_2CH_2CO_2H$.

The term "$C_3-C_{11}$ alkyl carboxylic acid $C_1-C_4$ alkyl ester" as used herein refers to a linear or branched chain consisting of 1 to 9 carbon atoms substituted by one carboxylic acid group and at least one $C_1-C_4$ alkyl ester group. The carbon atom number of $C_3-C_{11}$ refers to the carbon atoms of the carbon chain, the carbon atom of carboxylic acid and the $-\underline{C}O_2$-carbon atom(s) of the at least one $C_1-C_4$ alkyl ester and thus the carbon atoms of $C_1-C_4$ alkyl group(s) of the at least one $C_1-C_6$ alkyl ester are not counted. The "$C_3-C_{11}$ alkyl carboxylic acid $C_1-C_4$ alkyl ester" is represented by the following formula: $HOOC-C_1-C_9$ alkyl-$CO-O-C_1-C_4$ alkyl. Herein $C_1-C_4$ alkyl ester is selected from a group consisting of $-CO_2CH_3$, $-CO_2C_2H_5$, $-CO_2C_3H_7$, $-CO_2CH(CH_3)_2$, $-CO_2CH_2CH=CH_2$, $-CO_2CH_2CH\equiv CH$, $-CO_2C_4H_9$, $-CO_2CH_2CH(CH_3)_2$, and $-CO_2C(CH_3)_3$.

Examples of $C_3-C_{11}$ alkyl carboxylic acid $C_1-C_6$ alkyl ester or of $HOOC-C_1-C_9$ alkyl-$CO-O-C_1-C_4$ alkyl are $HO_2C-CH_2-CO_2CH_3$, $HO_2C-CH_2-CO_2C_2H_5$, $HO_2C-CH_2CH_2-CO_2CH_3$, $HO_2C-CH_2CH_2-CO_2C_2H_5$, $HO_2C-CH_2CH_2-CO_2C_3H_7$, $HO_2C-CH_2CH_2-CO_2CH(CH_3)_2$, $HO_2C-CH_2CH_2-CO_2CH_2CH=CH_2$, $HO_2C-CH_2CH_2-CO_2CH_2CH\equiv CH$, $HO_2C-CH_2CH_2-CO_2C_4H_9$, $HO_2C-CH_2CH_2-CO_2CH_2CH(CH_3)_2$, $HO_2C-CH_2CH_2-CO_2C(CH_3)_3$, $HO_2C-CH_2CH_2CH_2-CO_2CH_3$, $HO_2C-CH_2CH_2CH_2-CO_2C_2H_5$, $HO_2C-CH_2CH_2CH_2CH_2-CO_2CH_3$, $HO_2C-CH_2CH_2CH_2CH_2CH_2-CO_2C_2H_5$, $HO_2C-CH_2CH(CH_2-CO_2CH_3)_2$, $HO_2C-CH_2CH(CO_2CH_3)CH_2-CO_2CH_3$, $HO_2C-CH_2CH_2CH_2CH_2CH_2CH_2-CO_2C_2H_5$, $HO_2C-CH_2CH_2CH(CH_2-CO_2CH_3)_2$, $HO_2C-CH_2CH_2CH_2CH_2CH_2CH_2CH_2-CO_2C_2H_5$, $HO_2O-CH_2CH_2CH_2CH_2CH_2CH_2CH_2CH_2-CO_2C_2H_5$, and $HO_2C-CH_2CH_2CH_2CH_2CH_2CH_2CH_2CH_2CH_2-CO_2C_2H_5$.

The term "$C_3-C_{10}$ alkoxycarbonylalkyl" as used herein refers to a saturated linear or branched chain consisting of 2 to 9 carbon atoms and at least one $-O_2C-$ bond. The carbon atom number of $C_3-C_{10}$ refers to the carbon atoms of the carbon chain and the $-O_2C-$ bond.

Examples are $CH_3CH_2O_2CCH_2-$, $CH_3CH_2CH_2O_2CCH_2-$, $CH_3CH_2CH_2CH_2O_2CCH_2-$, $(CH_3)_2CHO_2CCH_2-$, $(CH_3)_2CHO_2CCH_2-$, $(CH_3)_2CH_2CH_2O_2CCH_2-$, $(CH_3)_3CO_2CCH_2-$, $CH_3O_2CCH_2CH_2-$, $(CH_3)_2CH_2CHO_2CCH_2CH_2-$, $CH_3CH_2CH_2O_2CCH_2CH_2-$, $(CH_3)_2CHO_2CCH_2CH_2-$, $CH_3CH_2CH_2CH_2O_2CCH_2CH_2-$, $(CH_3)_2CH_2CH_2O_2CCH_2CH_2-$, $(CH_3)_3CO_2CCH_2CH_2-$, $CH_3O_2CCH_2CH(CO_2CH_3)CH_2-$, $CH_3CH_2O_2CCH_2CH_2CH_2-$, $CH_3CH_2CH_2O_2CCH_2CH_2CH_2-$, $(CH_3)_3CO_2CCH_2CH_2CH_2-$, $(CH_3)_2CHO_2CCH_2CH_2CH_2-$, $CH_3CH_2CH_2O_2CCH_2CH_2CH_2-$, $CH_3O_2CCH_2O_2CCH_2-$, $CH_3CH_2O_2CCH_2O_2CCH_2-$, $CH_3CH_2CH_2O_2CCH_2O_2CCH_2-$, $CH_3CH_2O_2CCH_2CH_2-$, $(CH_3)_2CHO_2CCH_2O_2CCH_2-$, $CH_3CH_2CH_2CH_2O_2CCH_2O_2CCH_2-$, $CH_3O_2CCH_2-$, $(CH_3)_2CH_2CH_2O_2CCH_2O_2CCH_2-$, $(CH_3)_3CO_2CCH_2O_2CCH_2-$, $CH_3O_2CCH_2CH_2O_2CCH_2-$, $CH_3CH_2O_2CCH_2CH_2O_2CCH_2-$, $CH_3CH_2CH_2O_2CCH_2CH_2O_2CCH_2-$, $CH_3CH_2O_2CCH_2-$, $CH_3CH_2CH_2CH_2O_2CCH_2CH_2O_2CCH_2-$, $(CH_3)_2CH_2CHO_2CCH_2CH_2O_2CCH_2-$, $(CH_3)_3CO_2CCH_2CH_2O_2CCH_2-$, $(CH_3O_2C)_2CH-$, $(CH_3CH_2O_2C)_2CH-$, $(CH_3O_2C)_2CHCH_2-$, $(CH_3O_2C)_2CHCH_2CH_2-$ and $CH_3O_2CCH_2CH_2CH_2-$.

The term "$C_2$-$C_{10}$ acyloxyalkyl" as used herein refers to a saturated linear or branched chain consisting of 1 to 9 carbon atoms and at least one —$CO_2$— bond. The carbon atom number of $C_3$-$C_{10}$ refers to the carbon atoms of the carbon chain and the —$CO_2$— bond.

Examples are $CH_3CO_2CH_2$—, $CH_3CH_2CO_2CH_2$—, $CH_3CH_2CH_2CO_2CH_2$—, $(CH_3)_2CHCO_2CH_2$—, $CH_3CH_2CH_2CH_2CO_2CH_2$—, $(CH_3)_2CH_2CH_2CO_2CH_2$—, $(CH_3)_3CCO_2CH_2$—, $CH_3CO_2CH_2CH_2$—, $CH_3CH_2CO_2CH_2CH_2$—, $CH_3CH_2CH_2CO_2CH_2CH_2$—, $(CH_3)_2CHCO_2CH_2CH_2$—, $CH_3CH_2CH_2CH_2CO_2CH_2CH_2$—, $(CH_3)_2CH_2CH_2CO_2CH_2CH_2$—, $(CH_3)_3CCO_2CH_2CH_2$—, $(CH_3)_2CHCO_2CH_2CH_2CH_2$—, $CH_3CH_2CH_2CH_2CO_2CH_2CH_2CH_2$—, $CH_3CO_2CH_2CH_2CH_2$—, $CH_3CH_2CO_2CH_2CH_2CH_2$—, $CH_3CH_2CH_2CO_2CH_2CH_2CH_2$—, $(CH_3)_2CH_2CH_2CO_2CH_2CH_2CH_2$—, $CH_3CO_2CH_2CH_2$—, $(CH_3)_3CCO_2CH_2CH_2CH_2$—, $CH_3CO_2CH_2CO_2CH_2$—, $CH_3CH_2CO_2CH_2CO_2CH_2$—, $CH_3CH_2CO_2CH_2CO_2CH_2$—, $(CH_3)_2CHCO_2CH_2CO_2CH_2$—, $CH_3CH_2CH_2CH_2CO_2CH_2CO_2CH_2$—, $(CH_3CO_2)_2CHCH_2$—, $(CH_3)_2CH_2CH_2CO_2CH_2CO_2CH_2$—, $(CH_3)_3CCO_2CH_2CO_2CH_2$—, $CH_3CO_2CH_2CH_2CO_2CH_2$—, $CH_3CH_2CO_2CH_2CH_2CO_2CH_2$—, $CH_3CH_2CH_2CO_2CH_2CH_2CO_2CH_2$—, $(CH_3CO_2)_2CH$—, $(CH_3)_2CHCO_2CH_2CH_2CO_2CH_2$—, $CH_3CH_2CH_2CH_2CO_2CH_2CH_2CO_2CH_2$—, $CH_3CO_2CH_2CH(O_2CCH_3)CH(O_2CCH_3)CH_2$—, $(CH_3)_2CH_2CHCO_2CH_2CH_2CO_2CH_2$—, $(CH_3)_3CCO_2CH_2CH_2CO_2CH_2$—, $(CH_3CO_2)_2CHCH_2CH_2$—, and $CH_3CO_2CH_2CH(O_2CCH_3)CH_2$—.

The term "$C_3$-$C_{10}$ alkylcarbonylaminoalkyl" as used herein refers to a saturated linear or branched chain consisting of 1 to 9 carbon atoms and at least one —CONH— bond. The carbon atom number of $C_3$-$C_{10}$ refers to the carbon atoms of the carbon chain and the —CONH— bond.

Examples are $CH_3CONHCH_2$—, $CH_3CH_2CONHCH_2$—, $CH_3CH_2CH_2CONHCH_2$—, $(CH_3)_2CHCONHCH_2$—, $CH_3CH_2CH_2CH_2CONHCH_2$—, $(CH_3)_2CH_2CH_2CONHCH_2$—, $(CH_3)_3CCONHCH_2$—, $CH_3CH_2CH_2CH_2CONHCH_2CH_2$—, $(CH_3)_2CH_2CH_2CONHCH_2CH_2$—, $CH_3CONHCH_2CH_2$—, $CH_3CH_2CONHCH_2CONHCH_2$—, $CH_3CH_2CH_2CONHCH_2CONHCH_2$—, $CH_3CH_2CONHCH_2CH_2$—, $CH_3CH_2CH_2CONHCH_2CH_2$—, $(CH_3)_2CHCONHCH_2CH_2$—, $(CH_3)_3CCONHCH_2CH_2$—, $CH_3CONHCH_2CH_2CH_2$—, $CH_3CH_2CONHCH_2CH_2CH_2$—, $CH_3CH_2CH_2CONHCH_2CH_2CH_2$—, $(CH_3)_2CHCONHCH_2CH_2CH_2$—, $CH_3CH_2CH_2CH_2CONHCH_2CH_2CH_2$—, $(CH_3)_2CH_2CH_2CONHCH_2CH_2CH_2$—, $(CH_3)_3CCONHCH_2CH_2CH_2$—, $CH_3CONHCH_2CONHCH_2$—, $(CH_3)_2CHCONHCH_2CNHCH_2$—, $CH_3CONHCH_2CH(NHOCCH_3)CH(NHOCCH_3)CH_2$—, $CH_3CONHCH(CH_3)CONHCH_2$—, $CH_3CONHCH(CH(CH_3)_2)CONHCH_2$—, $CH_3CONHCH(CH_2CH_3)CONHCH_2$—, and $CH_3CONHCH_2CH(NHOCCH_3)CH_2$—.

The term "$C_3$-$C_{10}$ alkoxycarbonylaminoalkyl" as used herein refers to a saturated linear or branched chain consisting of 1 to 9 carbon atoms and at least one —OCONH— bond. The carbon atom number of $C_3$-$C_{10}$ refers to the carbon atoms of the carbon chain and the —OCONH— bond.

Examples are $CH_3OCONHCH_2$—, $CH_3CH_2OCONHCH_2$—, $CH_3CH_2CH_2OCONHCH_2$—, $(CH_3)_2CHOCONHCH_2$—, $CH_3CH_2CH_2CH_2OCONHCH_2$—, $(CH_3)_2CH_2CH_2OCONHCH_2$—, $(CH_3)_3COCONHCH_2$—, $CH_3CH_2CH_2CH_2OCONHCH_2CH_2$—, $(CH_3)_2CH_2CH_2OCONHCH_2CH_2$—, $CH_3OCONHCH_2CH_2$—, $CH_3CH_2OCONHCH_2CONHCH_2$—, $CH_3CH_2CH_2CONHCH_2OCONHCH_2$—, $CH_3CH_2OCONHCH_2CH_2$—, $CH_3CH_2CH_2OCONHCH_2CH_2$—, $(CH_3)_2CHOCONHCH_2CH_2$—, $(CH_3)_3COCONHCH_2CH_2$—, $CH_3OCONHCH_2CH_2$—, $CH_3CH_2OCONHCH_2CH_2CH_2$—, $CH_3CH_2OCONHCH_2CH_2CH_2$—, $(CH_3)_2CHOCONHCH_2CH_2CH_2$—, $CH_3CH_2CH_2CH_2OCONHCH_2CH_2$—, $(CH_3)_2CH_2CH_2OCONHCH_2CH_2$—, $(CH_3)_3COCONHCH_2CH_2$—, $CH_3OCONHCH_2OCONHCH_2$—, $(CH_3)_2CHOCONHCH_2OCONHCH_2$—, $CH_3OCONHCH(CH_3)OCONHCH_2$—, $CH_3OCONHCH(CH(CH_3)_2)OCONHCH_2$—, $CH_3OCONHCH(CH_2CH_3)OCONHCH_2$—, $CH_3OCONHCH_2CH(NHOCOCH_3)CH_2$—, and $CH_3OCONHCH_2CH(NHOCOCH_3)CH(NHOCOCH_3)CH_2$—.

The term "$C_1$-$C_{10}$ aminoalkyl" as used herein refers to a saturated linear or branched $C_1$-$C_{10}$ alkyl group substituted by at least one amino group. It is clear to a skilled person that the term "substituted" refers to the replacement of a hydrogen atom by one of the substituents. Examples are —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH(CH_3)CH_2NH_2$—$CH(CH_3)CH_2CH_2NH_2$, —$CH(CH_2CH_3)CH_2CH_2NH_2$, —$CH_2CH(NH_2)CH_2NH_2$, —$CH(CH_2NH_2)CH_2CH_2NH_2$, —$CH_2CH(NH_2)CH_2CH_2NH_2$, —$CH_2CH(NH_2)CH(NH_2)CH_2NH_2$, —$CH_2CH_2CH(NH_2)CH_2NH_2$, —$CH_2CH_2CH(NH_2)CH_2CH_2NH_2$, —$CH_2CH(NH_2)CH(NH_2)CH_2CH_2NH_2$, and —$CH_2C(CH_2NH_2)_3$.

The term "$C_2$-$C_{10}$ alkylaminoalkyl" as used herein refers to a saturated linear or branched chain consisting of 2 to 10 carbon atoms and at least one —NH— bond.

Examples are —$CH_2NHCH_3$, —$CH_2NHCH_2CH_3$, —$CH_2NHCH(CH_3)_2$, —$CH_2NHCH_2CH_2CH_3$, —$CH_2NHCH_2CH(CH_3)_2$, —$CH_2NHC(CH_3)_3$, —$CH_2CH_2NHCH_3$, —$CH_2CH_2CH_2NHCH_3$, —$CH_2CH_2CH_2CH_2NHCH_3$, —$CH_2CH_2CH_2CH_2CH_2NHCH_3$, —$CH_2CH_2CH_2CH_2NHCH_2CH_3$, —$CH_2CH_2CH_2NHCH_2CH_3$, —$CH_2CH_2NHCH_2CH_2CH_3$, —$CH(CH_3)CH_2NHCH_3$, —$CH_2NHCH_2CH_2NHCH_3$, —$CH_2CH_2NHCH_2NHCH_2CH_3$, —$CH_2NHCH_2NHCH_2CH_3$, —$CH_2CH(NHCH_3)CH_2NHCH_3$, and —$CH_2CH(NHCH_2CH_3)_2$.

The term "$C_3$-$C_{10}$ dialkylaminoalkyl" as used herein refers to a linear or branched $C_1$-$C_{10}$ carbon chain substituted by at least one secondary amino group di-substituted by $C_1$-$C_4$ alkyl group. It is clear to a skilled person that the term "substituted" refers to the replacement of a hydrogen atom by one of the substituents. The carbon atom number of $C_1$-$C_{10}$ refers only to the carbon atoms of the carbon chain.

Examples are —$CH_2N(CH_3)_2$, —$CH_2CH_2N(CH_3)_2$, —$CH_2CH_2CH_2N(CH_3)_2$, —$CH_2CH_2N(CH_2CH_3)_2$, —$CH_2CH_2CH_2N(CH_2CH_3)_2$, —$CH_2CH_2N(CH(CH_3)_2)_2$, —$CH_2CH_2CH_2N(CH(CH_3)_2)_2$, —$CH_2N(CH_2CH_2CH_2CH_3)_2$, —$CH_2CH_2N(CH_2CH_2CH_2CH_3)_2$, —CH₂CH₂N(CH₂CH(CH₃)₂)₂, —CH₂CH(N(CH₃)₂)CH₃, —CH₂CH(N(CH₃)₂)CH₂CH₃, and —CH₂CH(N(CH₃)₂)CH₂CH₂(N(CH₃)₂).

The term "$C_3$-$C_{10}$ alkylaminocarbonylalkyl" as used herein refers to a saturated linear or branched chain consisting of 1 to 9 carbon atoms and at least one —NHCO— bond. The carbon atom number of $C_3$-$C_{10}$ refers to the carbon atoms of the carbon chain and the —NHCO— bond.

Examples are CH₃NHCOCH₂—, CH₃CH₂NHCOCH₂—, CH₃CH₂CH₂NHCOCH₂—, (CH₃)₂CHNHCOCH₂—, CH₃CH₂CH₂CH₂NHCOCH₂—, (CH₃)₂CH₂CH₂NHCOCH₂—, (CH₃)₃CNHCOCH₂—, CH₃CH₂CH₂CH₂NHCOCH₂CH₂—, (CH₃)₂CH₂CH₂NHCOCH₂CH₂—, CH₃CONHCH₂CH₂—, CH₃CH₂CONHCH₂CONHCH₂—, CH₃CH₂CH₂CONHCH₂CONHCH₂—, CH₃CH₂CONHCH₂CH₂—, CH₃CH₂CH₂CONHCH₂CH₂—, (CH₃)₂CHCONHCH₂CH₂—, (CH₃)₃CCONHCH₂CH₂—, CH₃CONHCH₂CH₂CH₂—, CH₃CH₂CONHCH₂CH₂CH₂—, CH₃CH₂CH₂CONHCH₂CH₂CH₂—, (CH₃)₂CHCONHCH₂CH₂CH₂—, CH₃CH₂CH₂CH₂CONHCH₂CH₂CH₂—, (CH₃)₂CH₂CH₂CONHCH₂CH₂CH₂—, (CH₃)₃CCONHCH₂CH₂CH₂—, CH₃CONHCH₂CONHCH₂—, (CH₃)₂CHCONHCH₂CNHCH₂—, CH₃CONHCH(CH₃)CONHCH₂—, CH₃CONHCH(CH(CH₃)₂)CONHCH₂—, CH₃CONHCH(CH₂CH₃)CONHCH₂—, CH₃CONHCH₂CH(NHOCCH₃)CH₂—, and CH₃CONHCH₂CH(NHOCCH₃)CH(NHOCCH₃)CH₂—.

The term "$C_4$-$C_{10}$ dialkylaminocarbonylalkyl" as used herein refers to a linear or branched $C_1$-$C_{10}$ carbon chain substituted by at least one secondary aminocarbonyl group di-substituted by $C_1$-$C_4$ alkyl group. It is clear to a skilled person that the term "substituted" refers to the replacement of a hydrogen atom by one of the substituents. The carbon atom number of $C_1$-$C_{10}$ refers only to the carbon atoms of the carbon chain.

Examples are —CH₂CON(CH₃)₂, —CH₂CH₂CON(CH₃)₂, —CH₂CH₂CH₂CON(CH₃)₂, —CH₂CH₂CON(CH₂CH₃)₂, —CH₂CH₂CH₂CON(CH₂CH₃)₂, —CH₂CH₂CON(CH(CH₃)₂)₂, —CH₂CH₂CH₂CON(CH(CH₃)₂)₂, —CH₂CON(CH₂CH₂CH₂CH₃)₂, —CH₂CH₂CON(CH₂CH₂CH₂CH₃)₂, —CH₂CH₂CON(CH₂CH(CH₃)₂)₂, —CH₂CH(CON(CH₃)₂)CH₃, —CH₂CH(CON(CH₃)₂)CH₂CH₃, and —CH₂CH(CON(CH₃)₂)CH₂CH₂(CON(CH₃)₂).

The term "$C_6$-$C_{14}$ aryl" as used herein refers to aromatic residues or more specific to aromatic carbocyclic residues with one, two or three aromatic rings and refers preferably to phenyl and naphthyl, wherein these phenyl and naphthyl residues can be substituted with 1 to 5 substituents selected from —F, —Cl, —Br, —I, —CN, —NO₂, —OH, —CO₂H, —CO₂CH₃, —CO₂C₂H₅, —COCH₃, —COCF₃, —SO₃H, —SO₂CH₃, —SO₂CF₃, —NH₂, —NHCOCH₃, —NHSO₂CH₃, —NHSO₂CF₃, —NHCH₃, —N(CH₃)₂, —CH₂NH₂, —CH₂OH, —OCH₃, —OCHF₂, OCF₃ and —CF₃. However it is clear to a skilled person that the term "can be substituted" refers to the replacement of a hydrogen atom by one of the said substituents. The carbon atom number of $C_6$-$C_{14}$ refers only to the carbon atoms of the aromatic ring system (aryl) and does not include the carbon atoms of the said substituents. Examples are

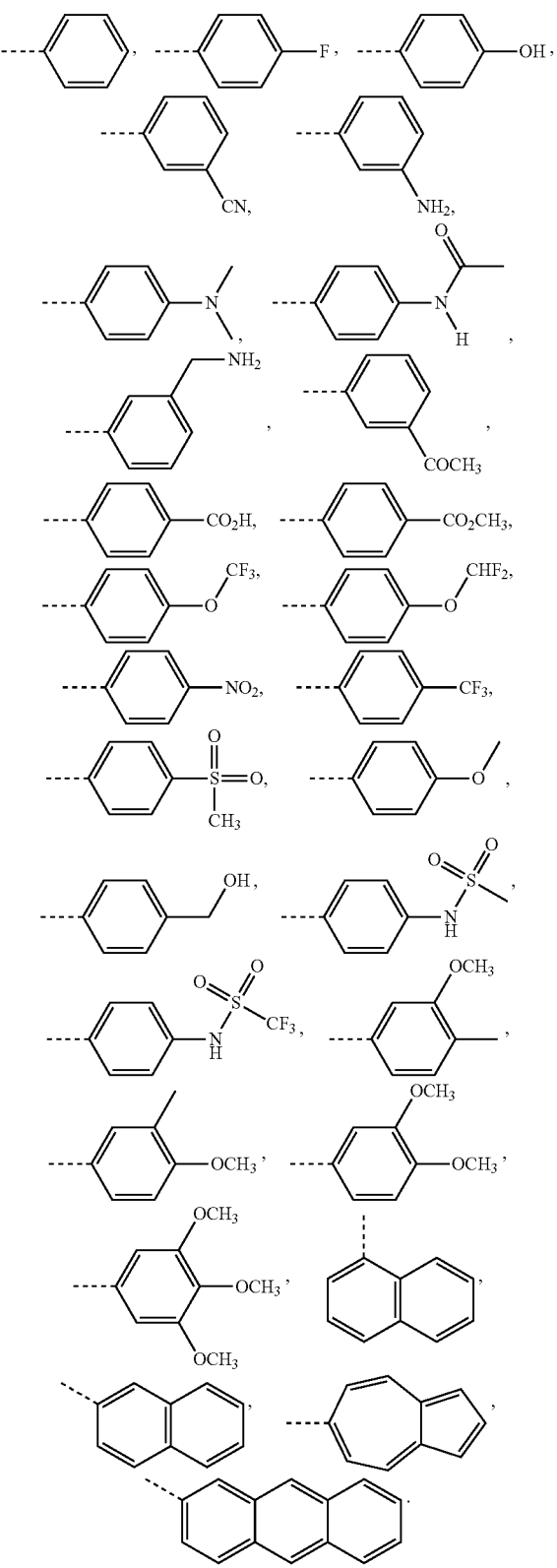

The term "$C_2$-$C_{10}$ alkenyl" as used herein refers to a linear or branched carbon chain containing at least one double bond. Examples are: —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C (CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₂H₄—CH=CH—CH=CH₂, —CH₂—CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH=CH—CH=CH—C₂H₅, —CH=CH—CH=C(CH₃)₂, and —CH=CH—CH=CH—CH=CH₂.

The term "$C_2$-$C_{10}$ alkynyl" as used herein refers to a linear or branched carbon chain containing at least one triple bond. Examples are: —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C≡CH, —CH₂—C≡C—C≡CH, —C≡C—C≡C—CH₃, —CH(C≡CH)₂.

The term "$C_3$-$C_8$ cycloalkyl" as used herein refers to cyclo-C₃H₅, cyclo-C₄H₇, cyclo-C₅H₉, cyclo-C₆H₁₁, cyclo-C₇H₁₃, and cyclo-C₈H₁₅, wherein these cyclic residues can be substituted with 1 to 5 substituents selected from —F, —Cl, —Br, —I, —CN, —NO₂, —OH, —CO₂H, —CO₂CH₃, —CO₂C₂H₅, —COCH₃, —SO₂CH₃, —SO₂CF₃, —NH₂, —NHCOCH₃, —NHSO₂CH₃, —NHSO₂CF₃, —NHCH₃, —N(CH₃)₂, —CH₂OH, —OCH₃, —OCHF₂, —OCF₃ and —CF₃. However it is clear to a skilled person that the term "can be substituted" refers to the replacement of a hydrogen atom by one of the said substituents. The carbon atom number of $C_3$-$C_8$ refers only to the carbon atoms of the cyclic residues and does not include the carbon atoms of the said substituents.

Examples of preferred carbocyclic residues are:

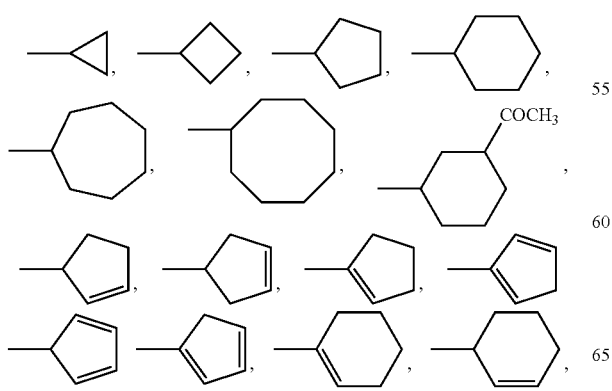

The term "$C_4$-$C_{10}$ alkylcycloalkyl" as used herein refers to cyclo-C₃H₅, cyclo-C₄H₇, cyclo-C₅H₉, cyclo-C₆H₁₁, cyclo-C₇H₁₃, and cyclo-C₈H₁₅ which are substituted with 1 to 5 substituents selected from said $C_1$-$C_{10}$ alkyl groups. However it is clear to a skilled person that the term "are substituted" refers to the replacement of a hydrogen atom by one of the abovementioned substituents. The carbon atom number of $C_4$-$C_{18}$ refers to the carbon atoms of the cycloalkyl residue and the carbon atoms of the substituents.

Examples are

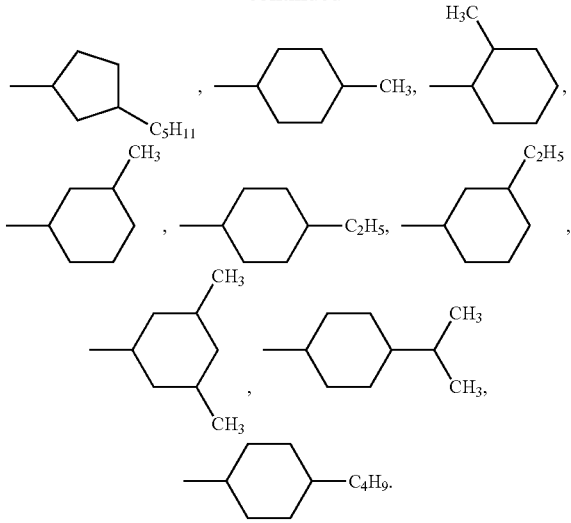

The term "C$_4$-C$_{10}$ alkoxyalkylcycloalkyl" as used herein refers to cyclo-C$_3$H$_5$, cyclo-C$_4$H$_7$, cyclo-C$_5$H$_9$, cyclo-C$_6$H$_{11}$, cyclo-C$_7$H$_{13}$, and cyclo-C$_8$H$_{15}$ which are substituted with 1 to 5 substituents selected from C$_1$-C$_6$ alkoxyalkyl groups. However it is clear to a skilled person that the term "are substituted" refers to the replacement of a hydrogen atom by one of the abovementioned substituents. The carbon atom number of C$_4$-C$_{10}$ refers to the carbon atoms of the cycloalkyl residue and the carbon atoms of the substituted alkoxyalkyl group.
Examples are

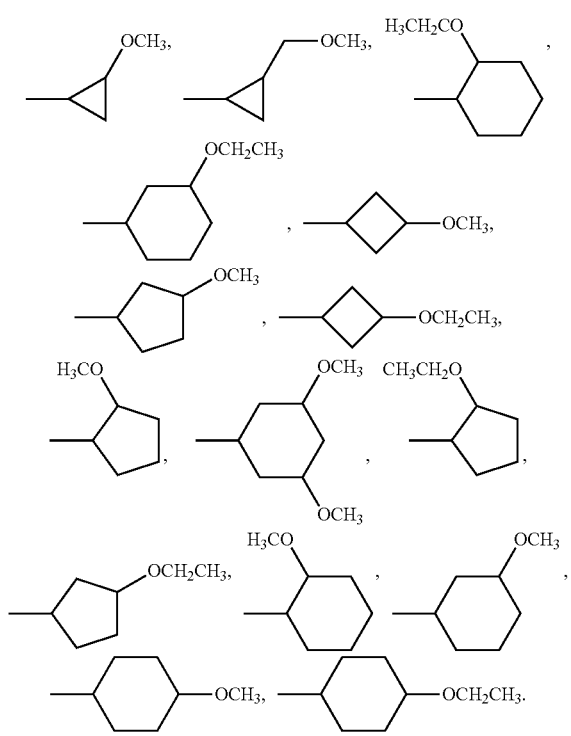

The term "C$_4$-C$_{12}$ cycloalkylalkyl" as used herein refers to said C$_1$-C$_{10}$ alkyl residue which are further substituted with 1 to 5 substituents selected from said C$_3$-C$_8$ cycloalkyl, C$_4$-C$_{10}$ alkylcycloalkyl or C$_4$-C$_{10}$ alkoxyalkylcycloalkyl groups. It is clear to a skilled person that the term "are substituted" refers to the replacement of a hydrogen atom by one of the abovementioned substituents. The carbon atom number of C$_4$-C$_{10}$ refers to the carbon atoms of the C$_1$-C$_{10}$ alkyl residue and the carbon atoms of the substituents. Examples are

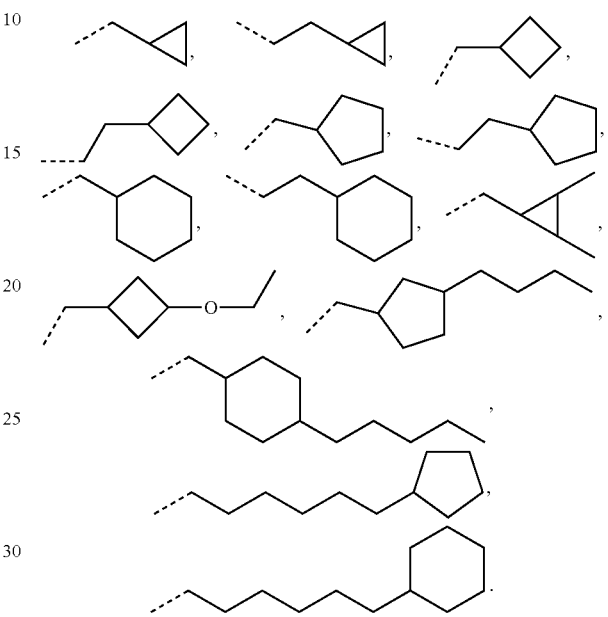

The term "C$_4$-C$_{16}$ cycloalkylalkoxyalkyl" as used herein refers to said C$_1$-C$_{10}$ alkoxyalkyl residue which are further substituted with 1 to 5 substituents selected from said C$_3$-C$_8$ cycloalkyl, C$_4$-C$_{10}$ alkylcycloalkyl or C$_4$-C$_{10}$ alkoxyalkyl-cycloalkyl groups. It is clear to a skilled person that the term "are substituted" refers to the replacement of a hydrogen atom by one of the abovementioned substituents. The carbon atom number of C$_4$-C$_{10}$ refers to the carbon atoms of the C$_1$-C$_{10}$ alkyl residue and the carbon atoms of the substituents.
Examples are

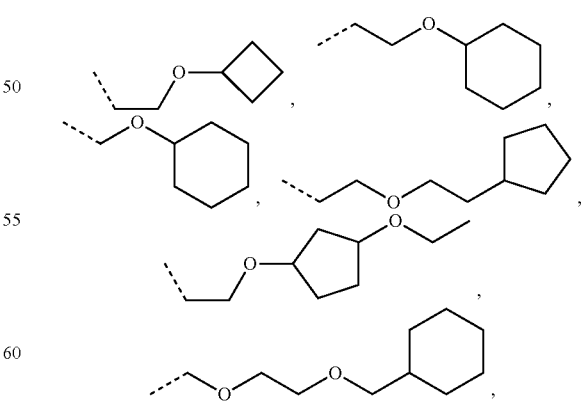

The term "C$_7$-C$_{16}$ alkylaryl" as used herein refers to said C$_6$-C$_{14}$-aryl substituted with 1 to 5 substituents selected from said C$_1$-C$_{10}$ alkyl, said C$_1$-C$_{10}$ halogenalkyl, said C$_1$-C$_{10}$ hydroxyalkyl, said C$_2$-C$_{10}$ carboxyalkyl, said C$_3$-C$_8$ cycloalkyl or said $C_4$-$C_{10}$ cycloalkylalkyl group. It is clear to a skilled person that the term "substituted" refers to the replacement of a hydrogen atom by one of the substituents. The carbon atom number of $C_7$-$C_{16}$ refers to the carbon atoms of the aromatic ring system (aryl) and the carbon atoms of the said substituents.

Examples are

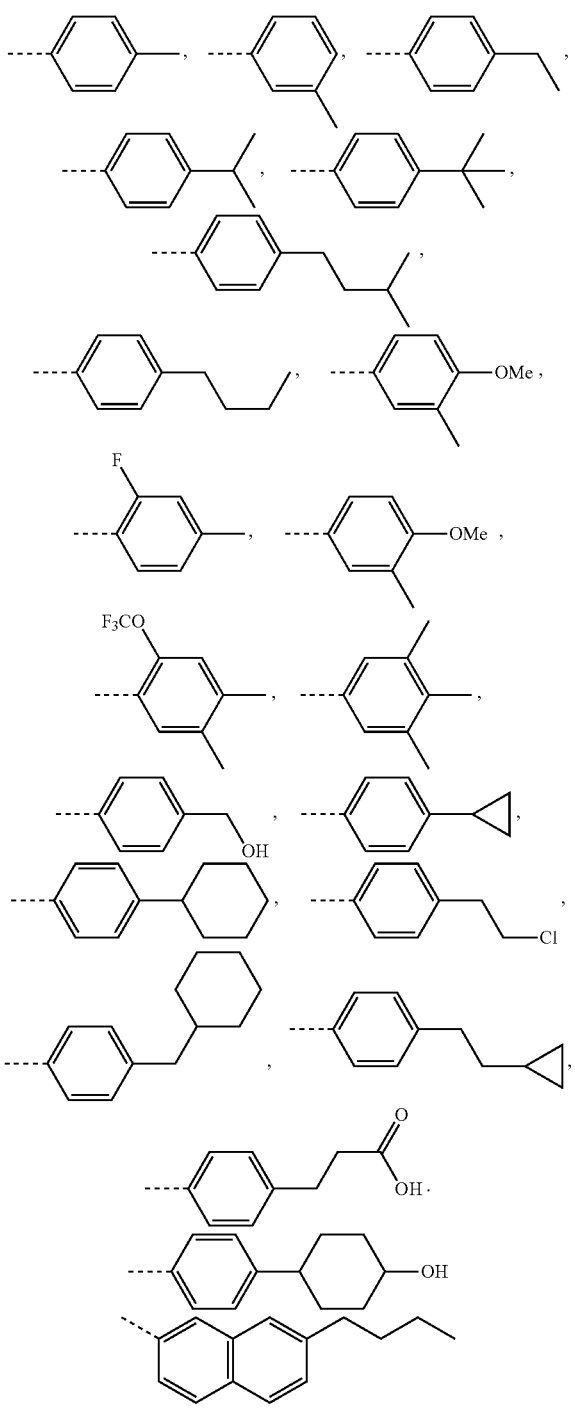

The term "$C_8$-$C_{16}$ alkoxyaryl" as used herein refers to said $C_6$-$C_{14}$-aryl substituted with 1 to 5 substituents selected from said $C_1$-$C_{10}$ alkoxyalkyl, or said $C_4$-$C_{10}$ cycloalkoxyalkyl group. It is clear to a skilled person that the term "substituted" refers to the replacement of a hydrogen atom by one of the substituents. The carbon atom number of $C_7$-$C_{16}$ refers to the carbon atoms of the aromatic ring system (aryl) and the carbon atoms of the said substituents. Examples are

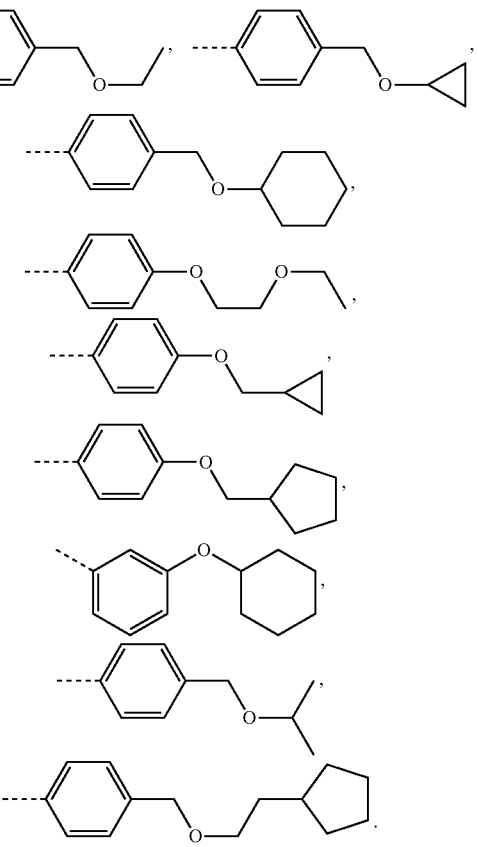

The term "$C_7$-$C_{20}$ arylalkyl" as used herein refers to said $C_1$-$C_{10}$ alkyl residues which are substituted with 1 to 5 substituents selected from said $C_6$-$C_{14}$ aryl, said $C_7$-$C_{16}$ alkylaryl or said $C_7$-$C_{16}$ alkoxyaryl substituents. It is clear to a skilled person that the term "are substituted" refers to the replacement of a hydrogen atom by one of the said substituents. The carbon atom number of $C_7$-$C_{16}$ refers to the carbon atoms of the aromatic ring system (aryl) and the carbon atoms of the said substituents. Examples are

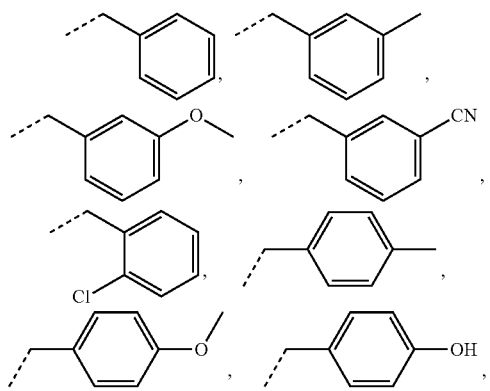

-continued

The term "C$_7$-C$_{16}$ arylalkoxylalkyl" as used herein refers to said C$_1$-C$_{10}$ alkoxyalkyl residues which are substituted with 1 to 5 substituents selected from said C$_6$-C$_{14}$ aryl, said C$_7$-C$_{16}$ alkylaryl or said C$_7$-C$_{16}$ alkoxyaryl substituents. It is clear to a skilled person that the term "are substituted" refers to the replacement of a hydrogen atom by one of the said substituents. The carbon atom number of C$_7$-C$_{16}$ refers to the carbon atoms of the aromatic ring system (aryl) and the carbon atoms of the said substituents. Examples are

The term "C$_1$-C$_5$ heterocyclyl" as used herein refers to saturated/monounsaturated/unsaturated 3-membered, 4-membered, 5-membered, 6-membered, bicyclic heterocyclic residues, wherein these heterocyclic residues can be substituted with 1 to 5 substituents selected from —F, —Cl, —Br, —I, —CN, —NO$_2$, —OH, —CO$_2$H, —CO$_2$CH$_3$, —CO$_2$C$_2$H$_5$, —COCH$_3$, —SO$_2$CH$_3$, —SO$_2$CF$_3$, —NH$_2$, —NHCOCH$_3$, —NHSO$_2$CH$_3$, —NHSO$_2$CF$_3$, —NHCH$_3$, —N(CH$_3$)$_2$, —CH$_2$OH, —OCH$_3$, —OCHF$_2$, —OCF$_3$ and —CF$_3$. However it is clear to a skilled person that the term "can be substituted" refers to the replacement of a hydrogen atom by one of the said substituents.

Examples are pyridyl, pyrimidinyl, pyrazinyl, pyridazinyl, triazinyl, imidazolyl, furyl, dihydrofuryl, tetrahydrofuryl, thienyl, dihydrothienyl, tetrahydrothienyl, 1,3-oxazolyl, dihydro-1,3-oxazolyl, 1,3-oxazolidinyl, isoxazolyl, dihydroisoxazolyl, isoxazolidinyl, pyrrolyl, dihydropyrrolyl, pyrrolidinyl, imidazolyl, dihydroimidazolyl, imidazolidinyl, triazolyl, dihydrotriazolyl, triazolidinyl, pyrazolyl, dihydropyrazolyl, pyrazolidinyl, oxadiazolyl, dihydrooxadiazolyl, oxadiazolidinyl, thiadiazolyl, dihydrothiadiazolyl, thiadiazolidinyl, 1,3-thiazolyl, dihydro-1,3-thiazolyl, 1,3-thiazolidinyl, isothiazolyl, dihydroisothiazolyl, isothiazolidinyl, tetrazolyl, dihydrotetrazolyl, tetrazolidinyl, aziridinyl, azirenyl, oxiranyl, thiiranyl, azetidinyl, oxetanyl, thietanyl, cyclopentanonyl, cyclohexanonyl, pyrrolidinonyl, pyrrolidindionyl, piperidinonyl, piperidinyl, 1-oxid-thiopyranyl, 1,1-dioxid-thiopyranyl, dihydro-1-oxid-thiopyranyl, dihydro-1,1-dioxid-thiopyranyl, tetrahydro-1-oxid-thiopyranyl, tetrahydro-1,1-dioxid-thiopyranyl, morpholinyl, thiomorpholinyl, 1,2-dioxanyl, 1,3-dioxanyl, 1,4-dioxanyl, 1,2-dioxolanyl, 1,3-dioxolanyl, 1,4-dioxolanyl, piperazinyl, 2-oxo-azetidinyl, 2-oxo-pyrrolidinyl, 2-oxo-piperidinyl, 2-oxo-oxazolidinyl, 2-oxo-imidazolidinyl, 2-oxo-1,3-oxazinanyl, 2-oxo-tetrahydropyrimidinyl.

The term "C$_3$-C$_{12}$ heterocyclylalkyl" as used herein refers to said C$_1$-C$_7$ alkyl residues which are substituted with 1 to 5 substituents selected from said C$_2$-C$_5$ heterocyclyl group. It is clear to a skilled person that the term "are substituted" refers to the replacement of a hydrogen atom by one of the abovementioned substituents. The carbon atom number of C$_3$-C$_{12}$ refers to the carbon atoms of the C$_1$-C$_7$ alkyl residue and the carbon atoms of the substituents. Examples are

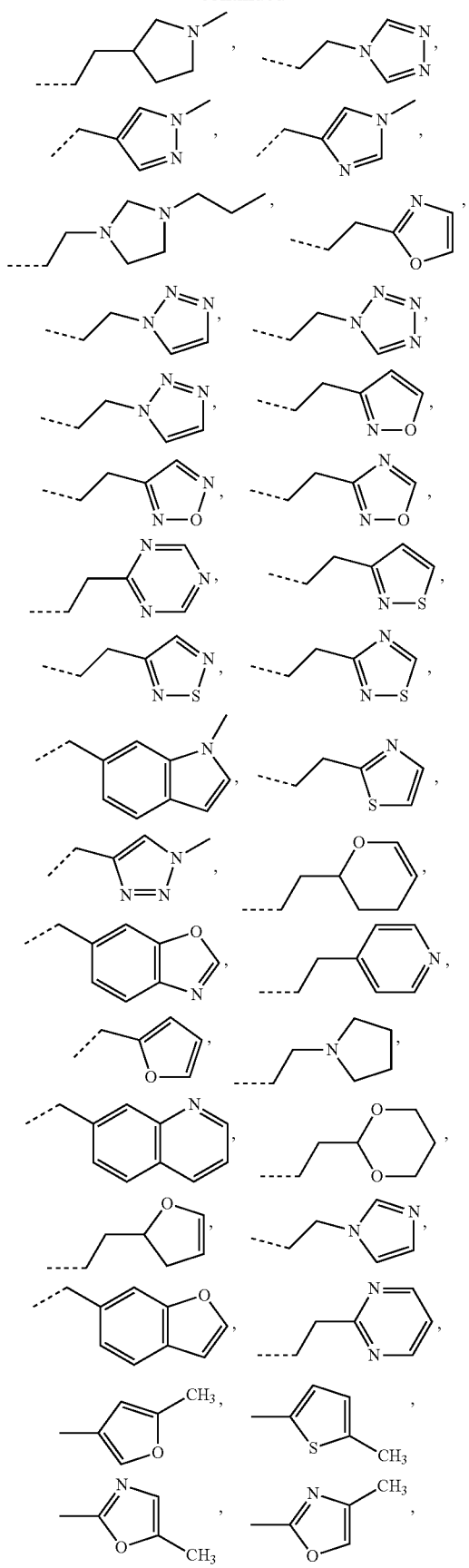
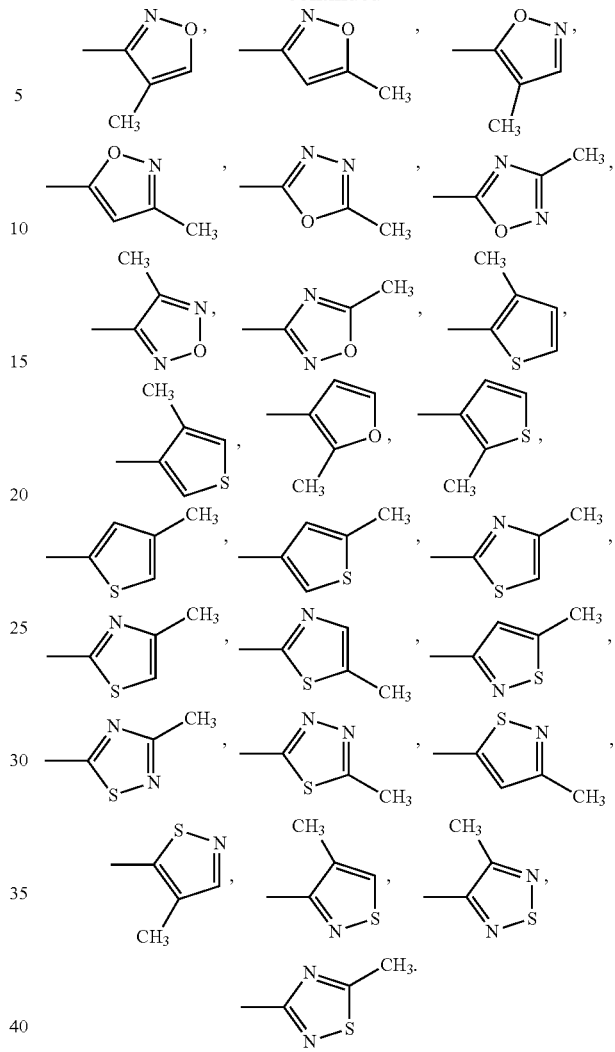

R represents more preferably: —R¹, —COR¹, and

R¹ represents —CH₃, —C₂H₅, —C₃H₇, —CH(CH₃)₂, —C₄H₉, —CH₂CH(CH₃)₂, —CH(CH₃)C₂H₅, —C(CH₃)₃, —C₅H₁₁, —CH(CH₃)C₃H₇, —CH(C₂H₅)₂, —C₂H₄CH(CH₃)₂, —CH₂CH(CH₃)C₂H₅, —CH(CH₃)CH(CH₃)₂, —C(CH₃)₂C₂H₅, —C₆H₁₃, -cyclo-C₃H₅, -cyclo-C₄H₇, -cyclo-C₅H₉, -cyclo-C₆H₁₁, —CH₂CO₂H, —(CH₂)₂CO₂H, —(CH₂)₃CO₂H, —(CH₂)₄CO₂H, or

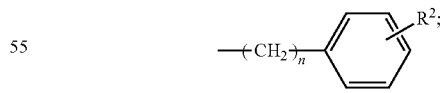

and

R² represents —H, —OH, —F, —Br, —Cl, —CN, —NO₂, —CO₂H, —CO₂CH₃, —CO₂C₂H₅, —SO₃H, —CH₃, —C₂H₅, —CH(CH₃)₂, —OCH₃, —OC₂H₅, —OCH(CH₃)₂, —CF₃, —OCHF₂, —OCF₃, —NH₂, —NHCH₃, —N(CH₃)₂, —NHCOCH₃, —NHSO₂CH₃, —NHSO₂CF₃, or —SO₂CH₃; and n is the integer from 0, 1 or 2.

Scheme 1

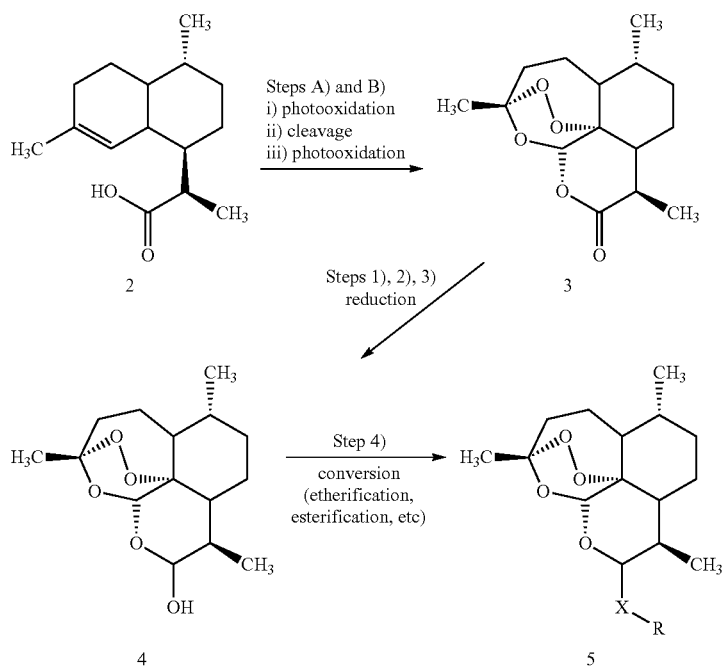

Concerning the continuous methods for reducing artemisinin as disclosed herein, it is preferred in regard to the one column embodiment to prepare a homogeneous mixture of the hydride reducing agent, the at least one activator and the at least one solid base which is than filled into the column as disclosed below. However it is also possible to prepare a homogeneous mixture of the hydride reducing agent and the at least one activator which is filled into the column as bottom layer on which top a layer of the at least one solid base is places.

The hydride reducing agent, the at least one activator and the at least one solid base are preferably provided as solid materials in a crystalline or powder form.

If the two column embodiment is used, the at least one solid base is filled into the first column and a preferably homogeneous mixture of the hydride reducing agent and the at least one activator is filled into the second column which is preferably in close distance connected to the first column. Both columns should allow the same or identical flow rate of the artemisinin solution.

It was found that a preferred molar ratio of artemisinin to hydride reducing agent is in the range of 1.0:1.0 to 1.0:2.0.

The hydride reducing agent is preferably selected from the group consisting of sodium borohydride (NaBH$_4$), lithium borohydride (LiBH$_4$), potassium borohydride (KBH$_4$), calcium borohydride (Ca(BH$_4$)$_2$), Superhydride® (is a solution of lithium triethylborohydride), L/K/N-Selectrides (refers to lithium/potassium/sodium tri(sec-butyl) borohdyride), LiAlH(OtBu)$_3$, RedAl, DIBAL-H (used at −76° C.), Titanocene (exists as dimer) and a mixture of the afore-mentioned reducing agent. Preferred is sodium borohydride.

The hydride reducing agent is preferably solid and more preferably a crystalline powder which remains solid under the reaction conditions, i.e. is solid at the reaction temperature and not soluble or only slightly soluble in the solvent used for the reaction.

The at least one activator is or contains preferably a metal, alloy, metal complex, or metal salt able to activate the hydride reducing agent or activate the carbonyl group of the artemisinin.

On the one hand, the activator can activate the hydride reducing agent, as the cation or cations of the activator replace(s) the metal cation of hydride reducing agent and/or coordinate(s) with the cation of the hydride reducing agent in order to generate more active hydride anion. For example, lithium borohydride can be prepared in situ by the metathesis reaction of sodium borohydride and lithium bromide or chloride and potassium borohydride and lithium chloride (*Inorg. Chem.* 1981, 20, 4454-4456).

On the other hand, the activator can activate the carbonyl group of the artemisinin, as the cation or cations of the activator coordinate(s) with the oxygen of the carbonyl group and/or one or two neighboring oxygens of the artemisinin in order to increase electrophilicity on the carbonyl group.

Thus the activator is preferably a metal, alloy, metal complex, or metal salt or any other compound having the same function such as iodine, polyaniline salts or propanephosphonic acid cyclic anhydride, wherein the metal cation is the active species which makes the carbonyl group of artemisinin more sensitive to reduction and/or increases the activity of the hydride reducing agent. Thus the activator supports the reduction of the carbonyl group of artemisinin and/or increases velocity of the reduction of the carbonyl group of artemisinin and/or increases the yield of the reduction product which is the dihydroartemisinin and/or activates the hydride reducing agent and/or forms a complex with the hydride anion of the hydride reducing agent and/or increases nucleophilicity of the hydride reducing agent and/or increases electrophilicity of the carbonyl group of artemisinin.

If a compound is suitable as activator can be determined by standard methods such as measurement of the reaction kinetic. For instance, the time until complete conversion of the artemisinin could be measured. If the reaction time until complete conversion of the artemisinin is decreased, the test compound acts as activator in case the yield of dihydroartemisinin is not considerably altered. That means the yield should not differ more than 10% and preferably more than 5% in regard to the reaction without test compound (i.e. without activator) in order to exclude the possibility that the accelerated conversion of artemisinin is caused by rapid decomposition. Thus in case the yield is similar to the yield obtained by the reaction without activator but the time until complete conversion of artemisinin is decreased, the test compound is identified as a suitable activator. Preferably the reaction time until complete conversion of artemisinin should be reduced by at least 10%, more preferably by at least 20% and most preferably by at least 30%.

Examples of activators are alkaline metal halides, alkaline earth metal halides, Li salts, In salts, $I_2$, Ni salts, Ni foam, hydrogels containing Co and/or Ni nanoparticles, nanotubes containing Au nanoparticles, Pb salts, $TiO_2$ containing Pd or Co—Ni—P, polyaniline salts, propanephosphonic acid cyclic anhydride, protein-capped Au nanoparticles, pyridinium based dicationic ionic salts, RU salts, Ru immobilized on $Al_2O_3$ pellets, Ru-activated carbon, $CeCl_3$, Ru—$CeO_2$, Ru—$TiO_2$, Ru-γ $Al_2O_3$, $Ru_{60}Co_{20}Fe_{20}$, Ru-promoted sulphated zirconia, titanyl acetylacetonate, Au nanoparticles, Co salts, Celite® Amberlyst 15, Amberlyst 15 with dextrose or galactose and phloroglucinol. The expression "at least one" activator indicates that also mixtures of activators can be used.

The activator is preferably an inorganic activator. Moreover the activator preferably contains inorganic anions. The activator preferably contains halide counterions ($F^-$, $Cl^-$, $Br^-$, $I^-$), nitrate ($NO_3^-$), sulfate ($SO_4^{2-}$), or phosphate counterions ($PO_4^{3-}$). Thus the activator preferably contains an inorganic counterion or the activator is preferably an inorganic activator.

The activator or inorganic activator is preferably solid and more preferably a crystalline powder which remains solid under the reaction conditions, i.e. is solid at the reaction temperature and not soluble or only slightly soluble in the solvent used for the reaction.

Further preferred activators are LiF, LiCl, LiBr, LiI, $CaCl_2$, $InCl_3$, Ni(bpy)$Cl_2$, $PbF_2$, $PbCl_2$, $PbBr_2$, $PbI_2$, $RuCl_3$, Ru(NO)(NO$_3$)$_3$, $CoCl_2$ and a mixture thereof. More preferred activators are LiF, LiCl, LiBr, LiI and a mixture thereof.

In the method according to the invention the activators have a particle size ranging from 3 to 1000 µm, preferably 10 to 500 µm, more preferably 10 to 200 µm, even more preferably 15 to 200 µm, most preferably from 20 µm to 100 µm.

In a further preferred embodiment of the present invention a filler material is used in addition to the activator, solid base and hydride reducing agent or in addition to the activator and hydride reducing agent and/or in addition to the solid base. Such a filler material is preferably homogenously mixed with the activator, hydride reducing agent and/or solid base and the obtained mixture is filled into the one or two columns. Suitable filler materials are, for instance, $SiO_2$, $Al_2O_3$, $TiO_2$, $Al_2O_3$, ZnO, Celite® ("filter aid," diatomaceous earth, etc.), carbon black, carbon nanotubes, silica gel, polymeric beads, metallic particles (ball bearings), glass particles, teflon particles, ceramic particles and unreactive salt particles. A most preferred mixture of filler material, activator and hydride reducing agent is Celite®, LiCl and $NaBH_4$. Preferably the filler material should be inert, i.e. unreactive under the reaction conditions used for the reduction of artemisinin.

In an embodiment of the present invention, granulated Celite® is used. Celite® is called also as diatomite, or kieselgur/kieselguhr. The chemical composition of used Celite® is 80 to 90%, preferably 85 to 90%, more preferably 88 to 90%, most preferably 89 to 90% silica, with 2 to 4% alumina and 0.5 to 2% iron oxide. The Celite® used in the method according to the invention having a particle size ranging from 3 to 1000 µm, preferably 10 to 500 µm, more preferably 10 to 200 µm, even more preferably 15 to 200 µm, most preferably from 20 µm to 100 µm. Depending on the granularity, this Celite® powder can have an abrasive feel, similar to pumice powder, and is very light as a result of its high porosity. If necessary, Celite® is treated with solid base such as sodium carbonate. In the method according to the present invention, preferably is used Celite® 545 treated with sodium carbonated having pH value in the range from 8 to 11, preferably 8 to 10, more preferably 9 to 10, most preferably 9.5 to 10.

In the method according to the invention, lithium chloride has a particle size ranging from 3 to 1000 µm, preferably 10 to 500 µm, more preferably 10 to 200 µm, even more preferably 15 to 200 µm, most preferably from 20 µm to 100 µm.

The at least one solid base is preferably selected from the group comprising or consisting of: metal hydroxides, metal carbonates, alkaline metal hydroxides, alkaline earth metal hydroxides, $Li_2CO_3$, $Na_2CO_3$, $K_2CO_3$, $CaCO_3$, $MgCO_3$, LiOH, NaOH, KOH, Ca(OH)$_2$, Mg(OH)$_2$, ammonium hydroxide, tetraalkylammonium hydroxides. The expression "at least one" solid base indicates that also mixtures of solid bases could be used. The solid base can be applied for neutralizing the artemisinin solution provided after steps A) and B), because the artemisinin solution resulting from steps A) and B) is acidic.

It was found that a preferred molar ratio of solid base to the hydride reducing agent is in the range of 1.0:0.5 to 1.0:10.0, more preferred 1.0:0.5 to 1.0:5.0, even more preferred 1.0:0.5 to 1.0:3.0, and most preferred 1.0:0.5 to 1.0:1.0.

In another embodiment of the present invention, the continuous flow reactor comprises preferred a column filled with a mixture of sodium borohydride, Celite®, $Li_2CO_3$ and LiCl in a ratio of 1.0:1.0:1.0:0.7 (w/w).

The continuous method for reducing artemisinin involves a continuous flow of a solution of artemisinin in at least one aprotic solvent containing at least one $C_1$-$C_5$ alcohol through the column containing the hydride reducing agent, the at least one activator and the at least one solid base (one column embodiment) or through the first column containing the at least one solid base and the second column containing the hydride reducing agent and the at least one activator (two column embodiment).

Examples for aprotic solvents are: $CH_2Cl_2$, $CHCl_3$, $ClH_2CCH_2Cl$, $CHCl_2CHCl_2$, $CCl_2FCCl_2F$, $CH_3CN$, $Et_2O$, ter-butylmethylether (MTBE), 1,2-dimethoxyethane, pentane, hexane, heptanes, petroleum ether, cyclopentane, cyclohexane, benzene, toluene, PEG 400, THF, 1,3-dioxane, 1,4-dioxane, dimethylformamide, dimethylacetamide, N-methyl pyrrolidinone (NMP) and mixtures thereof. It was found that a preferred aprotic solvent is THF.

The expression "at least one" aprotic solvent indicates that also mixtures of aprotic solvents could be used.

The term "$C_1$-$C_5$ alcohol" refers to any monool, diol, triol, tetraol or pentaol. Preferred examples of a $C_1$-$C_5$ alcohol are:

CH$_3$OH, CH$_3$CH$_2$OH, CH$_3$CH$_2$CH$_2$OH, CH$_3$CH$_2$CH$_2$CH$_2$OH, CH$_3$CH$_2$CH$_2$CH$_2$CH$_2$OH, HOCH$_2$CH$_2$OH, HOCH$_2$CH$_2$CH$_2$OH, HOCH$_2$CH$_2$CH$_2$CH$_2$OH, HOCH$_2$CH$_2$CH$_2$CH$_2$CH$_2$OH, HOCH$_2$CH(OH)CH$_2$OH, HOCH$_2$CH(OH)CH$_2$CH$_2$OH, HOCH$_2$CH(OH)CH(OH)CH$_3$, HOCH$_2$CH(OH)CH(OH)CH$_2$OH, HOCH$_2$CH(OH)CH$_2$CH$_2$CH$_2$OH, HOCH$_2$CH$_2$CH(OH)CH$_2$CH$_2$OH, HOCH$_2$CH(OH)CH(OH)CH$_2$CH$_2$OH, HOCH$_2$CH(OH)CH$_2$CH(OH)CH$_2$OH, HOCH$_2$CH(OH)CH(OH)CH(OH)CH$_2$OH, HC(CH$_2$OH)$_3$, HO—C(CH$_2$OH)$_3$, and C(CH$_2$OH)$_4$.

It was found that a preferred molar ratio of C$_1$-C$_5$ alcohol to hydride reducing agent is in the range of 1.0:0.1 to 1.0:10.0, more preferred 1.0:0.3 to 1.0:5.0, even more preferred 1.0:0.4 to 1.0:3.0, and most preferred 1.0:0.5 to 1.0:1.0. It was also found that a preferred C$_1$-C$_5$ alcohol is methanol, ethanol and a mixture thereof.

In the step 2), the continuous flow of the solution of the artemisinin provided has preferably a flow rate in the range from 0.1 to 10.0 mL/min, more preferably from 0.1 to 5.0 mL/min, even more preferably from 0.1 to 3.0 mL/min, yet even more preferably from 0.1 to 1.0 mL/min, most preferably from 0.1 to 0.5 mL/min The reduction steps 1), 2), and 3) are preferably performed at a temperature in the range from 0° C. to 60° C. In addition also the derivatization step 4) is carried out at a temperature in the range from 0° C. to 60° C.

In the step 4) the conversion of the dihydroartemisinin (4) obtained from step 3) to an artemisinin derivative (5) can be carried out as follows:

iv) preparing a solution of at least two reactants for converting the dihydroartemisinin in a solvent,
v) mixing the dihydroartemisinin (4) obtained from step 3) and the solution of the acid and the at least two reactants
vi) maintaining the reaction mixture for a residence time at an appropriate temperature.

In an embodiment, dihydroartemisinin (4) can be etherified. In this case, the at least two reactants comprise at least one acid catalyst, an alcohol (ROH) and a trialkoxyorthoformate (CH(RO)$_3$) wherein the alcohol (ROH) can be also used as the solvent.

The at least one acid catalyst is selected from the group consisting of HCl, HBr, H$_2$SO$_4$, H$_3$PO$_4$, HClO$_4$, CF$_3$CO$_2$H, p-TolSO$_3$H, MeSO$_3$H, AlCl$_3$, BF$_3$, TMSOTf, TMSCl and a mixture thereof. The acid catalyst as used herein refers to a Lewis acid which produces oxonium ion from lactal group of dihydroartemisinin by dehydration reaction or other elimination reactions of hydroxyl group from lactal group. The concentration of the acid is in the range preferably from 1 to 20 mM, more preferably from 1 to 10 mM, most preferably from 1 to 5 mM. The molar (or w/w) ratio of dihydroartemisinin to acid catalyst is preferably in the range from 1.0:0.01 to 1.0:1.0, more preferably from 1.0:0.01 to 1.0:0.5, most preferably from 1.0:0.01 to 1.0:0.2.

The alcohol (ROH) is selected from the group consisting of alkyl alcohol, halogenalkyl alcohol, hydroxyalkyl alcohol, alkoxyalkyl alcohol, carboxyalkyl alcohol, aryl alcohol, alkylaryl alcohol, alkoxyaryl alcohol, arylalkyl alcohol, arylalkoxyalkyl alcohol, alkylarylalkyl alcohol, alkylarylalkoxyalkyl alcohol, alkenyl alcohol, alkynyl alcohol, cycloalkyl alcohol, alkylcycloalkyl alcohol, alkoxyalkylcycloalkyl alcohol, cycloalkylalkyl alcohol, cycloalkylalkoxyalkyl alcohol, heterocyclyl alcohol, alkoxycarbonylalkyl alcohol, acyloxyalkyl alcohol, heterocyclylalkyl alcohol, alkylcarbonylaminoalkyl alcohol, alkoxycarbonylaminoalkyl alcohol, aminoalkyl alcohol, alkylaminoalkyl alcohol, dialkylaminoalkyl alcohol, alkylaminocarbonylalkyl alcohol, and dialkylaminocarbonylalkyl alcohol.

More preferably, the alcohol is selected from the group consisting of CH$_3$OH, CH$_3$CH$_2$OH, CH$_3$CH$_2$CH$_2$OH, (CH$_3$)$_2$CHOH, CH$_3$CH$_2$CH$_2$CH$_2$OH, CH$_3$CH$_2$CH$_2$CH$_2$CH$_2$OH, HOCH$_2$CH$_2$OH, HOCH$_2$CH$_2$CH$_2$OH, HOCH$_2$CH$_2$CH$_2$CH$_2$OH, HOCH$_2$CH$_2$CH$_2$CH$_2$CH$_2$OH, cyclo-C$_3$H$_5$CH$_2$OH, cyclo-C$_3$H$_5$CH$_2$CH$_2$OH, cyclo-C$_4$H$_7$CH$_2$OH, cyclo-C$_4$H$_7$CH$_2$CH$_2$OH, cyclo-C$_5$H$_9$CH$_2$OH, cyclo-C$_5$H$_9$CH$_2$CH$_2$OH, cyclo-C$_6$H$_{11}$CH$_2$OH, cyclo-C$_6$H$_{11}$CH$_2$CH$_2$OH, PhOH, PhCH$_2$OH, 4-(OH)-PhCH$_2$OH, 4-(CO$_2$H)-PhCH$_2$OH, PhCH$_2$CH$_2$OH.

In an embodiment of the present invention, the trialkoxyorthoformate (CH(RO)$_3$) can be used optionally and has the alkoxy group (RO) corresponding to the used alcohol (ROH). In the present invention, the R group of trialkoxyorthoformate (CH(RO)$_3$) is selected from the group consisting of alkyl, halogenalkyl, hydroxyalkyl, alkoxyalkyl, carboxyalkyl, aryl, alkylaryl, alkoxyaryl, arylalkyl, arylalkoxyalkyl, alkylarylalkyl, alkylarylalkoxyalkyl, alkenyl, alkynyl, cycloalkyl, alkylcycloalkyl, alkoxyalkylcycloalkyl, cycloalkylalkyl, cycloalkylalkoxyalkyl, heterocyclyl, alkoxycarbonylalkyl, acyloxyalkyl, heterocyclylalkyl, alkylcarbonylaminoalkyl, alkoxycarbonylaminoalkyl, aminoalkyl, alkylaminoalkyl, dialkylaminoalkyl, alkylaminocarbonylalkyl, and dialkylaminocarbonylalkyl.

Preferably, the R group of trialkoxyorthoformate (CH(RO)$_3$) is selected from the group consisting of H$_3$C—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH$_2$CH$_2$CH$_2$—, cyclo-C$_3$H$_5$CH$_2$—, cyclo-C$_3$H$_5$CH$_2$CH$_2$—, cyclo-C$_4$H$_7$CH$_2$—, cyclo-C$_4$H$_7$CH$_2$CH$_2$—, cyclo-C$_5$H$_9$CH$_2$—, cyclo-C$_5$H$_9$CH$_2$CH$_2$—, cyclo-C$_6$H$_{11}$CH$_2$—, cyclo-C$_6$H$_{11}$CH$_2$CH$_2$—, Ph-, PhCH$_2$—, 4-(OH)-PhCH$_2$—, 4-(CO$_2$H)-PhCH$_2$—, PhCH$_2$CH$_2$—.

The volume (v/v) ratio of the alcohol (ROH) to the corresponding trialkoxyorthoformate (CH(RO)$_3$) is preferably in the range from 1.0:1.0 to 10.0:1.0, more preferably from 1.0:1.0 to 5.0:1.0, even more preferably from 1.0:1.0 to 3.0:1.0, most preferably from 1.5:1.0 to 2.5:1.0.

In an embodiment of the present invention, an aprotic solvent can be used optionally. The aprotic solvent is selected from the group consisting of CH$_2$Cl$_2$, CHCl$_3$, ClH$_2$CCH$_2$Cl, CHCl$_2$CHCl$_2$, CCl$_2$FCCl$_2$F, CH$_3$CN, Et$_2$O, ter-butylmethylether (MTBE), 1,2-dimethoxyethane, pentane, hexane, heptanes, petroleum ether, cyclopentane, cyclohexane, ethyl acetate, methyl acetate, acetone, benzene, toluene, PEG 400, THF, 1,3-dioxane, 1,4-dioxane, dimethylformamide, dimethylacetamide, N-methyl pyrrolidinone (NMP) and mixtures thereof.

In an embodiment of the present invention, the etherification reaction is carried out in the temperature in the range preferably from 0 to 80° C., more preferably from 0 to 60° C., most preferably from 10 to 50° C.

The residence time is preferably, 10-60 min, more preferably 10-40 min, even more preferably 15-30 min and most preferably 20-30 min.

In an embodiment of the present invention, the solution of at least two reactants for converting the dihydroartemisinin in the solvent and the solution of the dihydroartemisinin is mixed via T-mixer.

The yield of artemisinin ether derivative from artemisinin (or dihydroartemisinin) is in the range from 20 to 80% with the purity of preferably at least 90%, more preferably at least 95%, most preferably at least 97%.

The ratio of β:α epimers of artemisinin ether derivatives is in the range from 50:50 to 90:10, preferably from 60:40 to 90:10, more preferably from 70:30 to 90:10, most preferably from 75:25 to 85:15.

In another embodiment of the present invention, artemisinin ester derivatives can be produced by esterification of dihydroartemisinin (4). In this case, the solution of the at least two reactants comprise at least one base catalyst and an activated carbonyl reagent in an aprotic solvent.

The abovementioned aprotic solvent is also selected for the esterification of dihydroartemisinin (4).

The at least one base catalyst is selected from the group consisting of $(CH_3)_3N$, $(CH_3CH_2)_3N$, DIPEA (N,N-Diisopropylethylamine), pyridine, DMAP(4-(Dimethylamino)pyridine), DBN (1,5-diazabicyclo[4.3.0]non-5-ene), DBU (1,8-diazabicyclo[5.4.0]undec-7-ene), imidazole, N—($C_1$-$C_3$-alkyl)imidazole and a mixture thereof. Herein, $C_1$-$C_3$ alkyl is —$CH_3$, —$CH_2CH_3$, —$CH_2CH_2CH_3$, —$CH(CH_3)_2$.

The concentration of the base catalysis is in the range preferably from 0.01 to 20 M, more preferably from 0.1 to 10 M, most preferably from 0.5 to 3 M.

The activated carbonyl reagent is selected from the group consisting of a cyclic or acyclic anhydride, an acid halide (chloride, bromide, fluoride). Activated carbonyl reagent can be also prepared by using the conventional carboxylic acid activators such as thionylchloride, $PCl_5$, carbodiimides, hydroxy triazoles, triazines, N-ethoxycarbonyl-2-ethoxy-1,2-dihydroquinoline (EEDQ), and 5-(pentafluorophenyloxy)-3,4-dihydro-1-methyl-2H-pyrrolium hexachloroantimonate (FOMP).

An activated carbonyl reagent can be prepared from a carboxylic acid (R—$CO_2H$). The carboxylic acid (R—$CO_2H$) is selected from the group consisting of alkyl carboxylic acid, halogenalkyl carboxylic acid, hydroxyalkyl carboxylic acid, alkoxyalkyl carboxylic acid, carboxyalkyl carboxylic acid, aryl carboxylic acid, alkylaryl carboxylic acid, alkoxyaryl carboxylic acid, arylalkyl carboxylic acid, arylalkoxyalkyl carboxylic acid, alkylarylalkyl carboxylic acid, alkylarylalkoxyalkyl carboxylic acid, alkenyl carboxylic acid, alkynyl carboxylic acid, cycloalkyl carboxylic acid, alkylcycloalkyl carboxylic acid, alkoxyalkylcycloalkyl carboxylic acid, cycloalkylalkyl carboxylic acid, cycloalkylalkoxyalkyl carboxylic acid, heterocyclyl carboxylic acid, alkoxycarbonylalkyl carboxylic acid, acyloxyalkyl carboxylic acid, heterocyclylalkyl carboxylic acid, alkylcarbonylaminoalkyl carboxylic acid, alkoxycarbonylaminoalkyl carboxylic acid, aminoalkyl carboxylic acid, alkylaminoalkyl carboxylic acid, dialkylaminoalkyl carboxylic acid, alkylaminocarbonylalkyl carboxylic acid, and dialkylaminocarbonylalkyl carboxylic acid.

Also preferred, the activated carbonyl reagent is an acylhalide such as acylchlorides, and acylfluorides, an anhydride or mixed anhydride such as succinic anhydride, glutaric anhydride, succinic acid monomethyl ester, monomethyl malonate or a specialized actived carbonyl species such as acyl pyridiniums and acyl hydro-azabenzotriazoles, and the like.

The molar ratio of dihydroartemisinin to an activated carbonyl reagent is preferably in the range from 1.0:1.0 to 1.0:5.0, more preferably from 1.0:1.0 to 1.0:3.0, most preferably from 1.0:1.5 to 1.0:2.0.

The molar ratio of the base catalyst to an activated carbonyl reagent is preferably in the range from 0.5:1.0 to 0.5:5.0, more preferably from 0.5:1.0 to 0.5:3.0, most preferably from 1.0:1.0 to 1.0:2.0.

In yet another embodiment, the dihydroartemisinin can be further converted to sulfonate, carbonate, carbamate and thiocarbamate derivatives, wherein R is derived respectively from sulfonyl chloride, chloro formate, isocyanate and isothiocyanate. Similar with the above-described esterification, at least one basic catalyst is necessary and the converting reaction of dihydroartemisinin is preferred carried out in one of the said aprotic solvents.

Further embodiment of the present invention is the method, wherein 6.5 mmol artemisinin per mL column volume are processed in a total residence time below 20 minutes through the continuous flow reactor in order to yield at least 90% artemisinin derivatives of a purity above 95%.

In another embodiment of the present invention is abovementioned method for continuously reducing artemisinin further comprising the following steps A) and B) before step 1):
A) providing dihydroartemisinic acid represented by the following formula

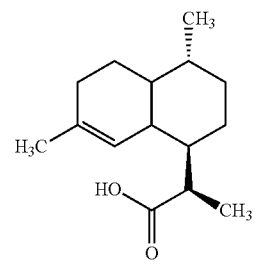

2

B) performing the following reactions
  i) photooxidation of dihydroartemisinic acid with singlet oxygen,
  ii) followed by an acid mediated cleavage, and
  iii) subsequent oxidation with triplet oxygen
  in order to obtain artemisinin of the following formula:

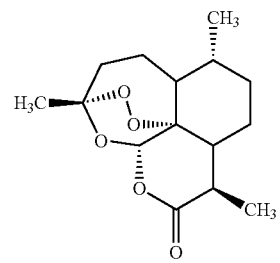

3

In the step i) of step B), the photooxidation of dihydroartemisinic acid (2) with singlet oxygen is carried out. The photooxidation of dihydroartemisinic acid (2) generally results in the intermediate products (2a), (2b) and (2c) as also described in example 1. The main intermediate product is the hydroperoxide (2a) which can be obtained by the process of the present invention in at least 75% yield, preferably in at least 80% yield and more preferably in at least 84% yield. In order to perform subsequent reactions such as the further preparation of artemisinin (3), preferably also in a continuous manner, it is not required to purify the obtained hydroperoxide (2a) or to remove the intermediate products (2b) and (2c) as shown in example 1.

The hydroperoxide (2a) of the following formula

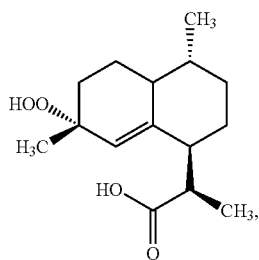

the hydroperoxide (2b) of the following formula

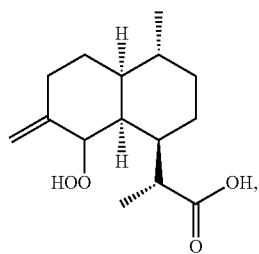

and the hydroperoxide (2c) of the following formula

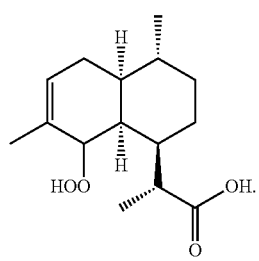

are formed as photooxidation products from the reaction of dihydroartemisinic acid (2) with singlet oxygen according to the present invention.

As also described above, dihydroartemisinic acid (2) can be prepared from artemisinic acid (1) of the following formula:

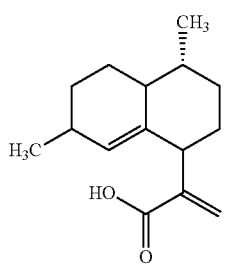

(1)

The starting material artemisinic acid (1) which is also known as arteannuic acid and which has the chemical name 2-[(1R,4R,4aS,8aR)-4,7-dimethyl-1,2,3,4,4a,5,6,8a-octahydronaphthalen-1-yl]prop-2-enoic acid can be obtained synthetically, by recombinant methods or can be isolated from the plant *Artemisia annua*. Since there is artemisinic acid and dihydroartemisinic acid contained in the plant *Artemisia annua*, an efficient method to convert artemisinic acid (1) and dihydroartemisinic acid (2) into the hydroperoxide (2a) and subsequently to artemisinin (3) is desired. Thus the starting material artemisinic acid (1) or dihydroartemisinic acid (2) can be used as a plant extract in all reactor embodiments disclosed herein. Also, extraction protocols to remove artemisinic acid and dihydroartemisinic acid from *artemisia annua* have been published (Wallaart, T. E. et al., J. Nat. Prod. 1999, 62, 430-433), making use of the extraction of acidic compounds by aqueous base and the reextraction into an organic phase after acidification.

An adapted procedure can be applied to such mother liquor remaining after removal of artemisinin from *artemisia annua* extracts. Thus, also the extract of *artemisia annua* after the removal of artemisinin can be readily used as starting material in all reactor embodiments disclosed herein. Therein the method of the present invention provides a possibility of sophistically using waste material of industrial scale.

Also, in order to overcome drawbacks of photochemical reactions being performed in batch-like manner in the prior art, the inventors designed a continuous flow set-up which in contrast to said batch processes allows the production of large quantities of desired material by simply extending the run time rather than changing to larger reaction vessels. The continuous flow process of the present invention provides a highly complex natural product from a much less complex molecule that can be isolated in larger quantities or can be readily produced in yeast. The efficiency, simplicity and productivity of the approach will provide access to much needed medication against malaria.

In the steps ii) and iii) of step B), the cleavage of the said hydroperoxide intermediate product (2a) and subsequent oxidation of cleavage intermediate with triplet oxygen is carried out in the reactor (8 in FIG. 6). For the cleavage of the hydroperoxide intermediate product (2a), a solution of TFA is added into the intermediate solution at a flow rate in the range of 0.1 to 5.0 mL/min, preferably from 0.1 to 2.0 mL/min, more preferably from 0.5 to 1.5 mL/min, most preferably 1.0 to 1.3 mL/min via a mixer. The reaction mixture is then passed a reactor (8 in FIG. 6) for producing the artemisin (3).

The methods of the present invention allow the synthesis of artemisinin, wherein 12.5 mmol dihydroartemisinic acid (2) are processed in a total residence time below 15 minutes through the photooxidation reactor (7 in FIG. 6) and the subsequent reactor (8 in FIG. 6) in order to yield preferably at least 65% artemisinin (3) of a purity above 95%.

Excellent control over reaction parameters such as reaction time, temperature and mixing are hallmarks of flow chemistry and thus also provided by the method, the photochemical reactor and the continuous flow reactor according to the present invention. Photochemical transformations according to the present invention greatly benefit from the flow regime as the penetration depth of the light remains almost the same also during scale-up due to the dimensions of tubing that serves as reaction vessel.

Thus, the significant disadvantages of the prior art were addressed by the present invention and were solved in a way that at least the photooxidation of dihydroartemisinic acid (2), but also subsequent steps starting from dihydroartemisinic acid (2) could be combined in a continuous flow system which can be easily controlled, easily scaled up, optimized to produce good yields and does not require the isolation and purification of any intermediates. Such advantages cannot be provided by a batch-reaction of dihydroartemisinic acid (2) with singlet oxygen, and also optional subsequent continuous conversions to yield artemisinin (3) as described herein.

Optionally, the above-mentioned methods can comprise further a continuous separation step C) of artemisinin derivative (5) which is followed by step 4). A raw product of artemisinin derivative (5) can be separated by usual techniques such as extraction, crystallization or column chromatography. However it is also possible to implement the separation step into continuous flow reactor design of the present invention. Herein the two subsequent methods are preferred:

C1) separation by simulated moving bed chromatography,
C2) separation by continuous crystallization.

Continuous chromatography methods, in particularly simulated moving bed chromatography (SMB chromatography) comprises an arrangement of several columns with two inlet and outlet connections respectively, which are moved in such a fashion to mimic a counter flow of the stationary phase compared to the eluent flow. This enables continuous binary separations in which either the least or the strongest absorbing component can be extracted as pure compound. Also, this method is readily scalable and can be employed for purification on large scale without extensive consumption of solvents.

In the continuous crystallization process, a saturated solution of the crude in a suitable solvent is prepared at elevated temperatures. Cooling while flowing through a tube creates an oversaturated solution, from which upon seeding artemisinin crystallizes onto the surface of the tube. These crystals can be removed from the mixture continuously. Accordingly, the crude mixture containing artemisinin derivative (5) after reaction of dihydroartemisinin and the crude solution is exposed to elevated temperatures, preferably under reduced pressure for removal of solvent. Once a sufficient amount of solvent is removed, and a saturated or almost saturated solution of artemisinin derivative (5) is prepared the solution is led to a further component of the reactor where decreased temperature is applied to the solution. Preferably, not only the temperature is decreased but also crystalline artemisinin seeds are provided. Upon these conditions an oversaturated solution develops out of which crystalline artemisinin will precipitate which can be separated, e.g. by filtration from the crude reaction mixture.

Continuous Flow Reactor

The present invention is also directed to a continuous flow reactor (6) for the continuous production and reduction of artemisinin comprising:
a photochemical reactor (7) for performing the photooxidation of dihydroartemisinic acid with singlet oxygen in a continuous manner,
a reactor (8) for performing an acid mediated cleavage of the photooxidation product and the subsequent oxidation with triplet oxygen in order to obtain artemisinin,
a column (9) containing a hydride reducing agent, at least one activator and at least one solid base or a first column (10A) containing at least one solid base and a second column (10B) containing a hydride reducing agent and at least one activator in order to obtain dihydroartemisinin.

Preferably the continuous flow reactor (6) of the present invention comprises in addition
a reactor (12) for converting dihydroartemisinin to the artemisinin derivative of the following formula

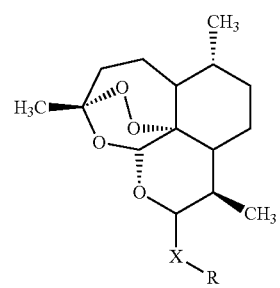

In the continuous flow reactor (6) according to the present invention at least the photooxidation of dihydroartemisinic acid (2) with singlet oxygen is performed in a continuous manner, while an acid mediated cleavage (step ii)) and subsequent oxidation with triplet oxygen (step iii)) may also be performed in a semi-batch manner or in a batch reactor. Thus at least the photooxidation in the photochemical reactor is performed continuously which means in a continuous manner as defined above, while the acid mediated cleavage (step ii)) and the oxidation with triplet oxygen (step iii)) do not necessarily have to be conducted in a continuous manner. However it is preferred that also step ii), namely the acid mediated cleavage and more preferred the acid mediated cleavage and step iii), namely the oxidation with triplet oxygen are conducted also in a continuous manner. The continuous manner of step ii) and step iii) can be different from the continuous manner of step i). This means that different flow rates are normally used for the steps i), ii) and iii). Step ii) can normally be processed with the highest flow rate while step i) normally has the lowest flow rate of all three steps. However it is most preferred that steps i) and ii) and iii) are performed in a continuous manner. Thus it is preferred that steps A), B), 1), 2) and 3) are performed continuously or in a continuous manner. Performing step 1) in a continuous manner means that the column (9) or the columns (10A) and (10B) are prepared and provided once and used continuously for performing the reduction of artemisinin (3) until the hydride reducing agent is used up or is used up to a degree that the yield of dihydroartemisinin (4) starts decreasing so that the column (9) or the column (10B) has to be replaced by a column containing new hydride reducing agent. Much less often than column (10B) also the column (10A) needs to be replaces by a column with fresh solid base.

Therefore, the continuous flow reactor (6) of the present invention comprises a photochemical reactor (7), wherein the conversion of dihydroartemisinic acid (2) with singlet oxygen takes place continuously, i.e. in a continuous manner.

The photochemical reactor (7) used herein for the synthesis of artemisinin is disclosed in WO2013030247A1 which is an earlier application of the present inventors. Moreover a continuous flow reactor without the column (9) or without the columns (10A) and (10B) is also disclosed in WO2013030247A1. Thus the disclosure of WO2013030247A1 from page 7, last paragraph to the last line on page 31 and especially from page 10, line 5 to the last line on page 31 is hereby incorporated by reference. This disclosure is directed to the continuous flow reactor. The continuous flow reactor (7) of the present invention differs from the continuous flow reactor disclosed in WO2013030247A1 by the presence of the additional column (9) or the additional columns (10A) and (10B) and optionally the reactor (12).

As the photochemical reactor (7) is comprised by the continuous flow reactor (6) of the present invention every modification as being described below for the photochemical reactor (7) also applies to the continuous flow reactor (6).

The photochemical reactor (7) for performing the photooxidation of dihydroartemisinic acid (2) with singlet oxygen in a continuous manner comprises or consists of
  a light source (11),
  mixing device for mixing oxygen with a solution of dihydroartemisinic acid,
  reactor compartment exposed to the light source for irradiating the mixture of the solution of dihydroartemisinic acid and oxygen when the mixture passes the reactor compartment.

An alternative embodiment of the photochemical reactor for performing the photooxidation of dihydroartemisinic acid (2) with singlet oxygen in a continuous manner comprises or consists of
  a light source (11),
  mixing device for mixing oxygen with a solution of dihydroartemisinic acid,
  reactor compartment for carrying out the photooxidation and which is at least partially irradiated by the light source and which has at least one inlet for the solution of dihydroartemisinic acid and oxygen and at least one outlet for the solution after the photooxidation.

Suitable embodiments of photochemical reactors (7) are also disclosed in detail in WO2013030247A1. The disclosure of WO2013030247A1 from page 10, line 9 to the last line on page 12 is hereby incorporated by reference. This disclosure is directed to the photochemical reactor.

In general, a reactor component as used herein refers to a section of the continuous flow reactor, from the feed of a certain starting material to the outlet of product, wherein certain actions or operations for the conversion of dihydroartemisinic acid (2) to artemisinin (6) take place and comprise all reactor parts which are involved in these actions or operations. The reactor compartment is therefore a specific form of a reactor component. If the continuous flow reactor is seen as a long sequence of different reactor parts which the starting materials alone or in a mixture pass along, section can almost be taken literally in that certain parts are figuratively cut out of the sequence and defined by their function to the reaction.

For example, reactor components of the continuous flow reactor of the present invention are reactor parts for the following actions:
  provision of the starting materials,
  mixing of the starting materials,
  irradiation of a solution of dihydroartemisinic acid, sensitizer, solvent and oxygen,
  mixing with acid,
  reaction of the acid for the Hock cleavage,
  oxidation with triplet oxygen for the formation of artemisinin.

According to the present invention a reactor component may comprise the physical reactor parts for more than one function for enabling the different reactions for the conversion of dihydroartemisinic acid (2) to artemisinin (3). One reactor component may only comprise these parts of the continuous flow reactor of the present invention where the Hock cleavage takes place. However, another reactor component may comprise all parts where the conversions take place that the material flow undergoes after the irradiation of the light source.

The reactor component of the continuous flow reactor for performing the photooxidation reaction is the reactor compartment with all reactor parts that are irradiated by the light source and having an inlet for the mixture of dihydroartemisinic acid and oxygen on its one end and an outlet for the reacted products on the opposite end. It is also possible that the photochemical reactor as defined herein with all different possible specifications may be a reactor compartment of the continuous flow reactor of the present invention.

Thus the term "reactor compartment" refers to the reactor parts that are irradiated by the light source. Within the reactor compartment the photooxidation reaction with singlet oxygen is performed under irradiation by the light source. Thus the mixture of solvent, dihydroartemisinic acid (2), photosensitizer and oxygen flows through the reactor compartment wherein the photooxidation reaction with singlet oxygen [step i)] is performed. The reactor compartment through which the mixture flows which is exposed to the light of the light source has the form of a tube, coil, cylinder, double-wall cylinder, multi-walled cylinder, tubing, duct, pipe, spiral, helix, spiral coil, zig-zag coil, board, fluidized bed, multi-layered fluidized bed, pool, vessel, tank, basin or the like. The reactor compartment has a form so that the mixture to be irradiated which flows through the reactor compartment is almost all the time exposed to the light of the light source when flowing through the reactor compartment.

A preferred embodiment of the present invention is directed to a continuous flow reactor (6) for the continuous production and reduction of artemisinin comprising:
  a photochemical reactor (7) for performing the photooxidation of dihydroartemisinic acid with singlet oxygen in a continuous manner, and
  a reactor (8) for performing an acid mediated cleavage of the photooxidation product and the subsequent oxidation with triplet oxygen in order to obtain artemisinin, and
  a column (9) containing a hydride reducing agent, at least one activator and at least one solid base or a first column (10A) containing at least one solid base and a second column (10B) containing a hydride reducing agent and at least one activator in order to obtain dihydroartemisinin, and
  a reactor (12) for converting dihydroartemisinin to the artemisinin derivative of the general formula (5) as defined herein.

Thus a preferred embodiment of the present invention is directed to a continuous flow reactor (6) for the continuous production and reduction of artemisinin comprising:
  a photochemical reactor (7) for performing the photooxidation of dihydroartemisinic acid with singlet oxygen in a continuous manner, wherein that photochemical reactor (7) comprises:
    a light source (11), and
    a mixing device for mixing oxygen with a solution of dihydroartemisinic acid, and
    a reactor compartment exposed to the light source for irradiating the mixture of the solution of dihydroartemisinic acid and oxygen, and
  a reactor (8) for performing an acid mediated cleavage of the photooxidation product and the subsequent oxidation with triplet oxygen in order to obtain artemisinin, and a column (9) containing a hydride reducing agent, at least one activator and at least one solid base or a first column (10A) containing at least one solid base and a second column (10B) containing a hydride reducing agent and at least one activator in order to obtain dihydroartemisinin, and a reactor (12) for converting dihydroartemisinin to the artemisinin derivative of the general formula (5) as defined herein.

Thus the inventive continuous flow reactor (6) comprising a column configured and/or adapted to perform the reduction of artemisinin (3) to dihydroartemisinin (4) in a continuous manner.

The continuous flow reactor (6) of the present invention comprises the reactor (8) for performing an acid mediated cleavage of the photooxidation product and the subsequent oxidation with triplet oxygen in order to obtain artemisinin. The reactor (8) has the form of a tube, coil, cylinder, double-wall cylinder, multi-walled cylinder, tubing, duct, pipe, spiral, helix, spiral coil, zig-zag coil, board, fluidized bed, multi-layered fluidized bed, pool, vessel, tank, basin or the like. Thus, the reactor (8) can be heated by a heater or be cooled by a cooler. The heater is configured and adapted to heat the reactor at the temperature in the range from 20° C. to 150° C., preferably from 20° C. to 100° C., more preferably 20° C. to 80° C., most preferably 20° C. to 50° C. The cooler is configured and adapted to cool the reactor at the temperature in the range from −70° C. to +20° C., preferably from −70° C. to 0° C., more preferably −70° C. to −20° C., most preferably −30° C. to −10° C. In the present invention, the reactor for performing an acid mediated cleavage of the photooxidation product and the subsequent oxidation with triplet oxygen is characterized in that the reactor (8) is cooled at the temperature in the range from 15° C. to 25° C.

The continuous flow reactor (6) of the present invention comprises the column (9) containing a hydride reducing agent, at least one activator and at least one solid base or instead of column (9) the first column (10A) containing at least one solid base and the second column (10B) containing a hydride reducing agent and at least one activator in order to obtain dihydroartemisinin.

Preferably the columns (9, 10A, 10B) comprise or consist of a glass or Teflon column, at least one fixed endpiece, two frits, an O-ring, a retaining nut, an adjusting nut, two connection cap, and filling materials. Preferably the frit has the pore size in the range from 10 to 100 μm, more preferably 15 to 75 μm, most preferably from 20 to 40 μm. The filling materials consist preferably of hydride reducing agent, at least one activator and at least one solid base. Example for suitable columns is Omni-Fit® 6.6 mm (Diba Industries Ltd.).

In an especially preferred embodiment of the present invention, the continuous flow reactor (6) comprises the column (9) containing a hydride reducing agent, at least one activator and at least one solid base preferably in a homogenous mixture of powdered compounds. Suitable hydride reducing agents, activators as well as suitable solid bases are disclosed above.

There are several acceptable methods how to pack said columns (9, 10A, 10B). These include dry packing and the slurry method. For the first dry pack method, the column is filled with a solvent. Then, slowly add the filling materials while gently tapping the side of the column. The solid should "float" to the bottom of the column. For the second dry pack method, the filling materials are deposited in the column before the solvent. In this case fill the column to the intended height with the filling materials and then add the solvent. For the third dry pack method, the filling materials are deposited in the column and pressed by air or nitrogen pressure with the pressure range from 1 to 5 bar.

The slurry method can be also used for packing the columns. Firstly, the filling materials are combined with a small amount of a solvent in a beaker. The filling materials and the solvent are mixed thoroughly until a consistent paste is formed, but is still capable of flowing. This homogeneous mixture is poured into the column.

Herein, a non-polar solvent can be used as the solvent for packing the column. The non-polar solvent is preferred selected from the group consisting of pentane, hexane, petroleum ether, cyclopentane and cyclohexane.

However it belongs to the general skill of a skilled person to pack the column (9, 10A, 10B), to derivatize the dihydroartemisinin (4), to perform the photooxidation of dihydroartemisinic acid with singlet oxygen or to use gases such as oxygen as reaction components.

In one embodiment of the present invention, the column (9) can be packed with the filling materials, i.e. the mixture of the hydride reducing agent, the at least one solid base and the at least one solid base by means of the one of said packing methods.

In one embodiment of the present invention, the column (9) can be packed in such a manner: firstly, the column is packed with a mixture of the hydride reducing agent and the at least one activator to 70-90% of the total volume of the column and the rest (10-30%) of the volume of the column is packed with the at least one solid base. For this the dry packing method is preferably used. As result, the first packing area of the column is filled with the at least one base, so that the artemisinin solution can be neutralized in the first packing area consisting of the at least one base. In the second packing area consisting of the hydride reducing agent and the at least one activator, the artemisinin can be reduced to the dihydroartemisinin.

In another embodiment of the present invention, the continuous flow reactor comprises the first column (10A) containing at least one solid base and the second column (10B) containing a hydride reducing agent and at least one activator in order to obtain dihydroartemisinin (FIG. 4). The first column (10A) is filled only with the at least one solid base by means of said packing methods. The second column (10B) is filled with a mixture of the hydride reducing agent and the at least one activator by means of said packing methods. In this case, the artemisinin solution is neutralized in the first column (10A) and reduced to dihydroartemisinin in the second column.

In the present invention, each of the columns (9, 10A, 10B) can further comprise a cooler. The cooler is configured and adapted to cool the column at the temperature in the range from −70° C. to +30° C., preferably from −40° C. to +30° C., more preferably 0° C. to +30° C., most preferably +10° C. to +30° C.

A further embodiment of the present invention is the continuous flow reactor (6) comprising the column (9) filled with a mixture of at least sodium borohydride, Celite®, an activator and an solid base.

Still a further embodiment of the present invention relates to the continuous flow reactor (6) comprising the column (9) filled with a mixture of at least sodium borohydride, Celite®, the activator and the solid base with a ratio of 1:1:1:0.7 (27%: 27%: 27%: 19%) (w/w) of sodium borohydride:Celite®:the activator:the solid base.

An especially preferred embodiment is directed to a continuous flow reactor (6) comprising a reactor (12) for continuously converting dihydroartemisinin to the artemisinin derivative of the general formula (5)

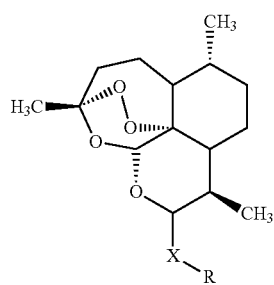

wherein X and R have the meanings as disclosed herein.

The reactor (12) has the form of a tube, coil, cylinder, double-wall cylinder, multi-walled cylinder, tubing, duct, pipe, spiral, helix, spiral coil, zig-zag coil, board, fluidized bed, multi-layered fluidized bed, pool, vessel, tank, basin or the like. In the present invention, the reactor (12) has a heater and/or a cooler. Thus, the reactor (12) can be heated by a heater or be cooled by a cooler. The heater is configured and adapted to heat the reactor at the temperature in the range from 20° C. to 250° C., preferably from 20° C. to 200° C., more preferably 20° C. to 100° C., most preferably 20° C. to 50° C. The cooler is configured and adapted to cool the reactor at the temperature in the range from −70° C. to +20° C., preferably from −50° C. to +20° C., more preferably −30° C. to +20° C., most preferably 0° C. to +20° C.

In the present invention, the reactor (12) is characterized in that the reactor is connected with a mixer (13) having 3-10 channels, preferred 3-6 channels for feeding the converting reagents for converting dihydroartemisinin (4) to the artemisinin derivative (5). The mixer is arranged between the column for reducing the artemisinin (3) to dihydroartemisinin (4) and the reactor (12), i.e. downstream to the column (9) or the second column (10B) and upstream to the reactor (12). Herein, the terms "upstream" and "downstream" are to be understood with reference to the flow direction. If the mixer (13) is "downstream", then it is located in flow direction after the component, i.e. the reacting solution passes at first through the column (9) or the second (10B) and then the mixer (13). If the mixer (13) is "upstream", it is located in flow direction before the reactor (12), i.e. the reacting solution passes at first through the mixer (13), and then the reactor (12).

Each of the channels is connected with the corresponding reagent reservoir filled with the prepared converting reagent or reagents solution. The converting reagent or reagents solution is fed respectively via the channel into the mixer. The mixer (13) has a switch configured and adapted to select the channels and to control closing and/or opening of the channels according to the selected converting reaction. The switch can be controlled automatically or manually. The converting reagents are fed via the channels selected by the switch into the mixer (13) and the mixer (13) mixes the converting reagents and the reacting solution (dihydroartemisinin solution) and feeds the mixture of the converting reagents and the reacting solution (dihydroartemisinin solution) into the reactor (12).

The multi-channel mixer (13) provides various combinations of the converting reagents for converting dihydroartemisinin (4) to artemisinin derivates (5). In an embodiment of the present invention, the reactor (12) is connected to a mixer (13) having 6 channels (FIG. 5). The channel 1 is connected with the column (9 or 10B) and the channel 6 is connected with the reactor (12) for converting dihydroartemisinin (4) to the artemisinin derivative (5). The channel 3-5 can be connected respectively with converting reagents reservoirs. For example, for producing of the artemisinin ether derivates—artemether (5a), arteether (5b) or artelinic acid (5d)—the channel 2 can be connected with a solution of an acid catalyst such as HCl, the channel 3 can be connected with a corresponding alcohol or a solution of a corresponding alcohol—methanol, ethanol or 4-(hydroxymethyl)benzoic acid—and the channel 4 can be connected with a corresponding trialkoxyorthoformate and the channel 5 can be closed or connected with another solvent for regulating the concentration of the reaction mixture. It is also possible that the channel 2 is connected with a solution of an acid catalyst and each of the channels 3-5 is connected respectively with a mixture of an alcohol and a corresponding trialkoxyorthoformate. In this case, the different artemisinin ether derivates can be produced by selecting the channels by the switch. For example, if the channel 3 is connected with the trimethoxyorthoformate solution in methanol, the channel 4 with the triethoxylorthoformate solution in ethanol, the channel 5 with a solution of 4-(hydroxymethyl)benzoic acid in THF, the artemether can be produced by selecting the channels 1, 2 and 3, the arteether can be produced by selecting the channels 1, 2 and 4, and the artelinic acid can be produced by selecting the channels 1, 2 and 5. The similar procedure can be applied for producing the various artemisinin ester derivatives. It is also possible to produce the artemisinin derivatives with different functional groups such as ether, ester, sulfonate, thioether, carbamate and thiocarbamate in sequence.

In another embodiment of the present invention, a simple T-mixer (13) having 3 channels can be used as said mixer (13). For example, via the $1^{st}$ channel is fed the reacting solution (dihydroartemisinin solution) obtained from the column (9 or 10B), via the $2^{nd}$ channel is fed the converting reagents solution for producing artemisinin derivative (5) and the $3^{rd}$ channel is connected with the reactor (12). In the T-mixer (13), the dihydroartemisinin solution and the converting reagents solution for producing artemisinin derivate (5) are mixed and fed via the $3^{rd}$ channel into the reactor (12). The $2^{nd}$ channel is connected with the converting reagents solution reservoir. For producing artemether (5a), the 2$^{nd}$ channel is connected with the reservoir filled with the converting reagents solution for artemether, such as a solution of trimethoxyorthoformate and HCl in methanol. For producing arteether (5b), the 2$^{nd}$ channel is connected with the reservoir filled with the converting reagents solution for producing arteether (5b) such as a solution of triethoxyorthoformate and HCl in ethanol. For producing artesunate (5c), the 2$^{nd}$ channel is connected with the converting reagents solution for producing artesunate (5c) such as a solution of succinic anhydride, triethylamine in dichloromethane (DCM).

Therefore, it is advantageous that various artemisinin derivatives (5) are produced in the continuous reactor of the present invention. The continuous flow reactor (6) of the present invention is able to produce various artemisinin derivatives (5) just by selecting the channels connected with the converting reagents solutions. This feature of the continuous flow reactor (6) of the present invention is superior over the batch reactor of the prior art as well as over the continuous flow reactor of WO2013030247A1.

Further, the present invention is directed to the artemisinin derivatives of the formula (5) prepared by any one of the above-mentioned inventive methods

5 wherein X is O or S and

R is —R$^1$, —COR$^1$, —CONHR$^1$, —CSNHR$^1$, or —SO$_2$R$^1$; and

R$^1$ represents a C$_1$-C$_{10}$ alkyl, C$_1$-C$_{10}$ halogenalkyl, C$_1$-C$_{10}$ hydroxyalkyl, C$_2$-C$_{10}$ alkoxyalkyl, C$_2$-C$_{10}$ carboxyalkyl, C$_6$-C$_{14}$ aryl, C$_7$-C$_{16}$ alkylaryl, C$_7$-C$_{16}$ alkoxyaryl, C$_7$-C$_{16}$ arylalkyl, C$_8$-C$_{16}$ arylalkoxyalkyl, C$_8$-C$_{16}$ alkylarylalkyl, C$_8$-C$_{16}$ alkylarylalkoxyalkyl, C$_2$-C$_{10}$ alkenyl, C$_2$-C$_{10}$ alkynyl, C$_3$-C$_8$ cycloalkyl, C$_4$-C$_{10}$ alkylcycloalkyl, C$_4$-C$_{10}$ alkoxyalkylcycloalkyl, C$_4$-C$_{12}$ cycloalkylalkyl, C$_4$-C$_{16}$ cycloalkylalkoxyalkyl, C$_1$-C$_5$ heterocyclyl, C$_3$-C$_{10}$ alkoxycarbonylalkyl, C$_2$-C$_{10}$ acyloxyalkyl, C$_3$-C$_{12}$ heterocyclylalkyl, C$_3$-C$_{10}$ alkylcarbonylaminoalkyl, C$_3$-C$_{10}$ alkoxycarbonylaminoalkyl, C$_1$-C$_{10}$ aminoalkyl, C$_2$-C$_{10}$ alkylaminoalkyl, C$_3$-C$_{10}$ dialkylaminoalkyl, C$_3$-C$_{10}$ alkylaminocarbonylalkyl, or C$_4$-C$_{10}$ dialkylaminocarbonylalkyl.

Preferred is the artemisinin derivative of the formula (5) prepared by any one of the above-mentioned inventive methods, wherein X is O; R is —R$^1$, —COR$^1$, or —CONHR$^1$; and R$^1$ represents a C$_1$-C$_{10}$ alkyl, C$_2$-C$_{10}$ alkoxyalkyl, C$_2$-C$_{10}$ carboxyalkyl, C$_7$-C$_{16}$ arylalkyl, or C$_4$-C$_{12}$ cycloalkylalkyl.

More preferred is the artemisinin derivative of the formula (5) prepared by any one of the above-mentioned inventive methods, wherein X is O; R is —R$^1$ or —COR$^1$; and R$^1$ represents a C$_1$-C$_{10}$ alkyl, C$_2$-C$_{10}$ carboxyalkyl, or C$_7$-C$_{16}$ arylalkyl.

Most preferred is the artemisinin derivative selected from the compounds 5-1-5-39:

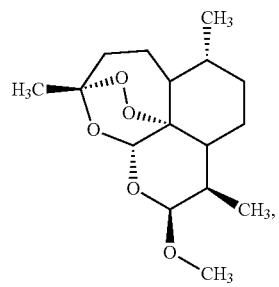

5-1

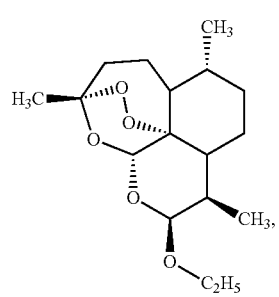

5-2

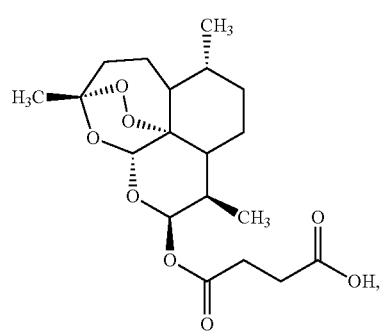

5-3

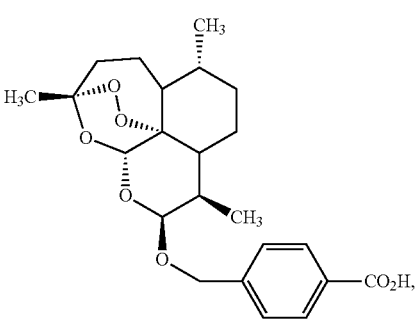

5-4

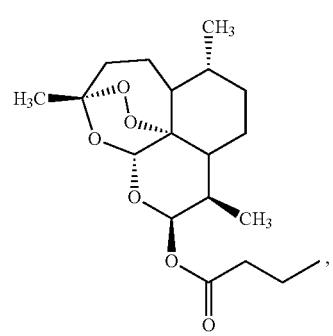

5-5

5-6
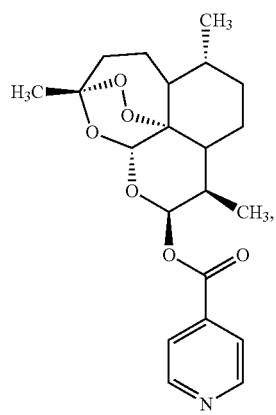
5-7
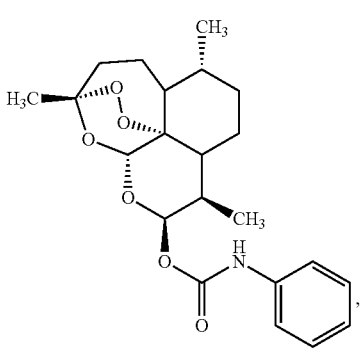
5-8
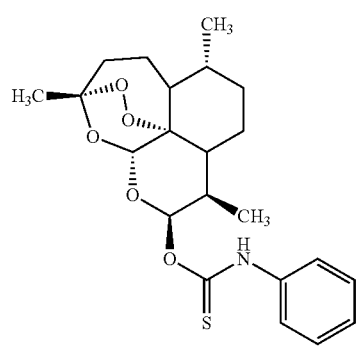
5-9
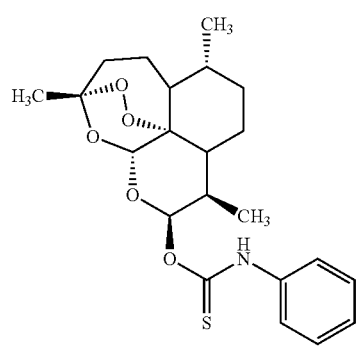
5-10
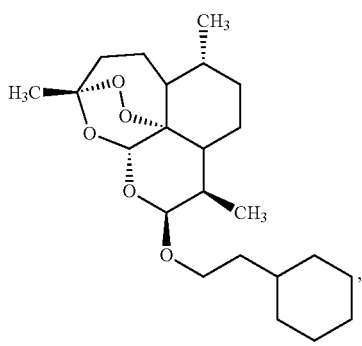
5-11
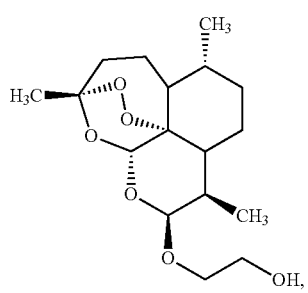
5-12
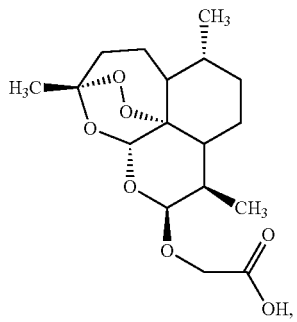
5-13
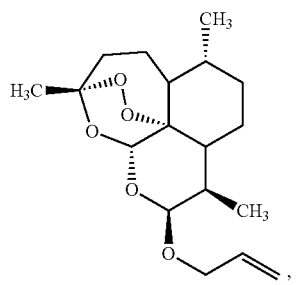
5-14
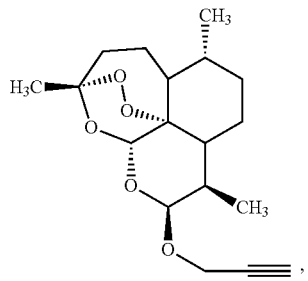

5-15

5-16

5-17

5-18

5-19

5-20

5-21

5-22

5-23

5-24

5-25
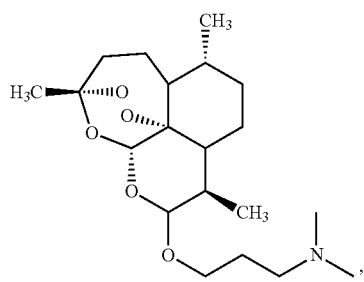
5-26
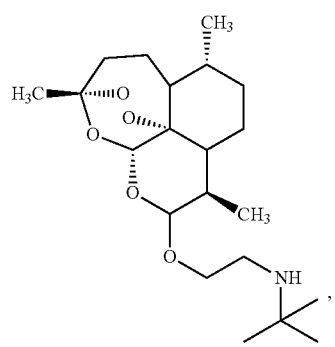
5-27
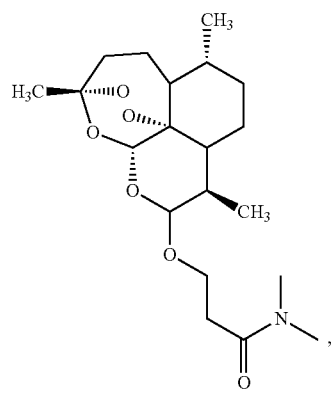
5-28
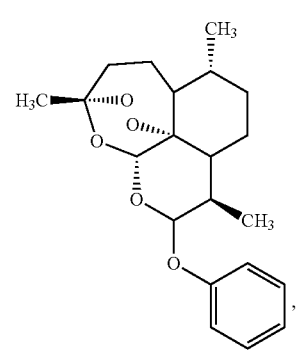
5-29
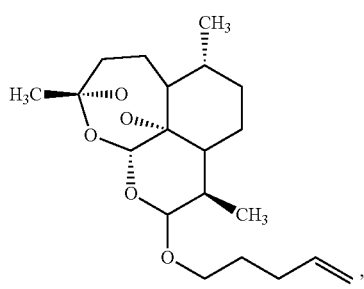
5-30
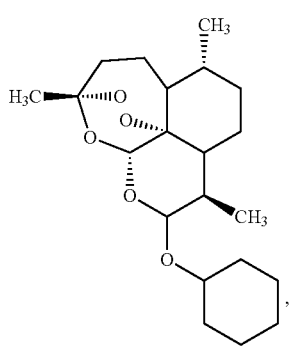
5-31
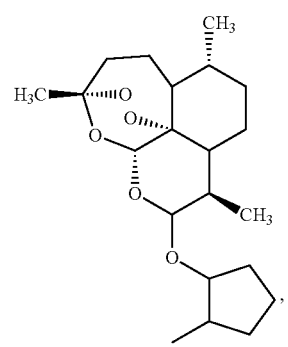
5-32
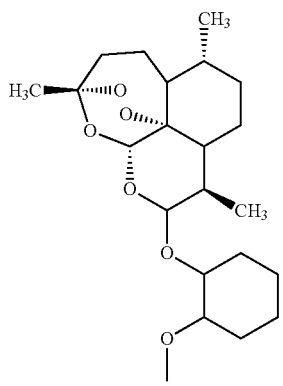
5-33
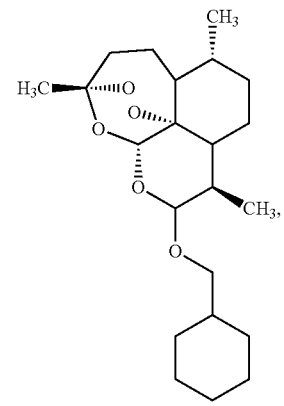

5-34

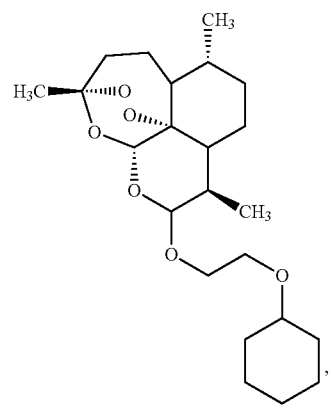

5-35

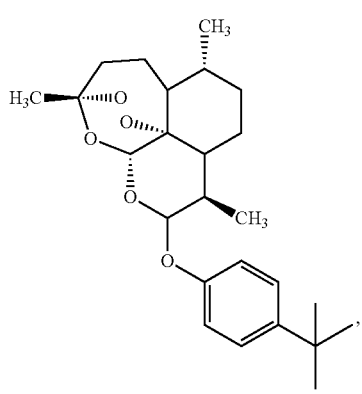

5-36

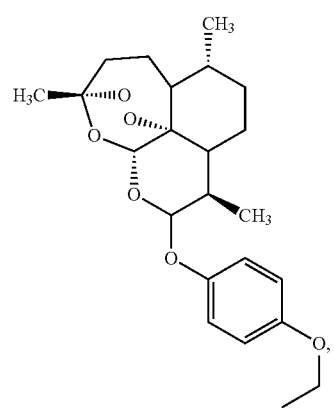

5-37

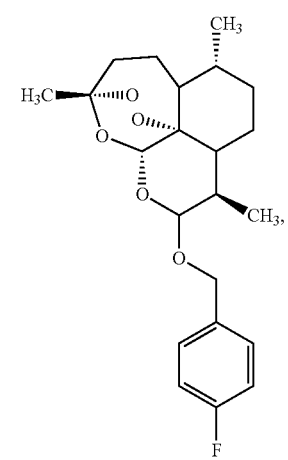

5-38

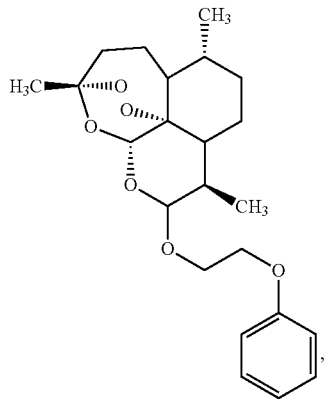

5-39

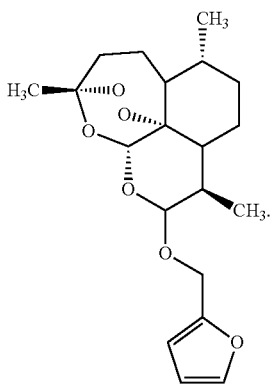

REFERENCE SIGNS (1) artemisinic acid
(2) dihydroartemisinic acid
(3) artemisinin
(4) dihydroartemisinin
(5) artemisinin derivative
(6) continuous flow reactor
(7) photochemical reactor
(8) reactor for acid mediated cleavage+oxidation with triplet oxygen
(9) column containing hydride reducing agent+activator+solid base
(10A) first column containing solid base
(10B) second column containing a hydride reducing agent and activator
(11) light source
(12) reactor for converting dihydroartemisinin to the artemisinin derivative
(13) mixer

DESCRIPTION OF FIGURES

FIG. 1B: Schematic drawing of synthesis of artemisinin (3) in continuous manner via the photochemical reactor (7) and the reactor (8) for performing an acid mediated cleavage of the photooxidation product and the subsequent oxidation with triplet oxygen

FIG. 2: Schematic drawing of the column (9) (Omni-Fit® 6.6 mm ID) for reduction of crude artemisinin output from photochemical reactor.

EXAMPLES

Methods:

$^1$H NMR spectra were recorded on a Varian 400-MR spectrometer (at 400 MHz) at ambient temperature. The proton signal of residual non-deuterated solvent (δ 7.26 ppm for CHCl$_3$) was used as an internal reference for $^1$H spectra. Data are reported as follows: chemical shift in parts per million (δ, ppm), multiplicity (s=singlet, d=doublet, t=triplet, q=quartet, qn=quintet, m=multiplet and br=broad), coupling constant reported in Hertz (Hz) and integration. $^{13}$C spectra were recorded on a Varian 400-MR spectrometer (at 101 MHz) at ambient temperature. Chemical shifts are reported in parts per million (δ, ppm). The carbon signal of deuterated solvent (δ 77.16 ppm for CDCl$_3$) was used as an internal reference for $^{13}$C spectra.

Infrared (IR) spectra were recorded as thin films on a Perkin-Elmer 1600 FTIR spectrophotometer. Melting points were recorded using an Electrothermal IA 9300 melting point apparatus and are uncorrected. Optical rotations (OR) were measured with a Schmidt & Haensch Unipol L 1000 at a concentration (c) expressed in g/100 mL. High-resolution mass spectra (HRMS) were recorded with an Agilent 6210 ESI-TOF mass spectrometer at the Freie Universität Berlin, Mass Spectrometry Core Facility. The measured [M+H$^+$] masses, if available, are indicated in the experimental part.

Analytical thin layer chromatography (TLC) was performed on Kieselgel 60 F254 glass plates pre-coated with a 0.25 mm thickness of silica gel. The TLC plates were visualized with UV light and by staining with an aqueous solution of potassium permanganate (KMnO$_4$) or a mixture of iodine and silica. Column chromatography was performed using Kieselgel 60 (230-400 mesh) silica gel with a typical 50-100:1 weight ratio of silica gel to crude product.

Figure 1A:
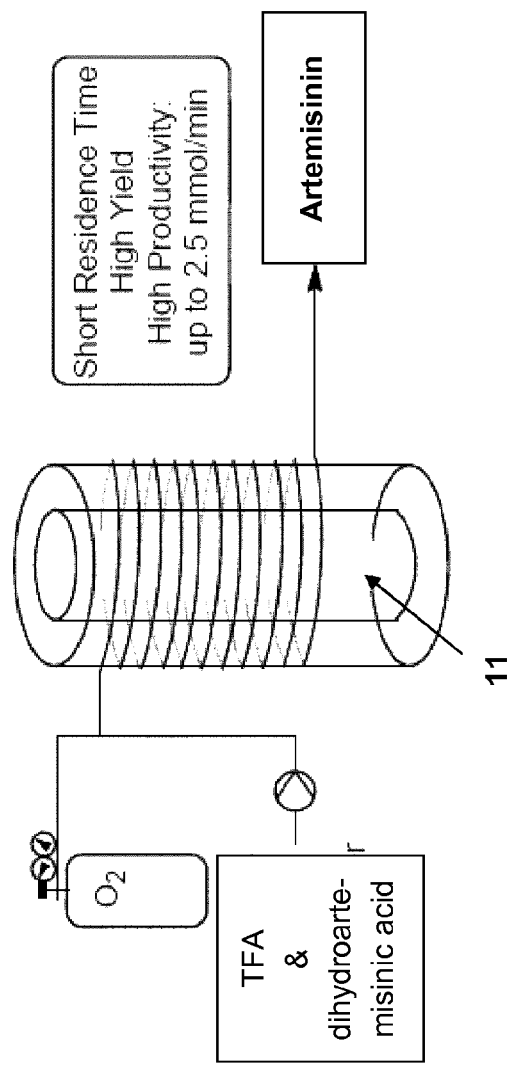
FIG. 1A: Schematic drawing of the photochemical reactor (7) for performing the photooxidation of dihydroartemisinic acid with singlet oxygen.

Example 1: Reaction Conditions for the Synthesis of Artemisinin (3) in Continuous Flow (FIG. 1B)

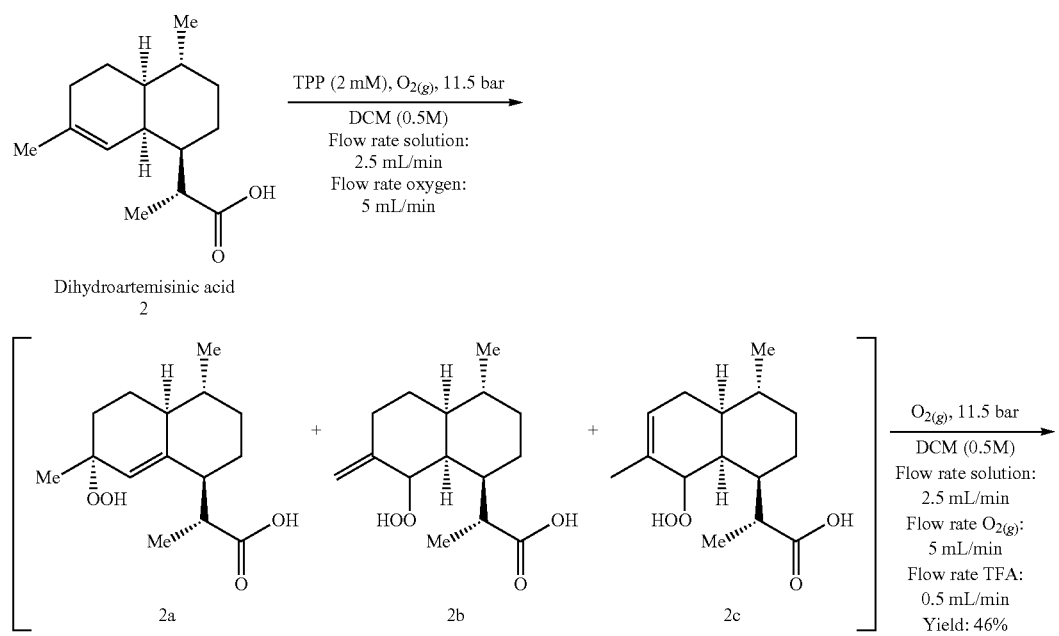

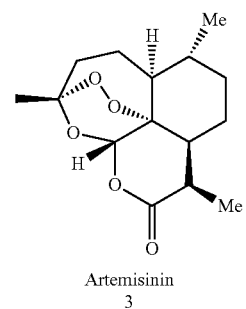

Artemisinin
3

Figure 3:
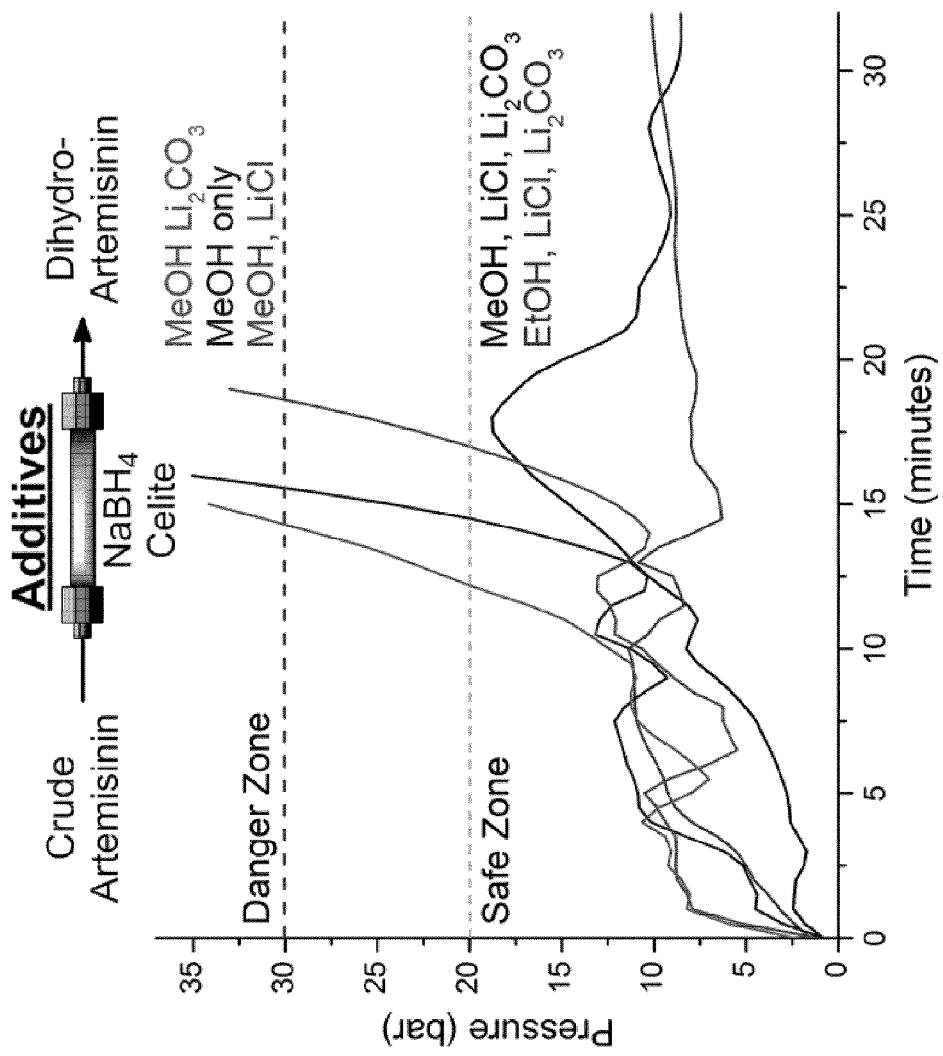
FIG. 3: System pressure observed during reduction of crude artemisinin as a function of cosolvent and solid additives in the Celite®/NaBH$_4$ column (9). All reactions run at 0.2 ml/min in THF with 2.6 ml of the 0.5 M crude solution. 9 equiv. (with respect to Artemisinin) of MeOH/EtOH used with a ratio of additives 1:1:1:0.7 (w/w) of NaBH$_4$:Celite:Li$_2$CO$_3$:LiCl.
Figure 4:
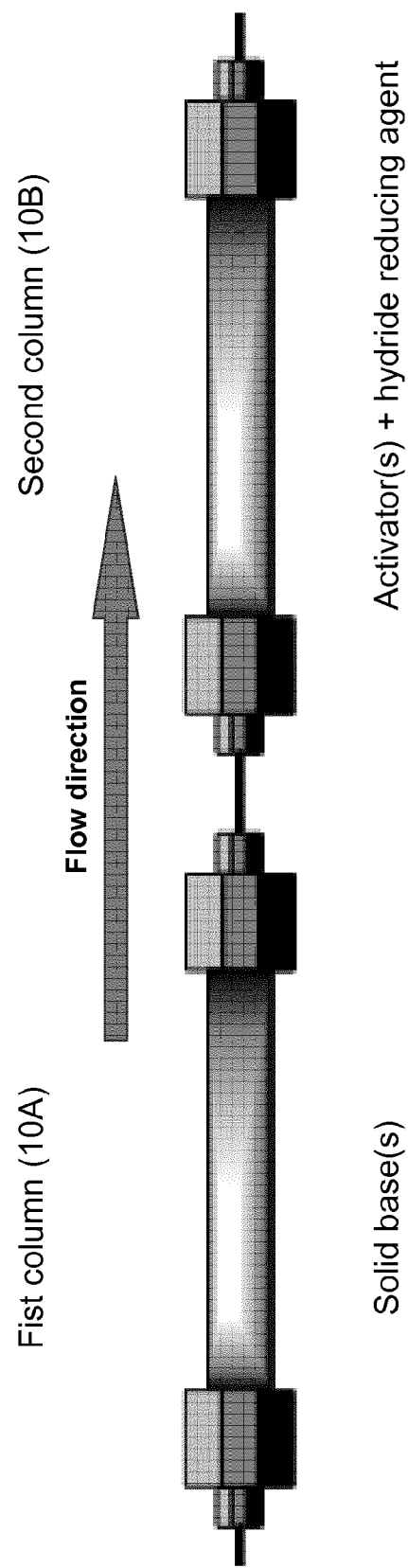
FIG. 4: Schematic drawing of the combination of the first column (10A) filled with at least one solid base and the second column (10B) filled with a mixture of hydride reducing agent and at least one activator.
Figure 5:
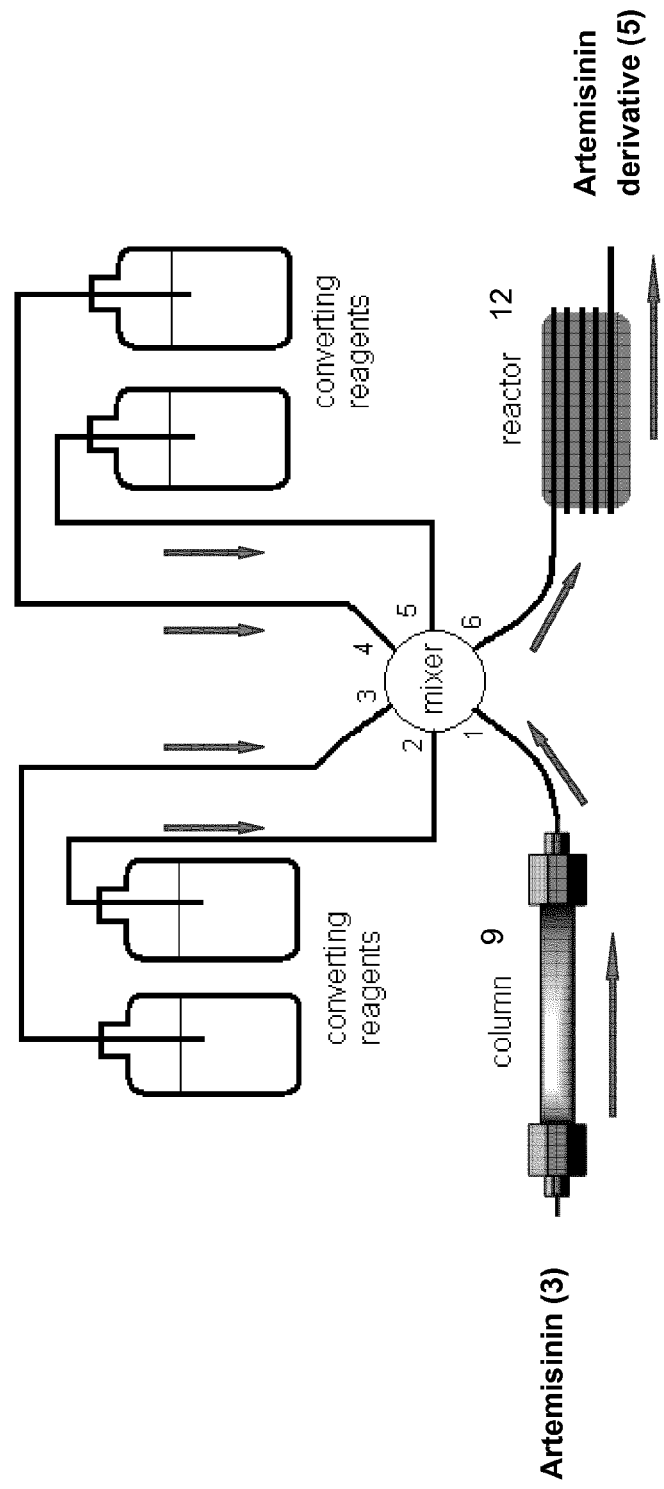
FIG. 5: Schematic drawing of the reactor (12) connected with a 6-channel mixer. The mixer (13) is arranged between the column for reducing artemisinin to dihydroartemisinin and the reactor (12) for converting dihydroartemisinin to the artemisinin derivates. The direction arrows represent the flow direction.

A solution of dihydroartemisinic acid (2.95 g, 12.5 mmol) and tetraphenylporphyrin (15 mg, 0.02 mmol) in dichloromethane (total volume of the solution: 25 mL, volumetric flask) and a solution of trifluoroacetic acid (1.9 mL, 25 mmol) in dichloromethane (18.1 mL) were prepared and given into their respective feed. The Hg lamp was turned on 30 min prior to the beginning of the experiment and the second portion of the photochemical reactor was heated at 60° C. The photochemical reactor (7) was flushed with pure dichloromethane (2.5 mL/min), dichloromethane (0.5 mL/min) and oxygen (7.5 mL/min, 11.5 bar) for 10 min. The reagents were then injected via their respective feed at a flow rate of 2.5 mL/min and the oxygen flow was readjusted to 7.5 mL/min (11.5 bar). Both streams joined in the first mixer. From there they entered the photochemical reactor (7). The TFA solution was injected at the exit of the photochemical reactor into a second mixer at a flow rate of 0.5 mL/min and the resulting mixture was pushed into the thermal reactor (8). The crude material containing the produced artemisinin was collected in a flask containing a saturated aqueous solution of NaHCO$_3$. The resulting biphasic mixture was stirred at room temperature until the green color disappeared. Phases were separated and the aqueous phase was extracted with dichloromethane (3 times). The combined organic layers were dried over anhydrous Na$_2$SO$_4$, filtered and concentrated under reduced pressure. Purification over silica gel (5%-20% EtOAc, in cyclohexane) afforded artemisinin (1.36 g, 39%) as a off-white solid. Further purification by recrystallization in cyclohexane afforded white needles. $^1$H NMR (400 MHz, CDCl$_3$) δ 5.86 (s, 1H), 3.40 (dq, J=7.3, 5.4 Hz, 1H), 2.47-2.39 (m, 1H), 2.08-1.98 (m, 2H), 1.91-1.86 (m, 1H), 1.81-1.74 (m, 2H), 1.51-1.34 (m, 3H), 1.45 (s, 3H), 1.21 (d, J=7.3 Hz, 3H), 1.11-1.04 (m, 2H), 1.00 (d, J=6.0 Hz, 3H). The $^1$H NMR spectrum of the obtained artemisinin (6) is shown in FIG. 3. Mp=153-154° C. $[\alpha]_D^{20}$+66.3° (c 0.97, CHCl$_3$). $^{13}$C NMR (101 MHz, CDCl$_3$) δ 172.2, 105.5, 93.9, 79.6, 50.2, 45.1, 37.7, 36.1, 33.8, 33.0, 25.4, 25.0, 23.6, 19.9, 12.7. IR (film) ν 2960, 2933, 2860, 1731, 1112, 991 cm$^{-1}$. HRMS calcd for C$_{15}$H$_{22}$O$_5$ (M+) 282.1467, found 282.1463. MS (EI) m/z 282 (1) [M$^+$], 250 (5), 192 (70), 150 (40), 55 (63), 43 (100).

Example 2: Flow Reactor Setup for the Synthesis of Artemisinin According to Example 1

Figure 1C:
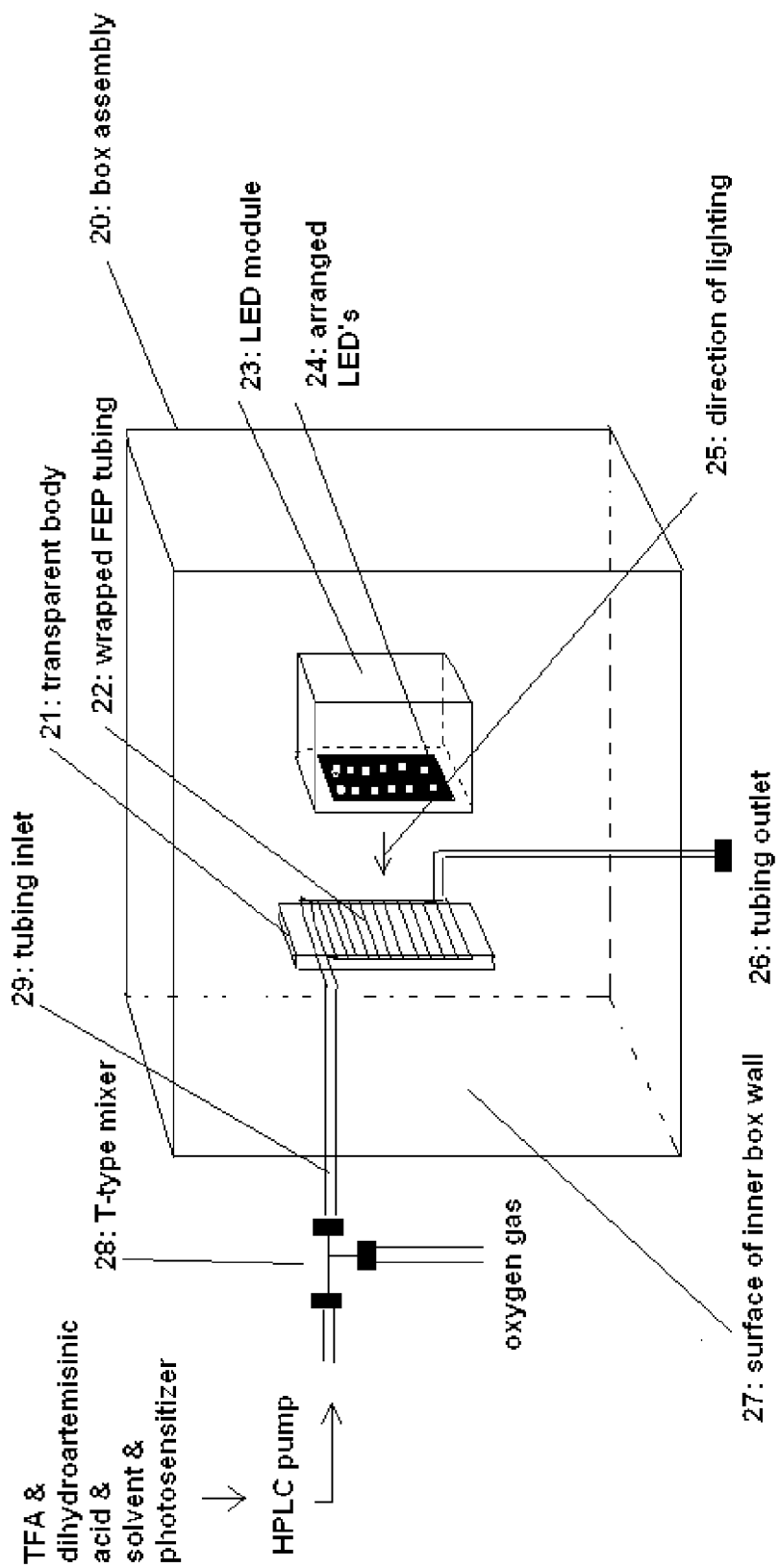
FIG. 1C: Schematic drawing of the LED box assembly (20) for performing the photooxidation of dihydroartemisinic acid with singlet oxygen
Figure 1D:
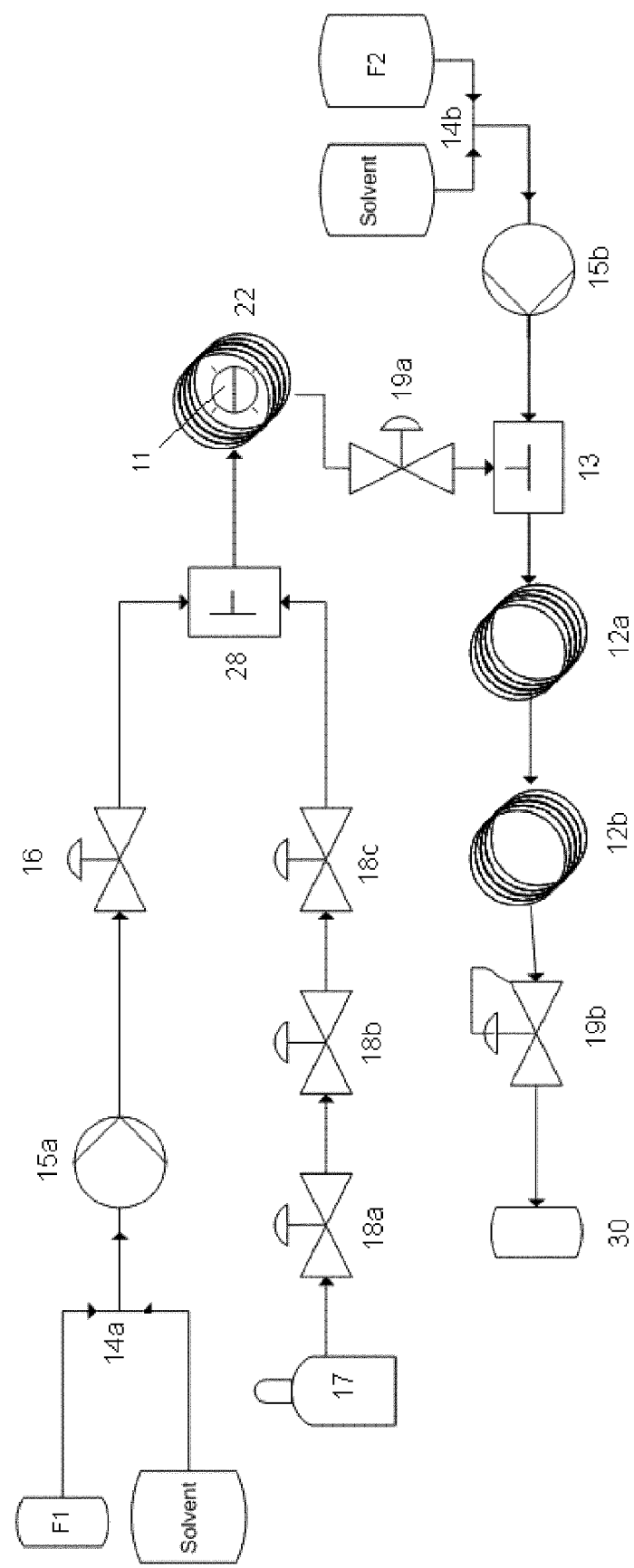
FIG. 1D: Schematic drawing of synthesis of artemisinin (3) in continuous manner via the photochemical reactor (7) and the reactor (8)

The flow reactor setup (FIG. 1D) for the synthesis of artemisinin (3) consists of a feed F1 for a solution of dihydroartemisinic acid (2), an automated two inlet switch valve 14a for regulating the composition of the feed for the solution of dihydroartemisinic acid (2), allowing for rapid switching from pure solvent to the solution containing the dissolved dihydroartemisinic acid, a first HPLC pump 15a (Vapourtec, R2C+ unit) downstream to switch valve 14a, pumping the dihydroartemisinic acid (2) solution with a throughput of 2.5 mL/min to the first ETFE T-mixer 28 (IDEX Health and Science, P-632) for mixing the dihydroartemisinic acid (2) solution and the oxygen, a first check-valve 16 (IDEX Health and Science, inline check-valve CV-3010) between the first HPLC pump 15a and the mixer 28, a mass flow controller 18b (Influx, SV1B5-AI05, allowing control of the oxygen flow rate from 5-90 cm$^3$/min) connected to a manometer 18a fixed on an oxygen tank 17 (Air Liquide, O$_2$ 99.995% pure), thus generating a steady oxygen flow of 7.5 mL/min, another check valve 18c (IDEX Health and Science, inline check-valve CV-3010) between the mass flow controller 18b and the first mixer 28, multiple loops of FEP tubing 22 (20 mL, IDEX Health & Science, fluorinated ethylene polymer 1520, natural color, outside diameter (OD) 1/16 in and inside diameter (ID) 0.030 in) wrapped tightly around a Pyrex filter 31 (inner diameter 4.5 cm and wall thickness 0.2 cm) which surrounds the quartz immersion well 32 cooled by a thermostat 33 (Huber, Unistat 360), a medium pressure Hg lamp 11 (Ace Glass, UV 450 immersion lamp, 5 in arc, radial lead, 7825-34), a power supply 34 for photochemical lamp 11 (Ace Glass, 7830), a second ETFE T-mixer 13 IDEX Health and Science, P-632), a first PTFE reactor 12a (11 mL, Omnifit, outside diameter (OD) 1/16 in and inside diameter (ID) 0.8 mm), a second PTFE reactor at room temperature 12b (5 mL, Vapourtec), a third heated (60° C.) PTFE reactor 12c (10 mL, Vapourtec, R4 unit) and a collection flask 30 for collecting the synthesized artemisinic acid. A feed F2 for the TFA solution is regulated via an automated two inlet switch valve 14b for regulating the composition of the feed for the TFA solution, allowing for rapid switching from pure solvent to the TFA solution. A second HPLC pump 15b (Vapourtec, R2C+ unit) pumps TFA with a throughput of 0.5 mL/min to into the second mixer 28 disposed at the outlet of the tubing 22 of the photochemical reactor. There the TFA is reacted with the products of the photochemical reactor process. A back-pressure regulator 19b of 2.2 bar (Vapourtec) was installed in order to increase the internal pressure of the system. FEP tubing was selected for its high transmittance and stability in the UV-vis light range, its flexibility and its high chemical resistance. The 2 mm thick Pyrex filter was essential to absorb wavelengths below 300 nm, to prevent degradation of the tubing, and to avoid any undesired side reactions involving short wavelength light. The temperature in the tube during the reaction is estimated to range from 25 to 30° C., based on temperature measurements taken between the cooling jacket and the tube. For safety reasons, the lamp was placed inside an aluminum box for blocking UV irradiation. Two fans were installed for additional cooling.

Example 3: Synthesis of Hydroperoxide (2a-c) in Continuous Flow Using the Box Assembly The flow reactor setup (FIG. 1C) for the synthesis of hydroperoxide (3) consists of a feed F1 for a solution of dihydroartemisinic acid (2), a pumping unit analogously to example 2 (consisting of an automated two inlet switch valve 14a for regulating the composition of the feed for the solution of dihydroartemisinic acid (2), allowing for rapid switching from pure solvent to the solution containing the dissolved dihydroartemisinic acid, a HPLC pump 15a (Vapourtec, R2C+ unit) downstream to switch valve 14a), pumping the dihydroartemisinic acid (2) solution with a throughput of 1.25 mL/min to a ETFE T-mixer 28 (IDEX Health and Science, P-632) for mixing the dihydroartemisinic acid (2) solution and the oxygen, a mass flow controller 18b (Influx, SV1B5-AI05, allowing control of the oxygen flow rate from 5-90 cm$^3$/min) connected to a manometer 18a fixed on an oxygen tank 17 (Air Liquide, O$_2$ 99.995% pure), thus generating a steady oxygen flow of 5 mL/min, a check valve 18c (IDEX Health and Science, inline check-valve CV-3010) between the mass flow controller 18b and the mixer 28, a photochemical reactor comprising the mixer and a tubing inlet 29, consisting of multiple loops of FEP tubing 22 (3.8 mL, IDEX Health & Science, fluorinated ethylene polymer 1520, natural color, outside diameter (OD) 1/16 in and inside diameter (ID) 0.030 in) wrapped tightly around a transparent body 21 (polycarbonate plate, size 9.0×14.0 cm$^2$) which is irradiated by an arrangement of 60 High Power LEDs 24 combined in an LED module 23 emitting at 420 nm (OSA Opto Lights, 72 W electrical power, cooled by a fan, emission area 2.5×2.5 cm$^2$) or at 660 nm (OSA Opto Lights, 46 W electrical power, cooled by a fan, emission area 2.5×2.5 cm$^2$), electronics for supplying a constant current to the LED module (OSA Opto Lights), a power supply (Manson HCS-3202) and a back-pressure regulator of 6.9 bar (IDEX Health and Science) installed after the tubing outlet 26 in order to increase the internal pressure of the system. Because the LED module does not emit UV-radiation which would lead to undesired side reactions, additional filters are not necessary. The wrapped FEP tubing 22 was irradiated directly by the LED module 23, which was installed in a distance of 3 cm in front of the transparent body 21. For maximum efficiency, the tubing was irradiated in a box covered with reflective material 27 (aluminium foil). No additional cooling system for the photochemical reactor was installed. When using the LED module emitting at 420 nm, the feed F3 was a solution of dihydroartemisinic acid at a concentration of 0.5 mol/L and the photosensitizer tetraphenylporphyrin at a concentration of 1 mmol/L in dichloromethane (2.95 g dihydroartemisinic acid and 15 mg tetraphenylporphyrin, total volume 25 mL, volumetric flask), whereas the photosensitizer was methylene blue instead of tetraphenylporphyrin at a concentration of 1 mmol/L when using the LED module emitting at 660 nm (2.95 g dihydroartemisinic acid and 8 mg methylene blue, total volume 25 mL, volumetric flask). The feed was introduced at a flow rate of 1.25 mL/min and the oxygen flow adjusted to 5 mL/min, resulting in a nearly complete conversion of 99% yielding 72% of the desired hydroperoxide (3) with a selectivity of 73% (LED module emitting at 420 nm). When increasing the flow rate, a higher productivity is achieved, however at the expense of the high conversion, as shown in Table 1:

TABLE 1

| flow rate feed F3 | | flow rate | conversion | yield hydro- | |
|---|---|---|---|---|---|
| mL/min | mmol/min | min mmol$^{-1}$ | | mmol/min | peroxide 2a | selectivity |
| 5 | 2.5 | 0.4 | 51.4% | 1.29 | 36.7% | 71.3% |
| 2.5 | 1.25 | 0.8 | 82.9% | 1.04 | 59.2% | 71.4% |
| 1.75 | 0.875 | 1.143 | 90.3% | 0.79 | 66.7% | 73.9% |
| 1.25 | 0.625 | 1.6 | 99.3% | 0.62 | 72.7% | 73.2% |

For obtaining artemisinin, the product stream leaving the photochemical reactor at the tubing outlet 26 can be mixed with a solution of trifluoroacetic acid at a concentration of 1.875 mol/L in dichloromethane (1.9 mL trifluoroacetic acid in 18.1 mL dichloromethane) and reacted in a thermal reactor, analogously as described in example 5, injecting the trifluoroacetic acid solution at a flow rate of 0.25 mL/min. Alternatively trifluoroacetic acid can already be added to the feed solution F3 at a concentration of 0.375 mol/L.

Figure 1E:
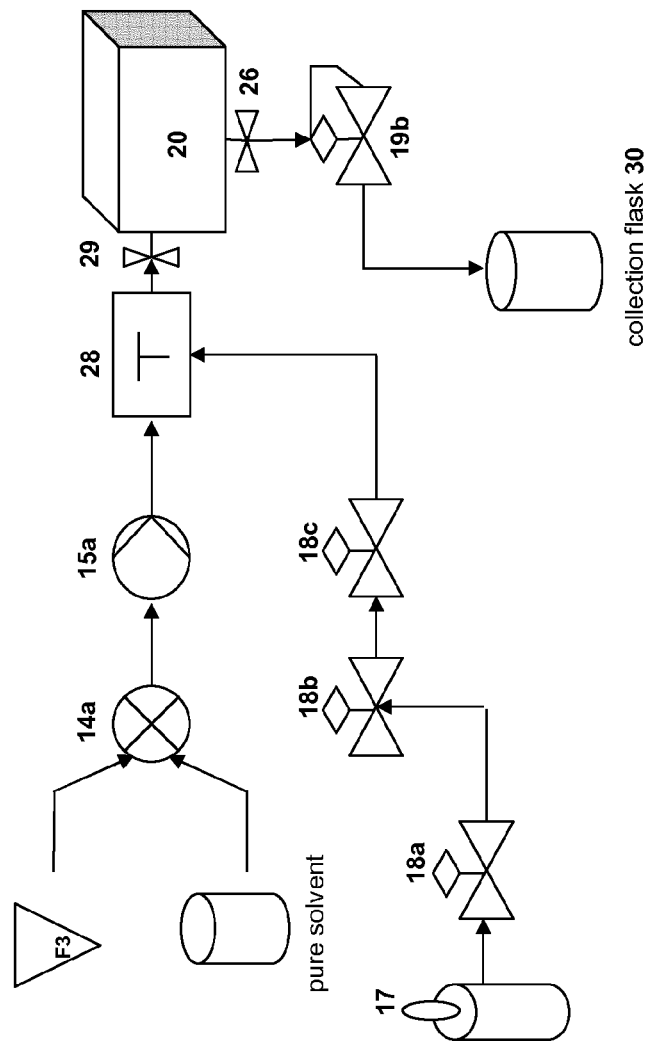
FIG. 1E: Schematic drawing of synthesis of artemisinin (3) in continuous manner via the LED reactor (20).

Example 4: Synthesis of Artemisinin (3) in Continuous Flow Using the Cooled Box Assembly (FIG. 1E)

The flow reactor setup for the synthesis of artemisinin consists of a feed for a mixture of dihydroartemisinic acid, trifluoroacetic acid and the photosensitizer dicyanoanthracene, a pumping unit analogously to example 2 (consisting of an automated two inlet switch valve 14a for regulating the composition of the feed for the solution of dihydroartemisinic acid, allowing for rapid switching from pure solvent to the feed solution containing the dissolved dihydroartemisinic acid, an HPLC pump 15a (Vapourtec, R2C+ unit) downstream to switch valve), pumping the dihydroartemisinic acid solution with a throughput of 1.25 mL/min to an ETFE T-mixer 28 (IDEX Health and Science, P-632) for mixing the feed solution and oxygen, a mass flow controller 18b (Influx, SV1B5-AI05, allowing control of the oxygen flow rate from 5-90 cm$^3$/min) connected to a manometer 18a fixed on an oxygen tank (Air Liquide, O$_2$ 99.995% pure), thus generating a steady oxygen flow of 5 mL/min, a check valve 18c (IDEX Health and Science, inline check-valve CV-3010) between the mass flow controller and the mixer, a photochemical reactor 20 comprising the mixer and a tubing inlet, consisting of multiple loops of FEP tubing (7 mL, IDEX Health & Science, fluorinated ethylene polymer 1520, natural color, outside diameter (OD) 1/16 in and inside diameter (ID) 0.030 in) wrapped tightly around a transparent body (glass plate, size 9.0×14.0 cm$^2$) which is irradiated by an arrangement of 60 High Power LEDs combined in an LED module emitting at 420 nm (OSA Opto Lights, 72 W electrical power, cooled by a fan, emission area 2.5×2.5 cm$^2$), electronics for supplying a constant current to the LED module (OSA Opto Lights) and a power supply (Manson HCS-3202). The wrapped FEP tubing was irradiated directly by the LED module, which was installed in a distance of 3 cm in front of the transparent body. For maximum efficiency, the tubing was irradiated in a tray made of stainless steel to reflect throughpassing light onto the photochemical reactor, which was immersed in this tray, filled with an ethylene glycol:water bath (3:2 v/v) cooled to −20° C. with the help of an immersion cooler (Huber, TC100E-F-NR). After leaving the photochemical reactor the solution was passed through a reactor with 10 ml volume (inner diameter 0.03 inch, FEP tubing), kept at 10° C. by immersion in a water bath and then 30 mL (inner diameter 0.06 inch, FEP tubing), kept at room temperature. A back-pressure regulator of 8 bar (Vapourtec) was installed after the tubing outlet in order to increase the internal pressure of the system.

The feed was a solution of dihydroartemisinic acid at a concentration of 0.5 mol/L, trifluoroacetic acid at a concentration of 0.25 mol/L and the photosensitizer dicyanoanthracene at a concentration of 2.5 mmol/L in toluene (29.5 g dihydroartemisinic acid, 7.13 g trifluoroacetic acid and 143 mg dicyanoanthracene, total volume 250 mL, volumetric flask). The feed was introduced at a flow rate of 1.25 mL/min and the oxygen flow adjusted to 5 mL/min.

The solution exiting the reactor was collected and washed twice with sat. NaHCO$_3$ to quench the acid and then washed with water and brine. The organic phase was dried over anhydrous Na$_2$SO$_4$ and concentrated under reduced pressure, then acetonitrile was added and evaporated to remove most toluene and dried under high vacuum overnight, yielding 30.509 g crude containing 22.945 g artemisinin according to NMR analysis. Thus a yield of 65% was achieved at a conversion of 97%.

The crude was solubilized in 60 mL acetonitrile, activated carbon added and the solution refluxed shortly. After cooling down, the carbon was filtrated off with a PTFE syringe filter (0.45 μm) and the solvent was removed, yielding 29.735 g of a nearly white solid, as most dicyanoanthracene is removed by this procedure.

The solid was recrystallized from 150 mL cyclohexane: ethanol (9:1 v/v), which yielded off-white needles. These were filtrated, washed three times with 100 mL cyclohexane each and dried under high vacuum (16.515 g, pure artemisinin according to NMR analysis, 47% isolated yield, recovery of recrystallization 72%).

The dried mother liquor (13.288 g) was recrystallized from 50 mL cyclohexane. This yielded slightly yellow crystals, which were washed with cyclohexane and dried under high vacuum (3.597 g, consisting of artemisinin with 96% purity (3.446 g), isolated yield 10%, total combined isolated yield including first recrystallization 57% (87% recovery)).

Both artemisinin batches were combined and recrystallized from 150 mL cyclohexane:ethanol (9:1 v/v), yielding purely white needles, which were filtrated off and washed twice with cyclohexane (16.079 g of pure artemisinin, 46% isolated yield based on initial dihydroartemisinic acid).

Example 5: Optimization of Composition of Filling Materials (According to FIG. 3)

When the crude solution of Artemisinin was pumped through a 1:1 mixture (w/w) of NaBH$_4$ and Celite, the process was unstable and clogged, but prior to clogging the effluent from the column contained almost pure DHA. Column clogging is quantified by measuring the back pressure as a function of time. As shown in FIG. 3, the column back-pressure is strongly dependent on column composition and solvent additives. As depicted, the column back-pressure rises quickly when crude artemisinin is pumped through the simple sodium borohydride/celite column (FIG. 3, blue line). We thus examined the additives which may facilitate the reduction. LiCl has been shown to accelerate NaBH$_4$ reductions via in situ formation of LiBH$_4$, however, clogging remained a problem (FIG. 3, cyan line). We hypothesized that the instability observed was the result of the TFA from the previous reaction, though no improvement was observed upon the addition of Li$_2$CO$_3$. Rewardingly, upon combining these two additives, mixing NaBH$_4$, Celite, Li$_2$CO$_3$, and LiCl in a 1:1:1:0.7 ratio (w/w), the clogging issue was eliminated (FIG. 3 red and black lines), providing complete and clean reduction of crude artemisinin. In addition to the column composition, an alcohol cosolvent was also found to be essential, ethanol providing the best results (FIG. 3, red line).

Figure 2:
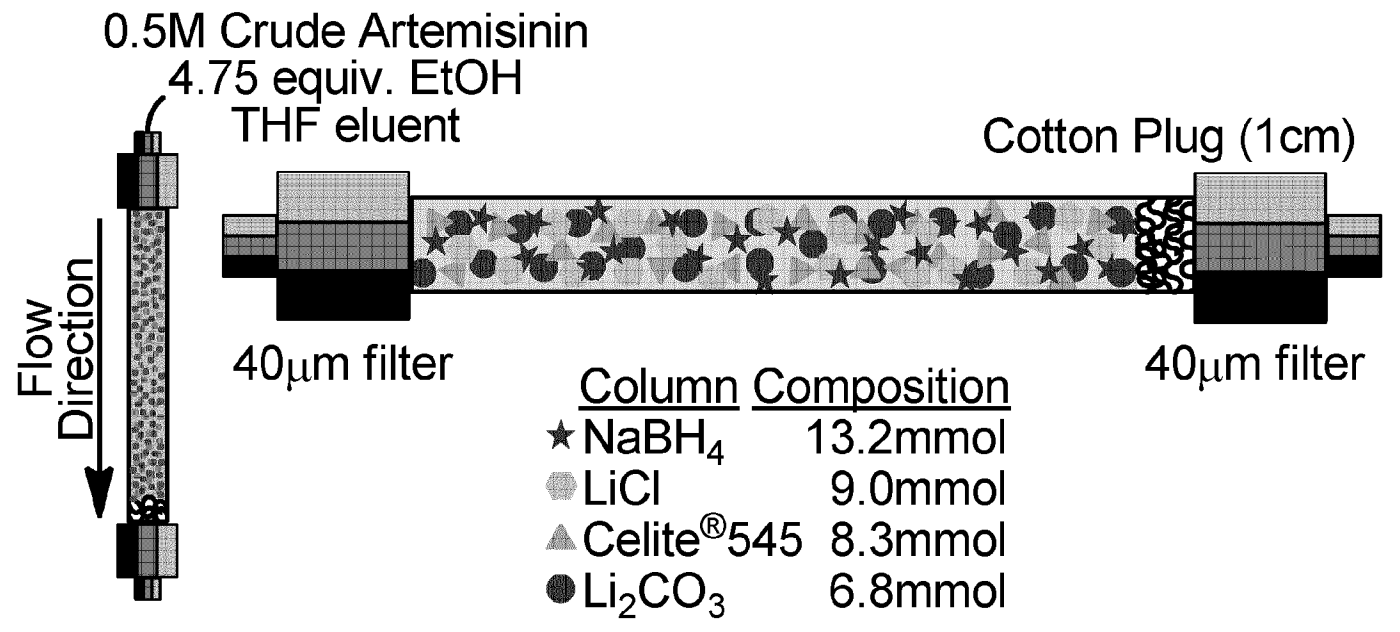

Example 6: Optimization of Reduction of Carbonyl Group by Sodium Borohydride and Activator. (FIG. 2)

A column packed with a 1:1 (w/w) mixture of celite and NaBH$_4$ gave inconsistent reductions of benzaldehyde in flow using THF as solvent. Leaching and precipitation of unidentified salts caused fluctuations in both pressure and conversion. While leaching was eliminated using SiO$_2$ plugs to terminate the column, benzaldehyde reductions still resulted in incomplete conversion.

Conversion was then measured as a function of cosolvent (MeOH) with 0.7 equiv. of LiCl (with respect to NaBH$_4$) added to the column mixture. The reduction to benzyl alcohol is dependent on methanol concentration, and a maximum conversion is achieved using 9-9.5 equivalents MeOH with respect to benzaldehyde.

TABLE 2

In-Flow Reduction of Aldehydes and Ketones to the Respective alcohols.[a]

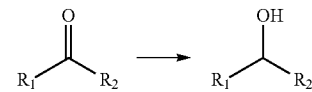

| Entry | R$_1$ | R$_2$ | Yield |
|---|---|---|---|
| 1 | C$_6$H$_5$ | H | 99% |
| 2 | 4-CNC$_6$H$_4$ | H | 99% |
| 3 | (E)-C$_6$H$_5$CHCH | H | 94% |
| 4 | CH$_3$(CH$_2$)$_4$ | H | 74% |
| 5 | Ph | Ph | 83% |
| 6 | CH(Ph)$_2$ | CH$_3$ | 74% |
| 7 | —CH$_2$(CH$_2$)$_3$CH$_2$— | | 89% |

[a]Column prepared using (1:1:0.76 w/w) Celite:NaBH$_4$:LiCl. Concentration aldehyde/ketone was 0.66M (THF) with 9.5 equiv. MeOH added, run at 0.5 mL/min.

Example 7-1. Reduction of Artemisinin (3) to Dihydroartemisinin (4) by Using the Inventive Continuous Flow Reactor with Two Columns To the crude solution of Artemisinin (2.7 mL), prepared as described in Example 4, was added 0.37 mL of ethanol. This was first passed through a 2.2 mL column (prepared by mixing 650 mg Celite and 650 mg Li$_2$CO$_3$ and packing into a 6.6 mm×150 mm Omnifit column with a 1 cm cotton plug at the outlet end. The material was packed by tapping on the bench top.) at a flow rate of 0.2 mL/min using THF as eluent. The resultant solution was then passed through a second, 2.5 mL column (prepared by grinding 650 mg Celite, 650 mg NaBH$_4$, and 520 mg LiCl together and packing into a 6.6 mm×150 mm Omnifit column with a 1 cm cotton plug at the outlet end. The material was packed by tapping on the bench top.) using THF as eluent and collected over water. Extraction with methylene chloride yielded the desired dihydroartemisinin.

Example 7-2. Reduction of Artemisinin (3) to Dihydroartemisinin (4) by Using the Inventive Continuous Flow Reactor with One Column

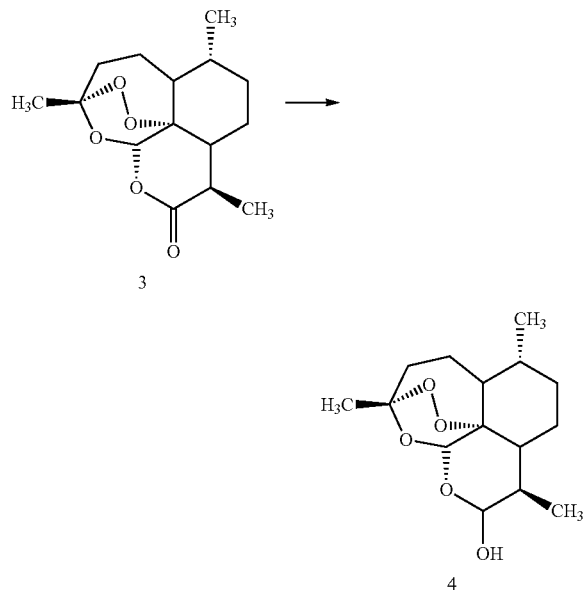

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top.) at a flow rate of 0.2 mL/min using THF as eluent and collected over water. Extraction with methylene chloride yielded the desired dihydroartemisinin.

$^1$H NMR ($CDCl_3$): 5.60 (s, 1H), 5.28 (t, J=4 Hz, 1H), 2.62 (m, 1H), 2.48 (dd, J=<4, 4 Hz, 1H), 2.38 (td, J=4, 8 Hz, 1H), 2.05 (m, 1H), 1.85 (m, 3H), 1.65 (m, 1H), 1.53 (m, 3H), 1.36 (m, 2H), 1.25 (m, 2H), 0.97 (s, 3H), 0.95 (s, 3H).

Figure 6:
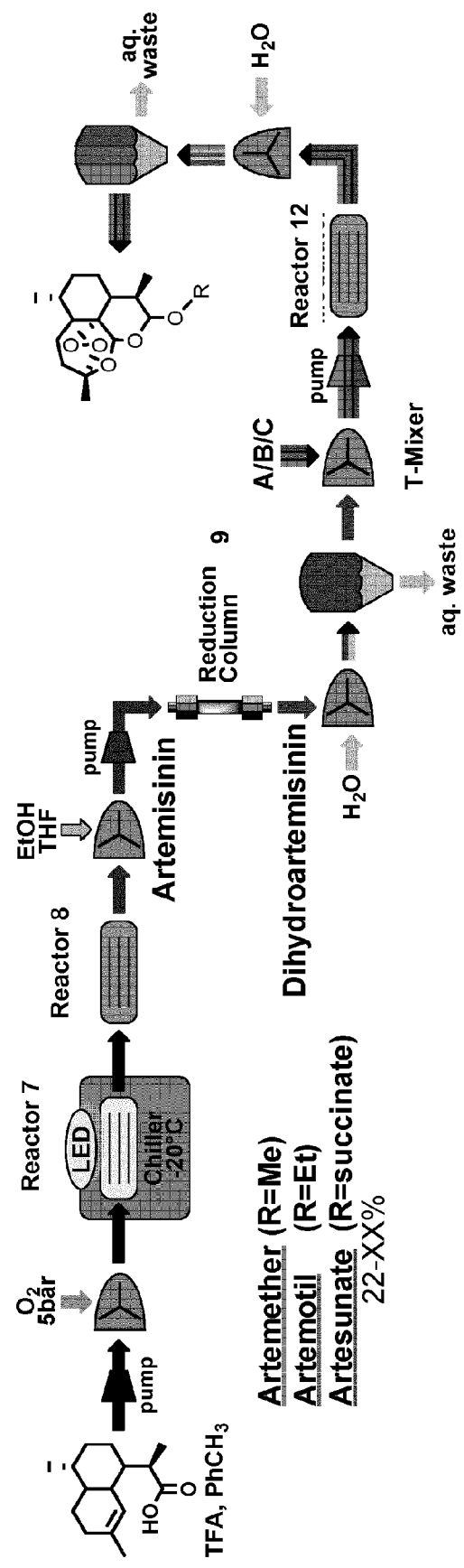
FIG. 6: Schematic drawing of the continuous flow reactor for the synthesis of artemisinin derivatives. A solution of dihydroartemisininic acid and trifluoroacetic acid (TFA) in toluene is combined via a simple T-mixer with oxygen gas. The gas-liquid mixture is irradiated with 420 nm light while maintaining the solution at −20° C., followed by 10 minutes at room temperature under visible light. The crude output of the photoreactor (artemisinin) is then passed through a composite NaBH$_4$ packed-bed. The resulting mixture is washed with water and the organic phase containing dihydroartemisinin is combined with either (A) HCl/trimethylorthoformate(TMOF)/CH$_3$OH, (B) HCl/triethylorthoformate(TEOF)/CH$_3$CH$_2$OH or (C) succinic anhydride/triethylamine/methylene chloride and allowed to react for X minutes. The output is the active pharmaceutical ingredients artemether (A), artemotil (B) or artesunate C).

Example 7-3. Synthesis of Artemether (5-1) from Artemisinin (3) by Using the Inventive Continuous Flow Reactor with One Column (FIG. 6)

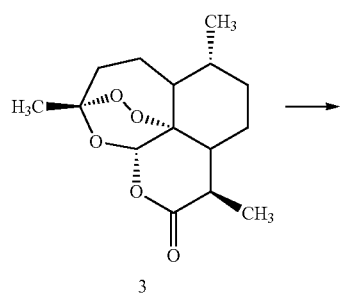

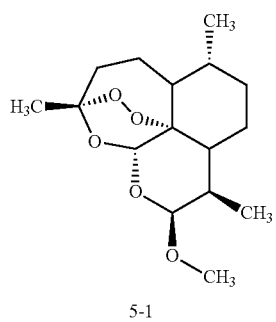

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution A (2 mL methanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemether 5-1 as white solid.

$^1$H NMR ($CDCl_3$): 5.38 (s, 1H), 4.68 (d, J=4 Hz, 1H), 3.42 (s, 3H), 2.63 (m, 1H), 2.37 (ddd, J=16, 12, 4 Hz, 1H), 2.02 (ddd, J=16, 4, 4 Hz, 1H), 1.88 (m, 1H), 1.76 (m, 2H), 1.64 (m, 1H), 1.49 (m, 2H), 1.44 (s, 3H), 1.34 (m, 1H), 1.24 (m, 1H), 0.96 (d, J=8 Hz, 3H), 0.92 (m, 1H), 0.9 (d, J=8 Hz, 3H).

Example 7-4. Synthesis of Arteether (5-2) from Artemisinin (3) by Using the Inventive Continuous Flow Reactor with One Column (FIG. 6)

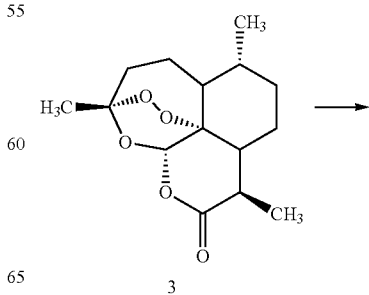

-continued

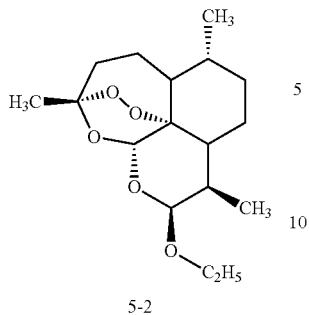

5-2

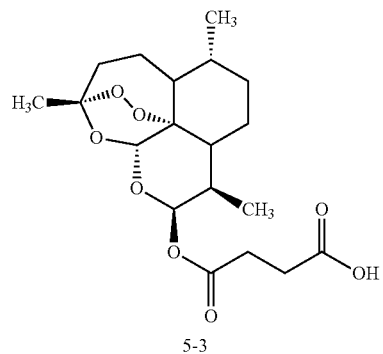

5-3

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL ethanol, 1 mL triethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure arteether 5-2 as white solid.

$^1$H NMR ($CDCl_3$): 5.40 (s, 1H), 4.79 (d, J=<4 Hz, 1H), 3.86 (dq, J=12, 8, 8 Hz, 1H), 3.47 (dq, J=8, 8, 4 Hz, 1H), 2.59 (m, 1H), 2.34 (ddd, J=12, 12, 4 Hz, 1H), 2.01 (ddd, J=16, 4, 4 Hz, 1H), 1.80 (m, 3H), 1.61 (ddd, J=12, 8, 4 Hz, 1H), 1.45 (m, 2H), 1.41 (s, 3H), 1.31 (m, 1H), 1.22 (dd, J=12, 8 Hz, 1H), 1.16 (t, J=8 Hz, 3H), 0.93 (d, J=8 Hz, 3H), 0.90 (m, 1H), 0.88 (d, J=8 Hz, 3H).

Example 7-5. Synthesis of Artesunate (5-3) from Artemisinin (3) by Using the Inventive Continuous Flow Reactor with One Column (FIG. 6)

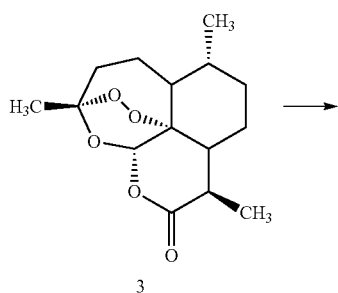

3

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution C (1.3 g succinic anhydride, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NH_4Cl$. The organic phase was dried down yielding an off-white solid. Purification was achieved by column chromatography over silica gel (5%-20% EtOAc, in cyclohexane) providing pure artesunate 5-3 as white solid.

$^1$H NMR ($CDCl_3$): 5.80 (d, J=8 Hz, 1H), 5.44 (s, 1H), 2.71 (m, 4H), 2.56 (m, 1H), 2.37 (td, J=16, 4 Hz, 1H), 2.04 (dt, J=16, 4 Hz, 1H), 1.87 (m, 1H), 1.75 (m, 2H), 1.62 (dt, J=12, 4 Hz, 1H), 1.43 (s, 3H), 1.49-1.27 (m, 4H), 1.02 (m, 1H), 0.96 (d, J=8 Hz, 3H), 0.85 (d, J=8 Hz, 3H).

Example 7-6. Synthesis of Artelinic Acid (5-4) from Artemisinin (3) by Using the Inventive Continuous Flow Reactor with One Column

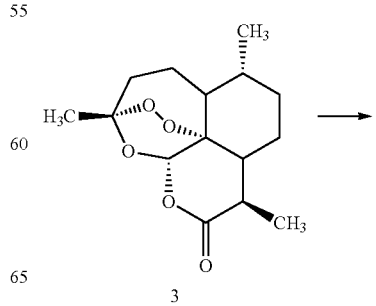

3

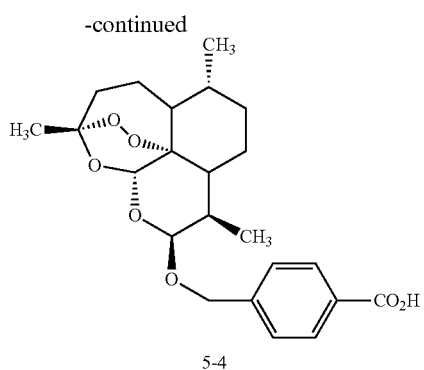

5-4

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution D (396 mg 4-(hydroxymethyl)benzoic acid was dissolved in 2 mL THF with 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artelinic acid 5-4 as white solid.

mass spec: $C_{23}H_{30}O_7$; 419.1982 [M+H$^+$].

Example 7-7. Synthesis of Artemether (5-1) from Dihydroartemisinic Acid (2)

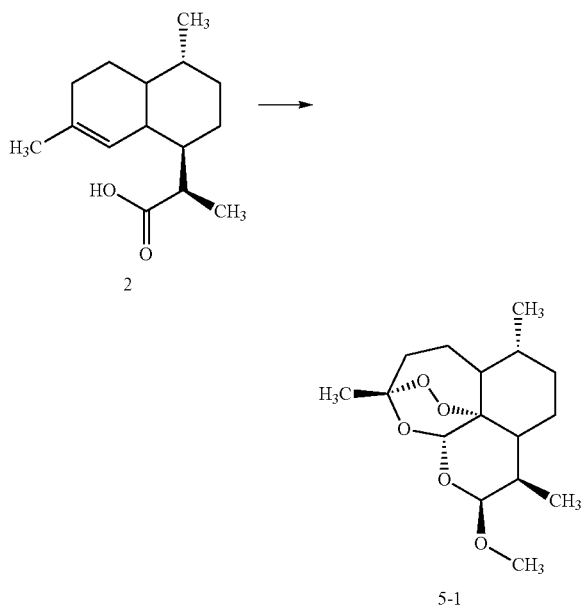

The initial stages of the transformation were performed according to Example 4, however, the stream exiting BPR 19B (FIG. 1D+E), as opposed to entering collection flask 30, was fed into a mixer, where it was mixed with a EtOH (6 equiv. with respect to DHAA)/THF solution. The resulting solution was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution A (2 mL methanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemether 5-1 as white solid.

$^1$H NMR (CDCl$_3$): 5.38 (s, 1H), 4.68 (d, J=4 Hz, 1H), 3.42 (s, 3H), 2.63 (m, 1H), 2.37 (ddd, J=16, 12, 4 Hz, 1H), 2.02 (ddd, J=16, 4, 4 Hz, 1H), 1.88 (m, 1H), 1.76 (m, 2H), 1.64 (m, 1H), 1.49 (m, 2H), 1.44 (s, 3H), 1.34 (m, 1H), 1.24 (m, 1H), 0.96 (d, J=8 Hz, 3H), 0.92 (m, 1H), 0.9 (d, J=8 Hz, 3H). mass spec: $C_{16}H_{26}O_5$; 299.1769 [M+H$^+$].

Example 7-8. Synthesis of Arteether (5-2) from Dihydroartemisinic Acid (2)

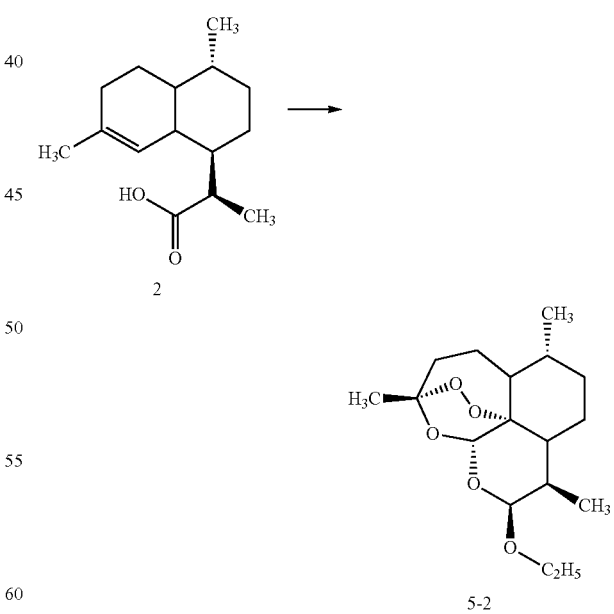

The initial stages of the transformation were performed according to Example 4, however, the stream exiting BPR 19B (FIG. 1D+E), as opposed to entering collection flask 30, was fed into a mixer, where it was mixed with a EtOH (6 equiv. with respect to DHAA)/THF solution. The resulting solution was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL ethanol, 1 mL triethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure arteether 5-2 as white solid.

$^1$H NMR ($CDCl_3$): 5.40 (s, 1H), 4.79 (d, J=<4 Hz, 1H), 3.86 (dq, J=12, 8, 8 Hz, 1H), 3.47 (dq, J=8, 8, 4 Hz, 1H), 2.59 (m, 1H), 2.34 (ddd, J=12, 12, 4 Hz, 1H), 2.01 (ddd, J=16, 4, 4 Hz, 1H), 1.80 (m, 3H), 1.61 (ddd, J=12, 8, 4 Hz, 1H), 1.45 (m, 2H), 1.41 (s, 3H), 1.31 (m, 1H), 1.22 (dd, J=12, 8 Hz, 1H), 1.16 (t, J=8 Hz, 3H), 0.93 (d, J=8 Hz, 3H), 0.90 (m, 1H), 0.88 (d, J=8 Hz, 3H). mass spec: $C_{17}H_{28}O_5$; 313.1925 [M+H$^+$].

Example 7-9. Synthesis of Artesunate (5-3) from Dihydroartemisinic Acid (2)

solution was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution C (1.3 g succinic anhydride, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NH_4Cl$. The organic phase was dried down yielding an off-white solid. Purification was achieved by column chromatography over silica gel (5%-20% EtOAc, in cyclohexane) providing pure artesunate 5-3 as white solid.

$^1$H NMR ($CDCl_3$): 5.80 (d, J=8 Hz, 1H), 5.44 (s, 1H), 2.71 (m, 4H), 2.56 (m, 1H), 2.37 (td, J=16, 4 Hz, 1H), 2.04 (dt, J=16, 4 Hz, 1H), 1.87 (m, 1H), 1.75 (m, 2H), 1.62 (dt, J=12, 4 Hz, 1H), 1.43 (s, 3H), 1.49-1.27 (m, 4H), 1.02 (m, 1H), 0.96 (d, J=8 Hz, 3H), 0.85 (d, J=8 Hz, 3H). mass spec: $C_{19}H_{28}O_8$; 385.1777 [M+H$^+$].

Example 7-10. Synthesis of Artelinic Acid (5d) from Dihydroartemisinic Acid (2)

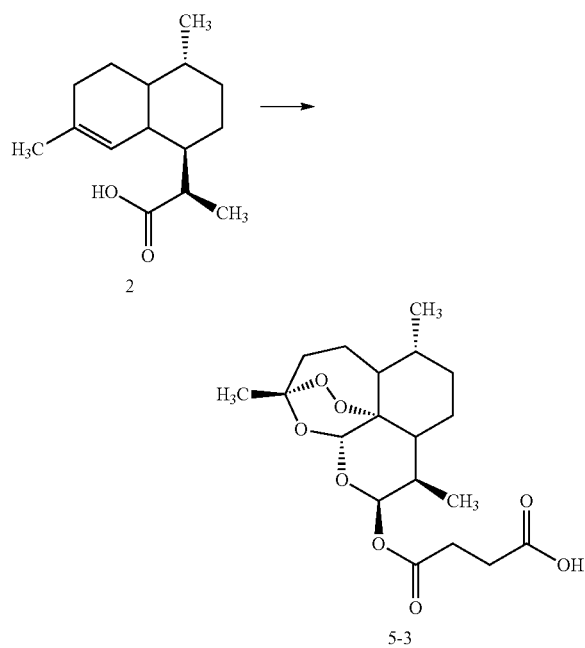

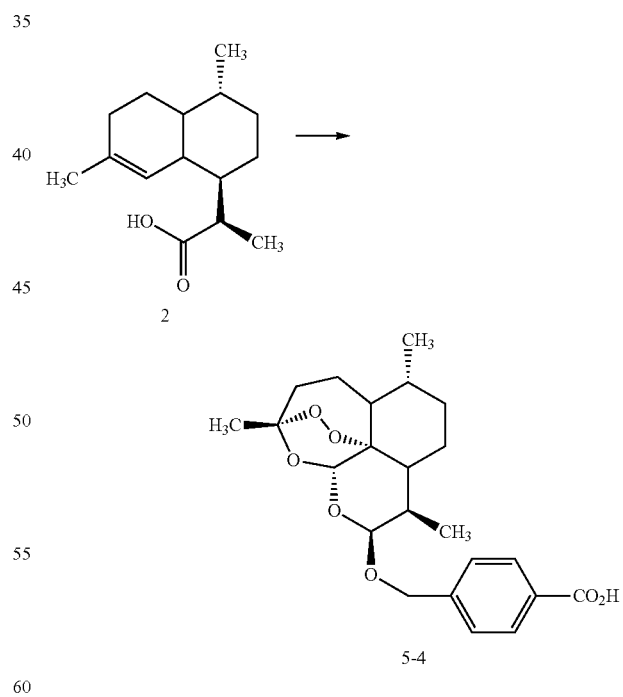

The initial stages of the transformation were performed according to Example 4, however, the stream exiting BPR 19B (FIG. 1D+E), as opposed to entering collection flask 30, was fed into a mixer, where it was mixed with a EtOH (6 equiv. with respect to DHAA)/THF solution. The resulting The initial stages of the transformation were performed according to Example 4, however, the stream exiting BPR 19B (FIG. 1D+E), as opposed to entering collection flask 30, was fed into a mixer, where it was mixed with a EtOH (6 equiv. with respect to DHAA)/THF solution. The resulting solution was passed through a 2.2 mL column (prepared by mixing 650 mg Celite and 650 mg Li₂CO₃, 650 mg NaBH₄, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (396 mg 4-(hydroxymethyl)benzoic acid was dissolved in 2 mL THF with 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO₃. The organic phase was dried down yielding an off-white solid. Purification was achieved by column chromatography over silica gel (5%-20% EtOAc, in cyclohexane) providing pure artelinic acid 5-4 as white solid.

mass spec: $C_{23}H_{30}O_7$; 419.1971 [M+H⁺].

Example 7-11. Synthesis of Artemisinin Ester Derivate (5-5) from Artemisinin (3)

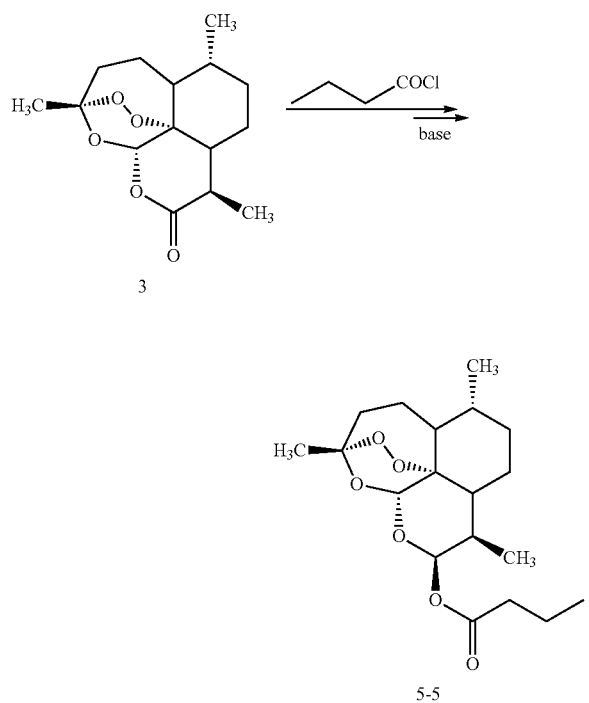

To the crude solution of Artemisinin (2.7 mL), prepared as described in Example 4, was added 0.37 mL of ethanol. This was passed through a 2.2 mL column (prepared by mixing 650 mg Celite and 650 mg Li₂CO₃, 650 mg NaBH₄, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.27 mL butyryl chloride, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NH₄Cl. The organic phase was dried down yielding an off-white solid. Purification was achieved by column chromatography over silica gel (5%-20% EtOAc, in cyclohexane) providing pure Artemisinin derivative 5-5 as white solid. mass spec: $C_{19}H_{30}O_6$; 355.2038 [M+H⁺].

Example 7-12. Synthesis of Artemisinin Ester Derivate (5-6) from Artemisinin (3)

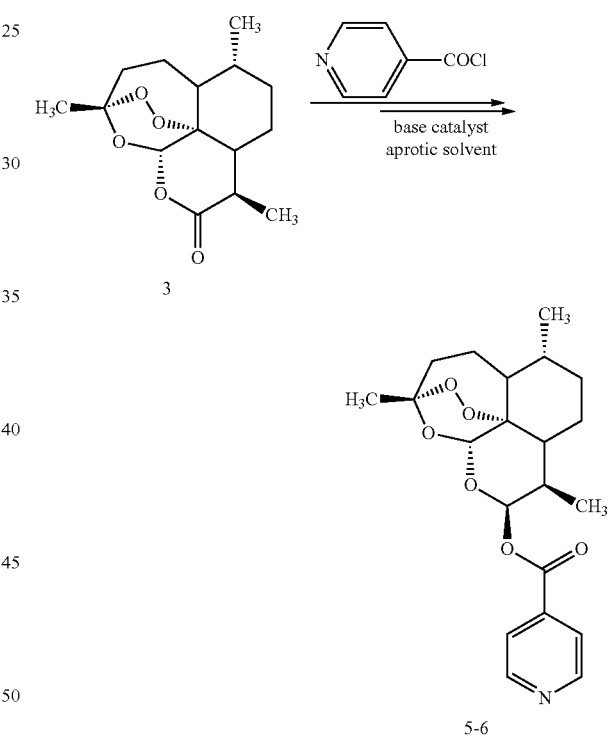

To the crude solution of Artemisinin (2.7 mL), prepared as described in Example 4, was added 0.37 mL of ethanol. This was passed through a 2.2 mL column (prepared by mixing 650 mg Celite and 650 mg Li₂CO₃, 650 mg NaBH₄, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (368 mg isonicotinoyl chloride, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NH$_4$Cl. The organic phase was dried down yielding an off-white solid. Purification was achieved by column chromatography over silica gel (5%-20% EtOAc, in cyclohexane) providing pure Artemisinin derivative 5-6 as white solid.

mass spec: C$_{21}$H$_{27}$NO$_6$; 390.1818 [M+H$^+$].

Example 7-13. Synthesis of Artemisinin Sulfonate Derivative (5-7) from Artemisinin (3)

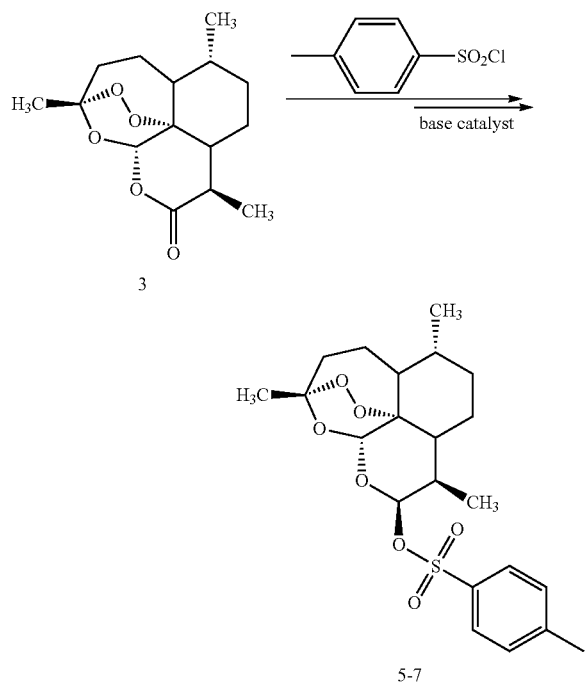

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (496 mg p-tolylsulfonyl chloride, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NH$_4$Cl. The organic phase was dried down yielding an off-white solid. Purification was achieved by column chromatography over silica gel (5%-20% EtOAc, in cyclohexane) providing pure Artemisinin derivative 5-7 as white solid.

mass spec: C$_{22}$H$_{30}$O$_7$S; 439.1685 [M+H$^+$].

Example 7-14. Synthesis of Artemisinin Carbamate Derivative (5-8) from Artemisinin (3)

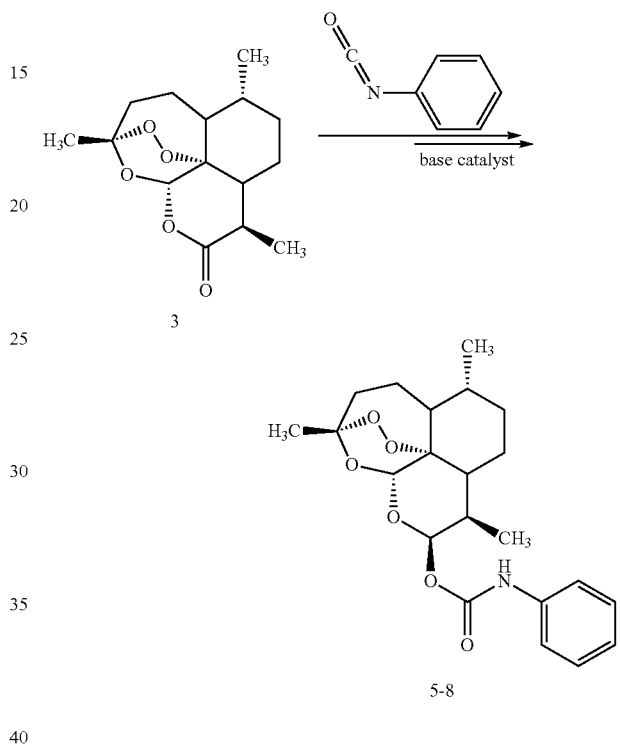

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.321 mL benzyl isocyanate, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NH$_4$Cl. The organic phase was dried down yielding an off-white solid. Purification was achieved by column chromatography over silica gel (5%-20% EtOAc, in cyclohexane) providing pure Artemisinin derivative 5-8 as white solid.

mass spec: C$_{22}$H$_{29}$NO$_6$; 404.1978 [M+H$^+$].

Example 7-15. Synthesis of Artemisinin Thiocarbamate Derivative (5-9) from Artemisinin (3)

Example 7-16. Synthesis of Artemisinin Ether Derivative (5-10) from Artemisinin (3)

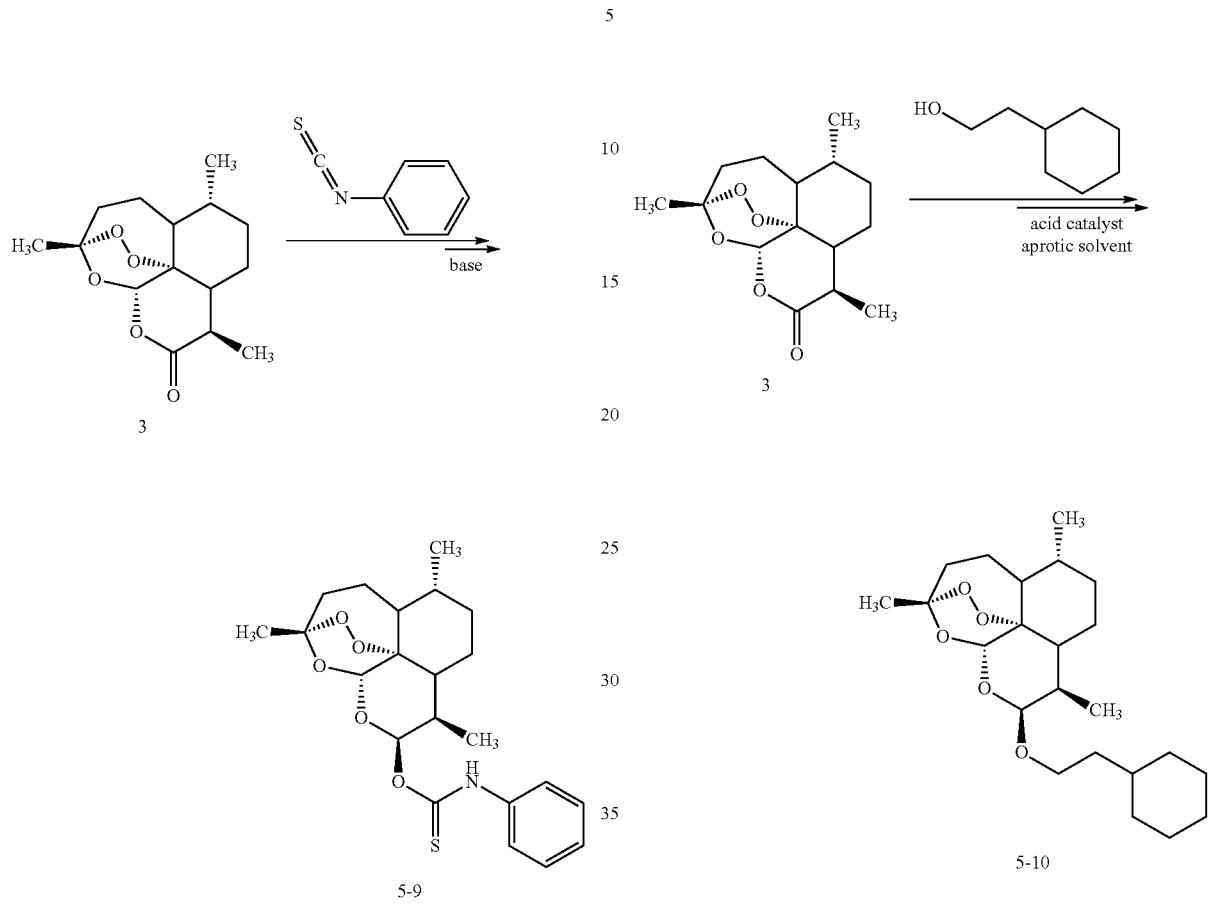

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.344 mL benzyl isothiocyanate, 1.8 mL triethylamine in 7 mL dichloromethane) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NH_4Cl$. The organic phase was dried down yielding an off-white solid. Purification was achieved by column chromatography over silica gel (5%-20% EtOAc, in cyclohexane) providing pure Artemisinin derivative 5-9 as white solid.

mass spec: $C_{22}H_{29}NO_5S$; 420.1733 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.363 mL 2-cyclohexylethanol, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure Artemisinin derivative 5-10 as white solid. mass spec: $C_{23}H_{38}O_5$; 395.2704 [M+H$^+$].

Example 7-17. Synthesis of Artemisinin Ether Derivative (5-11) from Artemisinin (3)

Example 7-18. Synthesis of Artemisinin Ether Derivative (5-12) from Artemisinin (3)

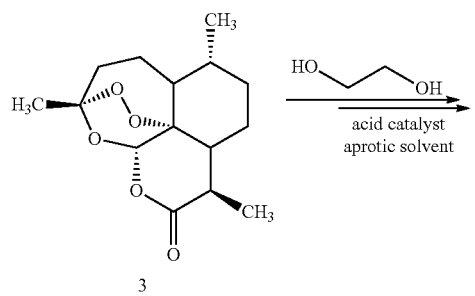

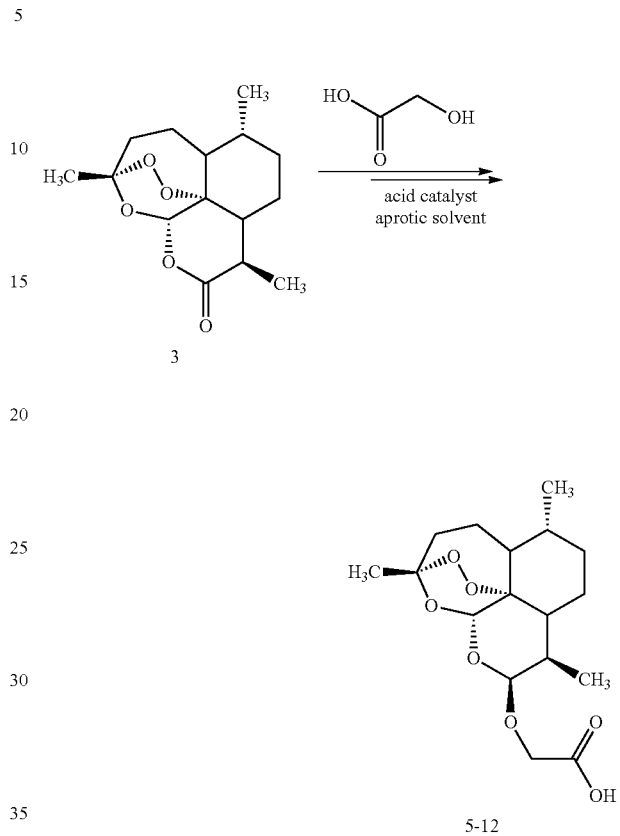

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.145 mL, ethylene glycol, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure Artemisinin derivative 5-11 as white solid.

mass spec: C$_{17}$H$_{28}$O$_6$; 329.1896 [M+H]$^+$.

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (198 mg glycolic acid, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure Artemisinin derivative 5-12 as white solid.

mass spec: C$_{17}$H$_{26}$O$_7$; 343.1663 [M+H]$^+$.

Example 7-19. Synthesis of Artemisinin Ether Derivative (5-13) from Artemisinin (3)

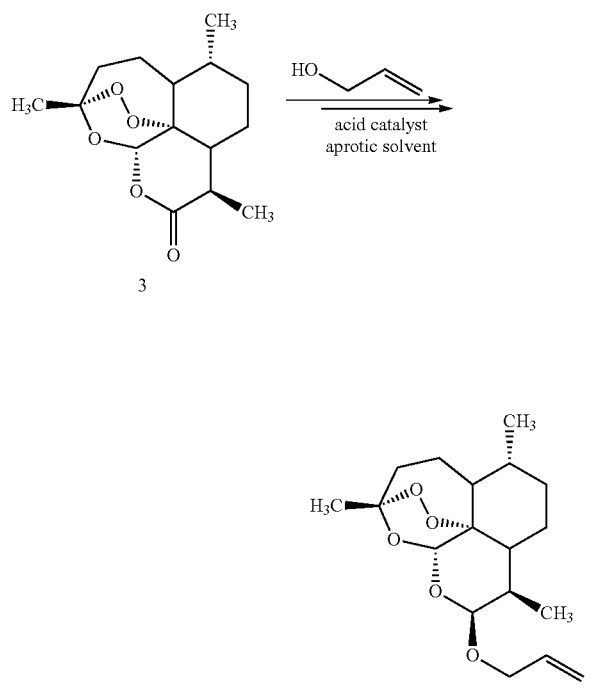

Example 7-20. Synthesis of Artemisinin Ether Derivative (5-14) from Artemisinin (3)

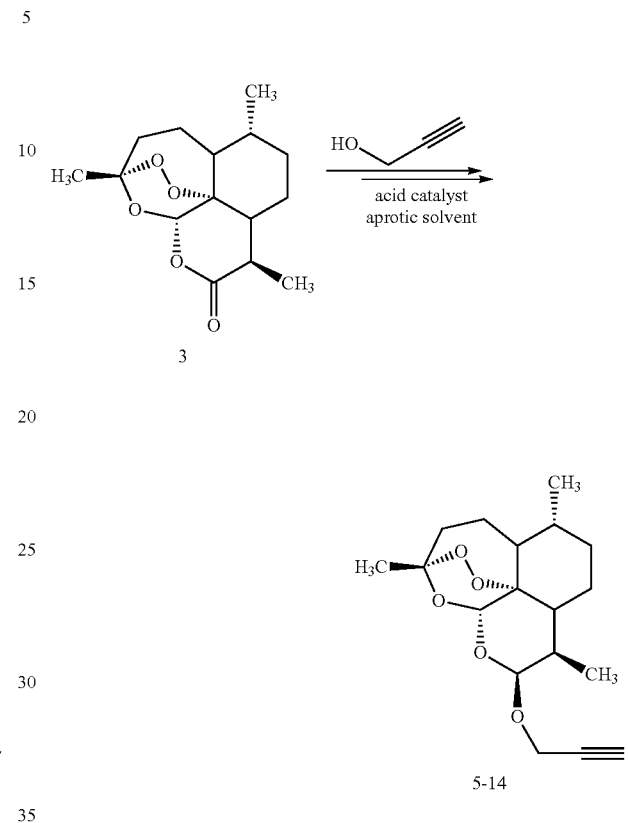

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (0.177 mL allyl alcohol, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure Artemisinin derivative 5-13 as white solid.

mass spec: $C_{18}H_{28}O_5$; 325.1922 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution (0.151 mL propargyl alcohol, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure Artemisinin derivative 5-14 as white solid.

mass spec: $C_{18}H_{26}O_5$; 323.1767 [M+H$^+$].

Example 7-21. Synthesis of Artemisinin Thioether Derivative (5-15) from Artemisinin (3)

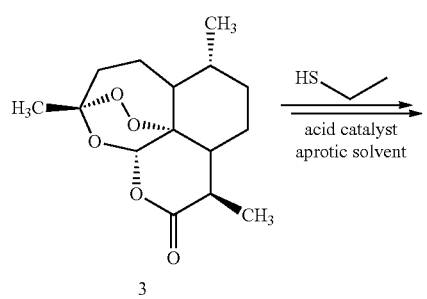

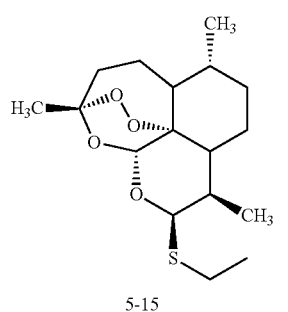

5-15

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (0.192 mL ethanethiol, 0.45 mL conc. HCl in 2 mL THF) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure Artemisinin derivative 5-15 as white solid.

mass spec: C$_{17}$H$_{28}$O$_4$S; 329.1701 [M+H$^+$].

Example 7-22. Synthesis of Artemisinin Derivative (5-16) from Artemisinin (3) by Using the Inventive Continuous Flow Reactor with One Column (FIG. 6)

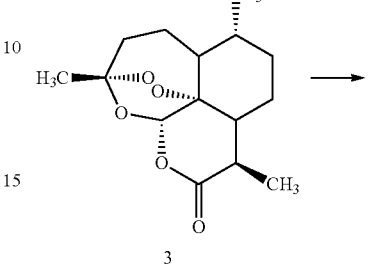

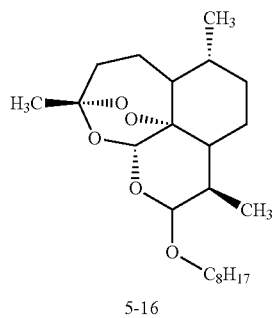

5-16

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 1-octanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure artemisinin derivative 5-16 as white solid.

mass spec: C$_{23}$H$_{40}$O$_5$; 397.2861 [M+H$^+$].

Example 7-23. Synthesis of Artemisinin Derivative (5-17) from Artemisinin (3) by Using the Inventive Continuous Flow Reactor with One Column (FIG. 6)

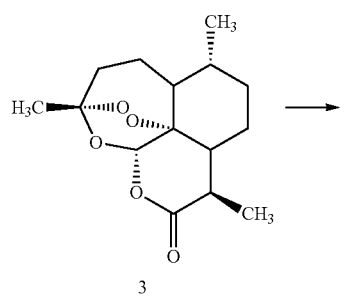

3

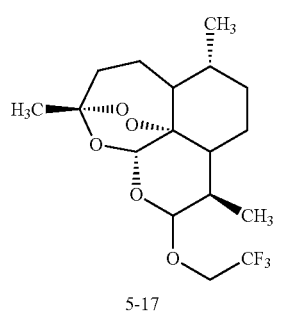

5-17

Example 7-24. Synthesis of Artemisinin Derivative (5-18) from Artemisinin (3) by Using the Inventive Continuous Flow Reactor with One Column (FIG. 6)

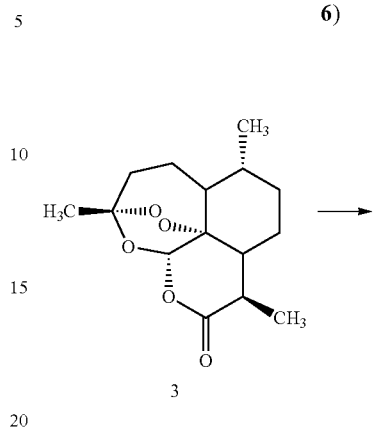

3

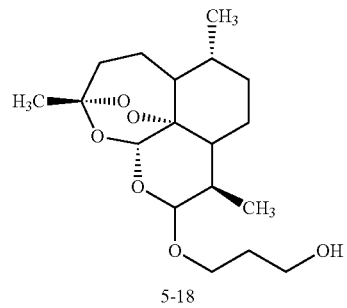

5-18

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 2,2,2-trifluoroethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-17 as white solid. mass spec: $C_{17}H_{25}F_3O_5$; 367.1637 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 1,3-propanediol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-18 as white solid.

mass spec: $C_{18}H_{30}O_6$; 343.2017 [M+H$^+$].

Example 7-25. Synthesis of Artemisinin Derivative (5-19) from Artemisinin (3) by Using the Inventive Continuous Flow Reactor with One Column (FIG. 6)

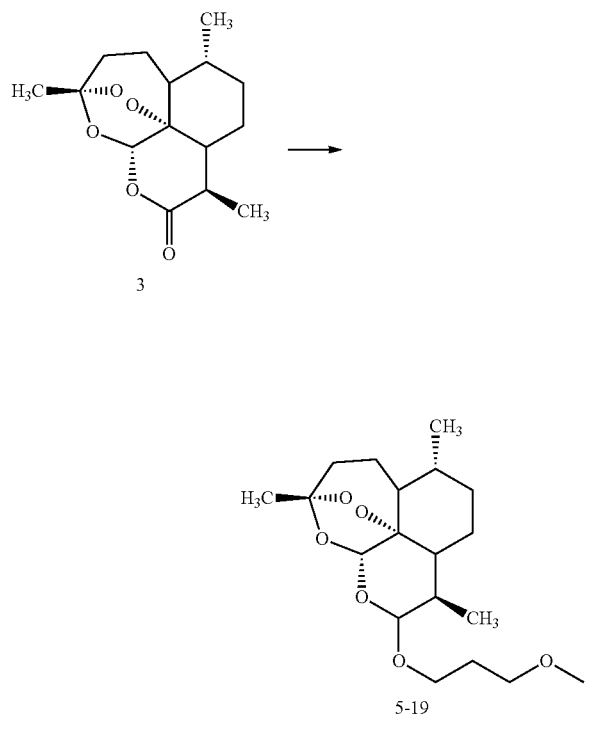

Example 7-26. Synthesis of Artemisinin Derivative (5-20) from Artemisinin (3) by Using the Inventive Continuous Flow Reactor with One Column (FIG. 6)

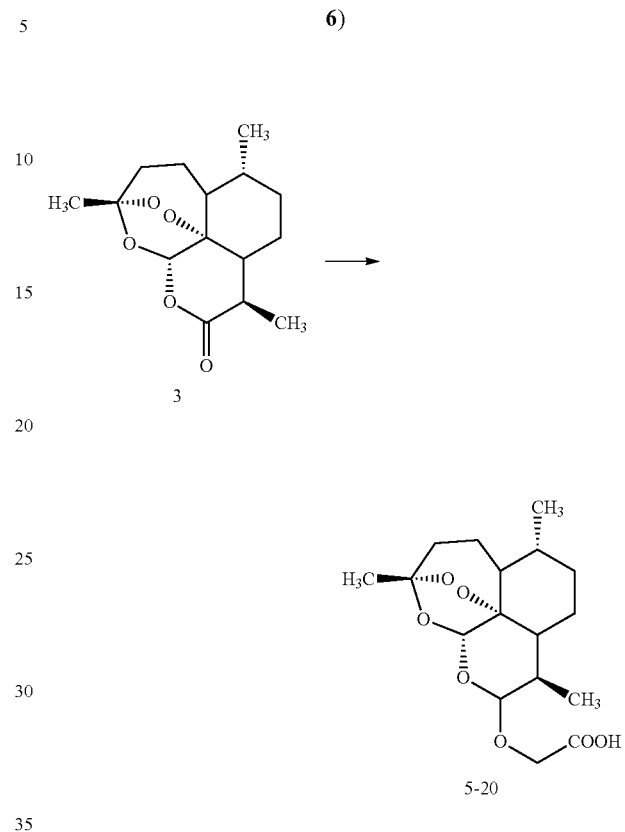

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 3-methoxy-1-propanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-19 as white solid.

mass spec: $C_{19}H_{32}O_6$; 357.2185 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (500 mg glycolic acid, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-20 as white solid.

mass spec: $C_{17}H_{26}O_7$; 343.1661 [M+H$^+$].

Example 7-27. Synthesis of Artemisinin Derivative (5-21) from Artemisinin (3) by Using the Inventive Continuous Flow Reactor with One Column (FIG. 6)

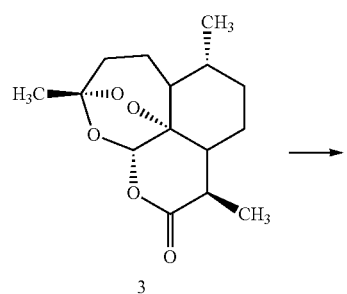

3

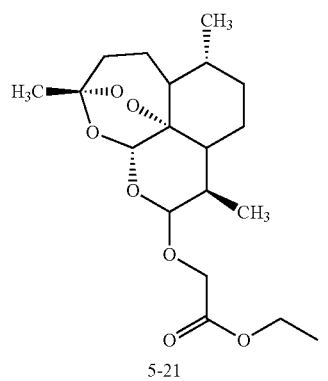

5-21

Example 7-28. Synthesis of Artemisinin Derivative (5-22) from Artemisinin (3) by Using the Inventive Continuous Flow Reactor with One Column (FIG. 6)

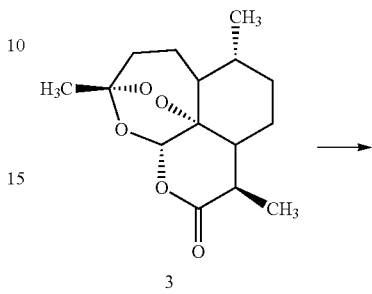

3

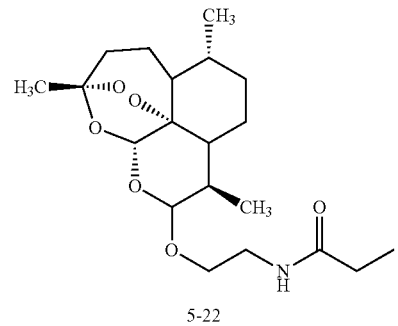

5-22

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water. The organic phase pumped at a flow rate of 0.5 mL/min. Reagent solution B (1 mL ethyl glycolate, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-21 as white solid. mass spec: $C_{19}H_{30}O_7$; 371.19915 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (500 mg N-(2-hydroxyethyl)propanamide, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-22 as white solid. mass spec: $C_{20}H_{33}NO_6$; 384.2287 [M+H$^+$].

Example 7-29. Synthesis of Artemisinin Derivative (5-23) from Artemisinin (3) by Using the Inventive Continuous Flow Reactor with One Column (FIG. 6)

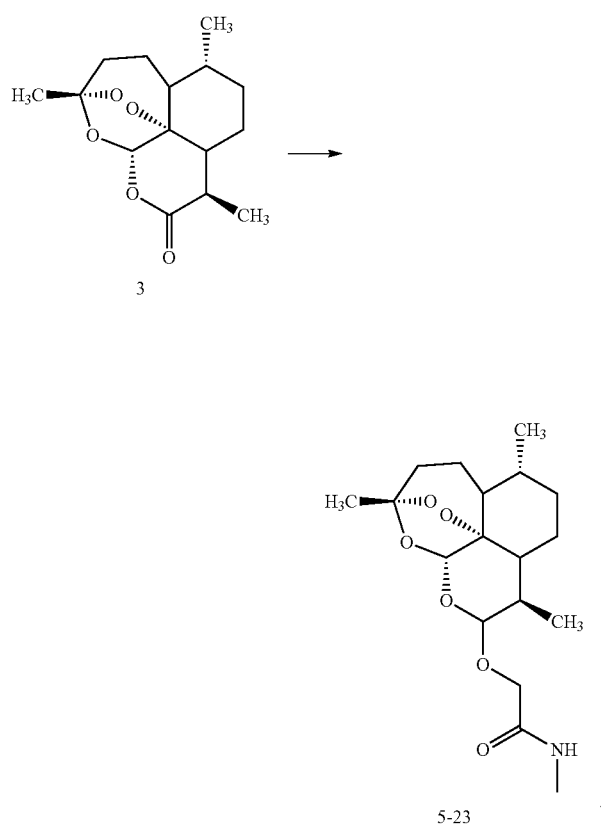

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (100 mg 2-hydroxy-N-methylacetamide, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-23 as white solid.

mass spec: $C_{18}H_{29}NO_6$; 356.1977 [M+H$^+$].

Example 7-30. Synthesis of Artemisinin Derivative (5-24) from Artemisinin (3) by Using the Inventive Continuous Flow Reactor with One Column (FIG. 6)

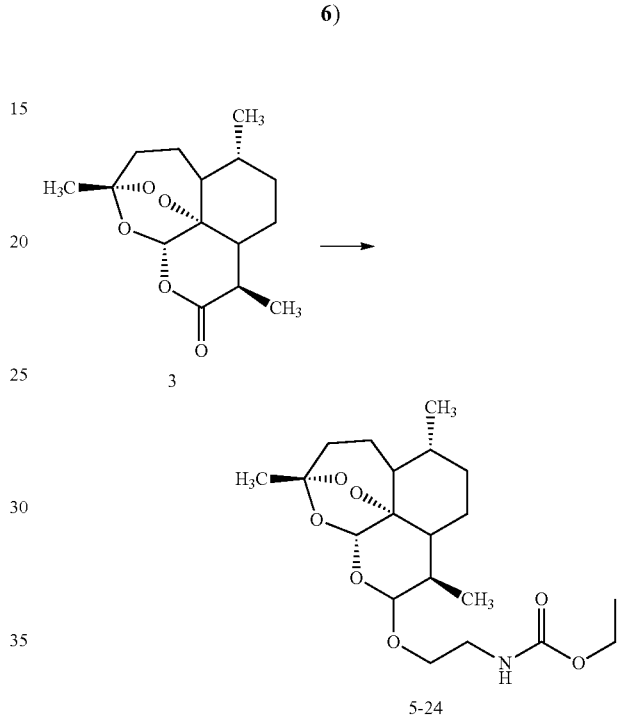

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (100 mg ethyl N-(2-hydroxyethyl)-carbamate, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-24 as white solid.

mass spec: $C_{20}H_{33}NO_7$; 400.2264 [M+H$^+$].

Example 7-31. Synthesis of Artemisinin Derivative (5-25) from Artemisinin (3) by Using the Inventive Continuous Flow Reactor with One Column (FIG. 6)

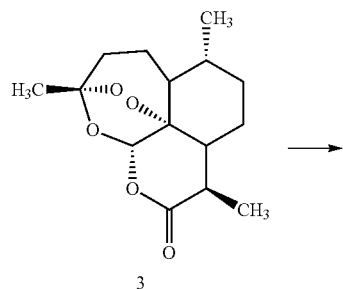

3

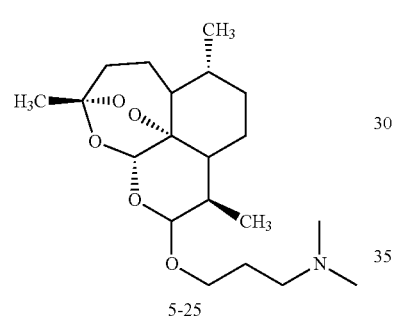

5-25

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 ml 3-dimethylamino-1-propanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-25 as white solid.

mass spec: $C_{20}H_{35}NO_5$; 370.2496 [M+H$^+$].

Example 7-32. Synthesis of Artemisinin Derivative (5-26) from Artemisinin (3) by Using the Inventive Continuous Flow Reactor with One Column (FIG. 6)

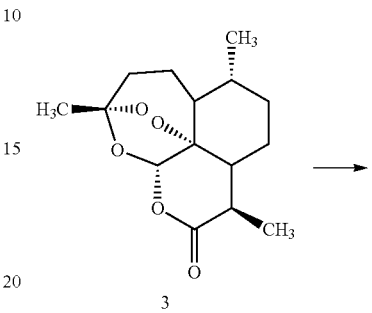

3

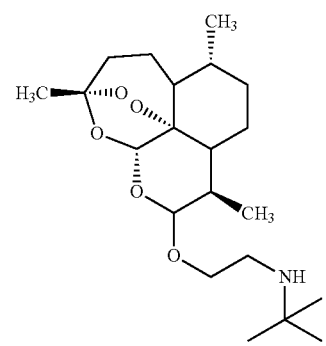

5-26

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 2-(tert-butylamino)ethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-26 as white solid. mass spec: $C_{21}H_{37}NO_5$; 384.2656 [M+H$^+$].

Example 7-33. Synthesis of Artemisinin Derivative (5-27) from Artemisinin (3) by Using the Inventive Continuous Flow Reactor with One Column (FIG. 6)

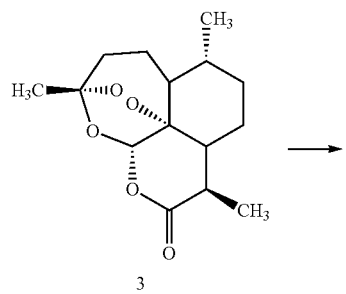

3

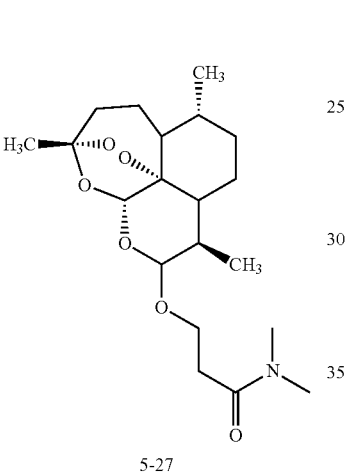

5-27

Example 7-34. Synthesis of Artemisinin Derivative (5-28) from Artemisinin (3) by Using the Inventive Continuous Flow Reactor with One Column (FIG. 6)

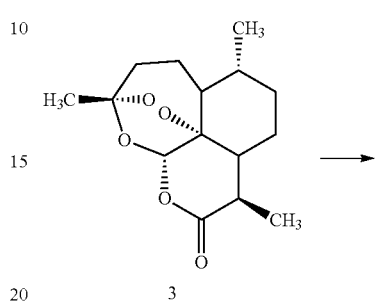

3

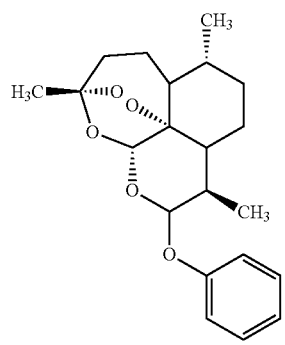

5-28

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (100 mg 3-hydroxy-N,N-dimethylpropanamide, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-27 as white solid. mass spec: $C_{20}H_{33}NO_6$; 384.2288 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL phenol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-28 as white solid.

mass spec: $C_{21}H_{28}O_5$; 361.1926 [M+H+].

Example 7-35. Synthesis of Artemisinin Derivative (5-29) from Artemisinin (3) by Using the Inventive Continuous Flow Reactor with One Column (FIG. 6)

Example 7-36. Synthesis of Artemisinin Derivative (5-30) from Artemisinin (3) by Using the Inventive Continuous Flow Reactor with One Column (FIG. 6)

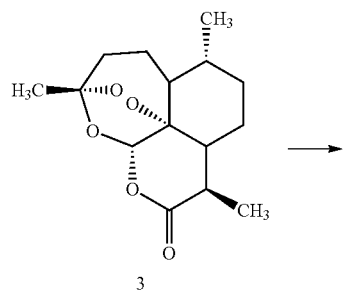

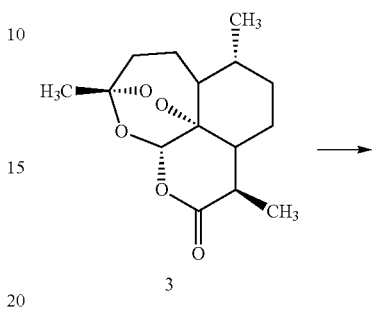

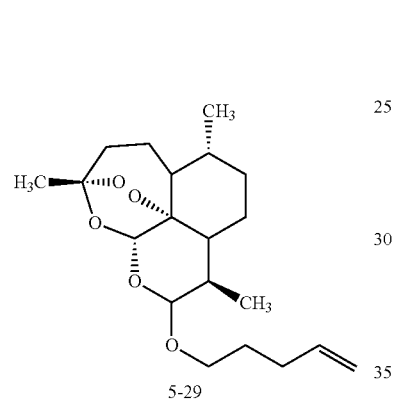

5-29

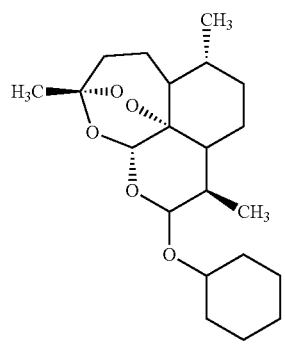

5-30

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 4-penten-1-ol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) ¹⁄₁₆ in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-29 as white solid.

mass spec: $C_{20}H_{32}O_5$; 353.2243 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL cyclohexanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) ¹⁄₁₆ in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-30 as white solid.

mass spec: $C_{21}H_{34}O_5$; 367.2392 [M+H$^+$].

Example 7-37. Synthesis of Artemisinin Derivative (5-31) from Artemisinin (3) by Using the Inventive Continuous Flow Reactor with One Column (FIG. 6)

Example 7-38. Synthesis of Artemisinin Derivative (5-32) from Artemisinin (3) by Using the Inventive Continuous Flow Reactor with One Column (FIG. 6)

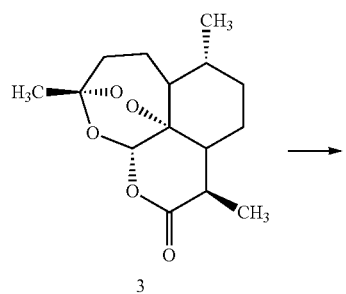
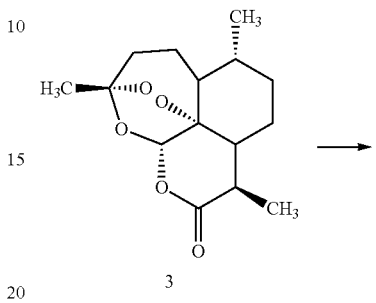
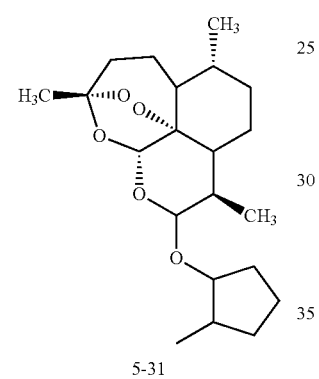
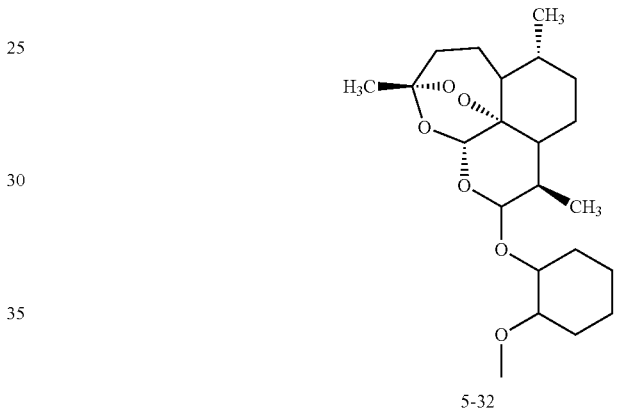

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 2-methylcyclopentanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-31 as white solid.

mass spec: $C_{21}H_{34}O_5$; 367.2387 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (1 mL 2-methoxycyclohexanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-32 as white solid.

mass spec: $C_{22}H_{36}O_6$; 397.2495 [M+H$^+$].

Example 7-39. Synthesis of Artemisinin Derivative (5-33) from Artemisinin (3) by Using the Inventive Continuous Flow Reactor with One Column (FIG. 6)

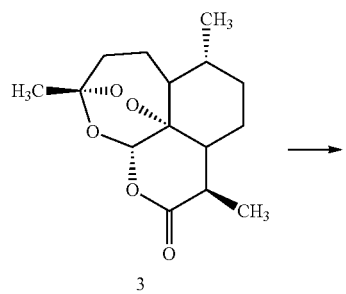

3

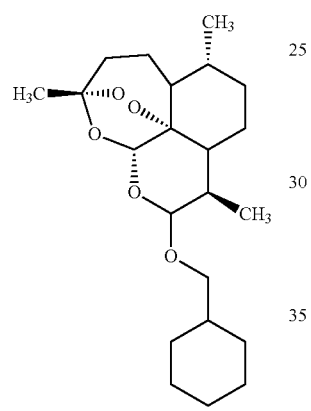

5-33

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL cyclohexanemethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure artemisinin derivative 5-33 as white solid. mass spec: C$_{22}$H$_{36}$O$_5$; 381.2544 [M+H$^+$].

Example 7-40. Synthesis of Artemisinin Derivative (5-34) from Artemisinin (3) by Using the Inventive Continuous Flow Reactor with One Column (FIG. 6)

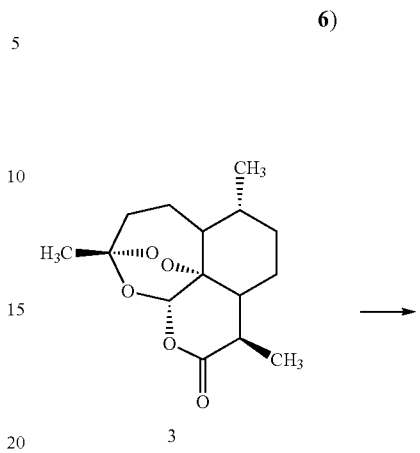

3

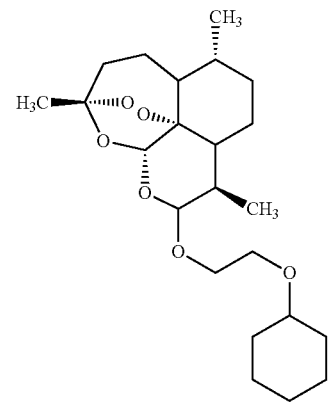

5-34

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 2-(cyclohexyloxy)ethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure artemisinin derivative 5-34 as white solid.

mass spec: C$_{23}$H$_{38}$O$_6$; 411.2645 [M+H$^+$].

Example 7-27. Synthesis of Artemisinin Derivative (5-35) from Artemisinin (3) by Using the Inventive Continuous Flow Reactor with One Column (FIG. 6)

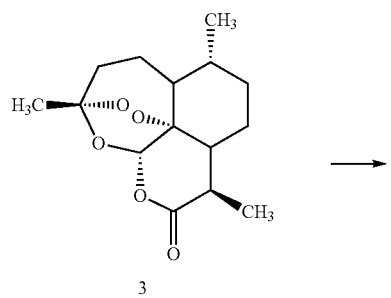

3

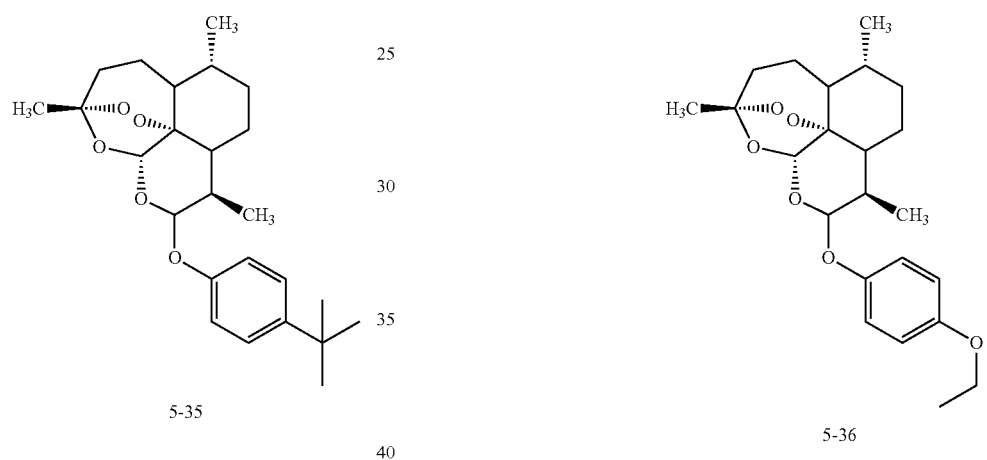

5-35

Example 7-41. Synthesis of Artemisinin Derivative (5-36) from Artemisinin (3) by Using the Inventive Continuous Flow Reactor with One Column (FIG. 6)

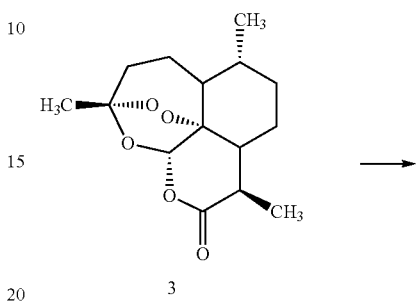

3

5-36

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL tert-butylphenol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-35 as white solid.

mass spec: $C_{25}H_{36}O_5$; 417.2540 $[M+H^+]$.

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 4-ethoxyphenol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-36 as white solid.

mass spec: $C_{23}H_{32}O_6$; 405.2182 $[M+H^+]$.

Example 7-42. Synthesis of Artemisinin Derivative (5-37) from Artemisinin (3) by Using the Inventive Continuous Flow Reactor with One Column (FIG. 6)

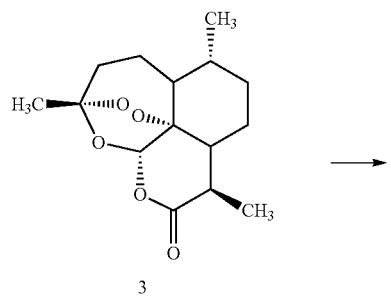

3

Example 7-43. Synthesis of Artemisinin Derivative (5-38) from Artemisinin (3) by Using the Inventive Continuous Flow Reactor with One Column (FIG. 6)

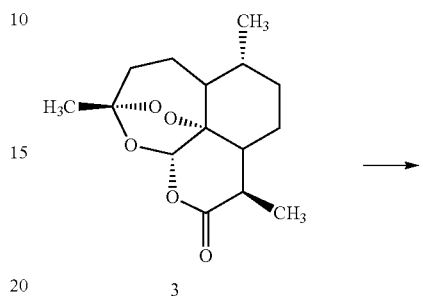

3

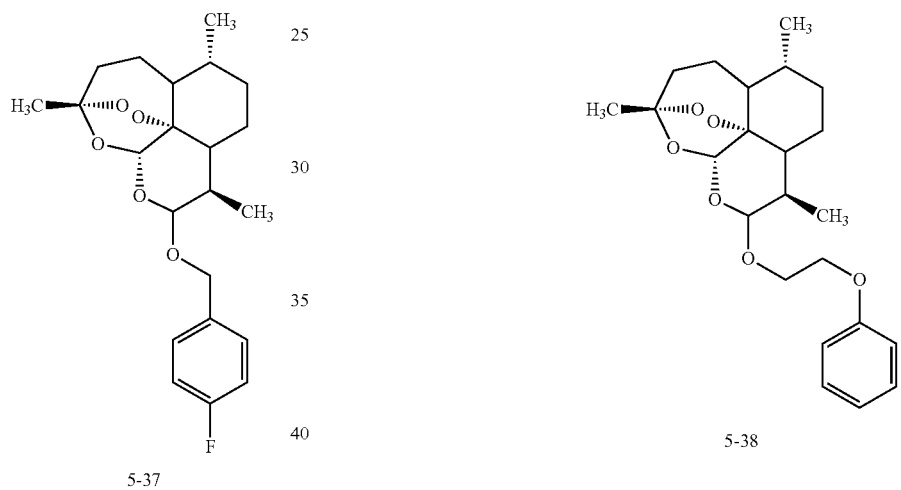

5-37

5-38

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (100 mg 4-fluorobenzyl alcohol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure artemisinin derivative 5-37 as white solid. mass spec: C$_{22}$H$_{29}$FO$_5$; 393.1985 [M+H$^+$].

To the crude solution of Artemisinin (2.7 mL), prepared as described in Example 4, was added 0.37 mL of ethanol. This was passed through a 2.2 mL column (prepared by mixing 650 mg Celite and 650 mg Li$_2$CO$_3$, 650 mg NaBH$_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2 mL 2-phenoxyethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous NaHCO$_3$. The organic phase was dried down yielding an off-white solid. Purification was achieved by column chromatography over silica gel (5%-20% EtOAc, in cyclohexane) providing pure artemisinin derivative 5-38 as white solid.

mass spec: C$_{23}$H$_{32}$O$_6$; 405.2177 [M+H$^+$].

Example 7-44. Synthesis of Artemisinin Derivative (5-39) from Artemisinin (3) by Using the Inventive Continuous Flow Reactor with One Column (FIG. 6)

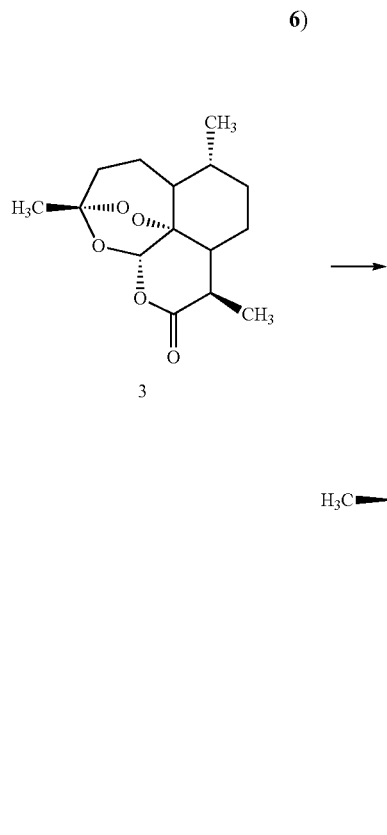

3

5-39

To the crude solution of Artemisinin (2.7 mL), prepared as described in Example 4, was added 0.37 mL of ethanol. This was passed through a 2.2 mL column (prepared by mixing 650 mg Celite and 650 mg $Li_2CO_3$, 650 mg $NaBH_4$, and 520 mg LiCl together and packing into a 6.6 mm×150 mm Omnifit column with a 1 cm cotton plug at the outlet end. The material was packed by tapping on the bench top) at a flow rate of 0.2 mL/min using THF as eluent and collected over water.

The organic phase pumped at a flow rate of 0.5 mL/min. Reagent solution B (2-furylmethanol, 1 mL trimethylorthoformate, 0.45 mL conc. HCl) was mixed in at a flow rate of 0.5 mL/min and the mixture introduced into reactor 12, consisting of 20 mL tubing (IDEX Health & Science, fluorinated ethylene polymer 1520, natural color, outside diameter (OD) 1/16 in and inside diameter (ID) 0.030 in). After exiting the reactor the solution was collected over saturated aqueous $NaHCO_3$. The organic phase was dried down yielding an off-white solid. Purification was achieved by column chromatography over silica gel (5%-20% EtOAc, in cyclohexane) providing pure artemisinin derivative 5-39 as white solid.

mass spec: $C_{20}H_{28}O_6$; 365.1879 [M+H$^+$].

The invention claimed is:

1. A method for reducing artemisinin in a continuous manner comprising:

1) providing a column containing a hydride reducing agent, at least one activator and at least one solid base or providing a first column containing at least one solid base and a second column containing a hydride reducing agent and at least one activator, 2) providing a continuous flow of a solution of artemisinin in at least one aprotic solvent containing at least one $C_1$-$C_5$ alcohol through the column containing the hydride reducing agent, the at least one activator and the at least one solid base or through the first column containing the at least one solid base and the second column containing the hydride reducing agent and the at least one activator, 3) thereby reducing artemisinin in a continuous manner to dihydroartemisinin of the following formula

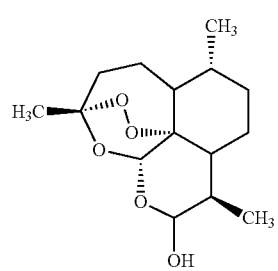

4 wherein the hydride reducing agent is selected from the group consisting of sodium borohydride, lithium borohydride, potassium borohydride, calcium borohydride, Superhydride® (a solution of lithium triethylborohydride), L/K/N-Selectrides (lithium/potassium/sodium tri(sec-butyl) borohdyride), LiAlH(OtBu)$_3$, RedAl, DIBAL-H, Titanocene and a mixture thereof;

the at least one activator is selected from the group consisting of alkaline metal halides, alkaline earth metal halides, In salts, $I_2$, Ni salts, Ni foam, hydrogels containing Co and/or Ni nanoparticles, nanotubes containing Au nanoparticles, Pb salts, $TiO_2$ containing Pd or Co—Ni—P, polyaniline salts, propanephosphonic acid cyclic anhydride, protein-capped Au nanoparticles, pyridinium based dicationic ionic salts, Ru salts, Ru immobilized on $Al_2O_3$ pellets, Ru-activated carbon, CeCl$_3$, Ru—CeO$_2$, Ru—TiO$_2$, Ru-γ Al$_2$O$_3$, Ru$_{60}$Co$_{20}$Fe$_{20}$, Ru-promoted sulphated zirconia, titanyl acetylacetonate, Au nanoparticles, Co salts, Celite® Amberlyst 15, Amberlyst 15 with dextrose or galactose and phloroglucinol;

the at least one solid base is selected from the group consisting of: metal hydroxides, metal carbonates, ammonium hydroxide, and tetraalkylammonium hydroxides; and the at least one $C_1$-$C_5$ alcohol is selected from the group consisting of: $CH_3OH$, $CH_3CH_2OH$, $CH_3CH_2CH_2OH$, $CH_3CH_2CH_2CH_2OH$, $CH(CH_3)_2CH_2OH$, $CH_3CH_2CH_2CH_2CH_2OH$, $HOCH_2CH_2OH$, $HOCH_2CH_2CH_2OH$, $HOCH_2CH_2CH_2CH_2OH$, $HOCH_2CH_2CH_2CH_2CH_2OH$, $HOCH_2CH(OH)CH_2OH$, $HOCH_2CH(OH)CH_2CH_2OH$, $HOCH_2CH(OH)CH(OH)CH_3$, $HOCH_2CH(OH)CH(OH)CH_2OH$, $HOCH_2CH(OH)CH_2CH_2CH_2OH$, $HOCH_2CH_2CH(OH)CH_2CH_2OH$, $HOCH_2CH(OH)CH(OH)$ $CH_2CH_2OH$, $HOCH_2CH(OH)CH_2CH(OH)CH_2OH$, $HOCH_2CH(OH)CH(OH)CH(OH)CH_2OH$, $HC(CH_2OH)_3$, $HO-C(CH_2OH)_3$, and $C(CH_2OH)_4$.

2. The method according to claim 1 comprising:
1) providing a column containing a hydride reducing agent, at least one activator and at least one solid base,
2) providing a continuous flow of a solution of artemisinin in at least one aprotic solvent containing at least one $C_1$-$C_5$ alcohol through the column containing the hydride reducing agent, the at least one activator and the at least one solid base,
3) thereby reducing artemisinin in a continuous manner to dihydroartemisinin of the following formula

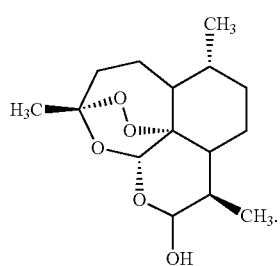

4

3. The method according to claim 1 further comprising A) and B) before step 1):
A) providing dihydroartemisinic acid represented by the following formula

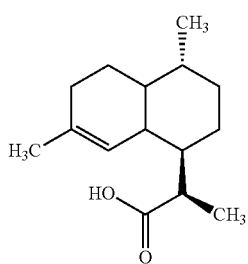

2

B) performing the following reactions
i) photooxidation of dihydroartemisinic acid with singlet oxygen,
ii) followed by an acid mediated cleavage, and
iii) subsequent oxidation with triplet oxygen
in order to obtain artemisinin of the following formula:

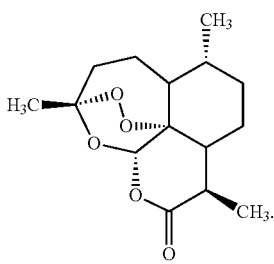

3

4. The method according to claim 1 further comprising 4) after the step 3):

4) converting the dihydroartemisinin obtained from step 3) to an artemisinin derivative of the following formula

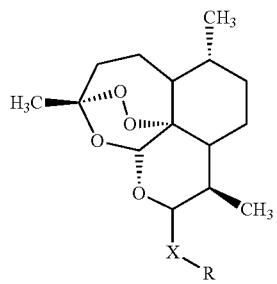

5 wherein X is O or S;
R is —$R^1$, —$COR^1$, —$CONHR^1$, —$CSNHR^1$, or —$SO_2R^1$; and
$R^1$ represents a $C_1$-$C_{10}$ alkyl, $C_1$-$C_{10}$ halogenalkyl, $C_1$-$C_{10}$ hydroxyalkyl, $C_2$-$C_{10}$ alkoxyalkyl, $C_2$-$C_{10}$ carboxyalkyl, $C_6$-$C_{14}$ aryl, $C_7$-$C_{16}$ alkylaryl, $C_7$-$C_{16}$ alkoxyaryl, $C_7$-$C_{16}$ arylalkyl, $C_8$-$C_{16}$ arylalkoxyalkyl, $C_8$-$C_{16}$ alkylarylalkyl, $C_8$-$C_{16}$ alkylarylalkoxyalkyl, $C_2$-$C_{10}$ alkenyl, $C_2$-$C_{10}$ alkynyl, $C_3$-$C_8$ cycloalkyl, $C_4$-$C_{10}$ alkylcycloalkyl, $C_4$-$C_{10}$ alkoxyalkylcycloalkyl, $C_4$-$C_{12}$ cycloalkylalkyl, $C_4$-$C_{16}$ cycloalkylalkoxyalkyl, $C_1$-$C_5$ heterocyclyl, $C_3$-$C_{10}$ alkoxycarbonylalkyl, $C_2$-$C_{10}$ acyloxyalkyl, $C_3$-$C_{12}$ heterocyclylalkyl, $C_3$-$C_{10}$ alkylcarbonylaminoalkyl, $C_3$-$C_{10}$ alkoxycarbonylaminoalkyl, $C_1$-$C_{10}$ aminoalkyl, $C_2$-$C_{10}$ alkylaminoalkyl, $C_3$-$C_{10}$ dialkylaminoalkyl, $C_3$-$C_{10}$ alkylaminocarbonylalkyl, or $C_4$-$C_{10}$ dialkylaminocarbonylalkyl.

5. The method according to claim 4, wherein converting the dihydroartemisinin 4 to the artemisinin derivative of the formula (5) is performed by reacting the dihydroartemisinin 4 with a precursor compound and
if R is —$R^1$, then the precursor compound is $R^1$—X—H or $R^1$-$L_1$;
if R is —$COR^1$ and $R^1$ is not $C_2$-$C_{10}$ carboxylalkyl, then the precursor compound is $R^1$—$CO_2H$, or $R^1$—CO—O—OC—$R^1$;
if R is —$COR^1$ and $R^1$ is $C_2$-$C_{10}$ carboxylalkyl, then the precursor compound is $C_3$-$C_{11}$ cyclic anhydride of the formula

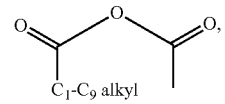

or $C_3$-$C_{11}$ alkyl carboxylic acid $C_1$-$C_4$ alkyl ester;
if R is —$CONHR^1$, then the precursor compound is $R^1$—N=C=O;
if R is —$CSNHR^1$, then the precursor compound is $R^1$—N=C=S;
if R is —$SO_2R^1$, then the precursor compound is $R^1SO_3H$, $R^1SO_2Cl$, or $R^1SO_2$—O—$SO_2R^1$;
wherein $R^1$ has the same meaning as defined in claim 4;
$L_1$ is a leaving group selected from the group consisting of —F, —Cl, —Br, —I, —$OSO_2Me$, —$OSO_3Me$, —$OSO_2CF_3$, —$OSO_2CF_2CF_3$, and —$OSO_2$(p-Tol).

6. The method according to claim 1, wherein the molar ratio of artemisinin to hydride reducing agent is in the range of 1.0:1.0 to 1.0:2.0.

7. The method according to claim 1, wherein the activator is selected from a group consisting of LiF, LiCl, LiBr, LiI, $CaCl_2$, $InCl_3$, $Ni(bpy)Cl_2$, $PbF_2$, $PbCl_2$, $PbBr_2$, $PbI_2$, $RuCl_3$, $Ru(NO)(NO_3)_3$, $CoCl_2$ and a mixture thereof.

8. The method according to claim 1, wherein the at least one $C_1$-$C_5$ alcohol is selected from the group consisting of $CH_3OH$, $CH_3CH_2OH$, $CH_3CH_2CH_2OH$, $HOCH_2CH_2OH$, $HOCH_2CH_2CH_2OH$, $HC(CH_2OH)_3$, $HO$—$C(CH_2OH)_3$, and $C(CH_2OH)_4$.

9. The method according to claim 1, wherein the solid base is selected from a group consisting of $Li_2CO_3$, $Na_2CO_3$, $K_2CO_3$, $CaCO_3$, $MgCO_3$, LiOH, NaOH, KOH, $Ca(OH)_2$, $Mg(OH)_2$, and mixtures thereof.

10. The method according to claim 1, wherein the solid base and/or the activator and the hydride reducing agent are mixed with a filler material.

11. A continuous flow reactor configured and adapted to the continuous production and reduction of artemisinin comprising:
a photochemical reactor configured and adapted to performing the photooxidation of dihydroartemisinic acid with singlet oxygen in a continuous manner,
a reactor configured and adapted to performing an acid mediated cleavage of the photooxidation product and the subsequent oxidation with triplet oxygen in order to obtain artemisinin,
a column containing a hydride reducing agent, at least one activator and at least one solid base or a first column containing at least one solid base and a second column containing a hydride reducing agent and at least one activator, said columns are configured and adapted to reduce artemisinin to dihydroartemisinin;
wherein
the hydride reducing agent is selected from the group consisting of: sodium borohydride, lithium borohydride, potassium borohydride, calcium borohydride, Superhydride® (a solution of lithium triethylborohydride), L/K/N-Selectrides (lithium/potassium/sodium tri(sec-butyl) borohdyride), $LiAlH(OtBu)_3$, RedAl, DIBAL-H, Titanocene and a mixture thereof;
the at least one activator is selected from the group consisting of: alkaline metal halides, alkaline earth metal halides, In salts, $I_2$, Ni salts, Ni foam, hydrogels containing Co and/or Ni nanoparticles, nanotubes containing Au nanoparticles, Pb salts, $TiO_2$ containing Pd or Co—Ni—P, polyaniline salts, propanephosphonic acid cyclic anhydride, protein-capped Au nanoparticles, pyridinium based dicationic ionic salts, Ru salts, Ru immobilized on $Al_2O_3$ pellets, Ru-activated carbon, $CeCl_3$, Ru—$CeO_2$, Ru—$TiO_2$, Ru-γ $Al_2O_3$, $Ru_{60}Co_{20}Fe_{20}$, Ru-promoted sulphated zirconia, titanyl acetylacetonate, Au nanoparticles, Co salts, Celite® Amberlyst 15, Amberlyst 15 with dextrose or galactose and phloroglucinol; and
the at least one solid base is selected from the group consisting of: metal hydroxides, metal carbonates, ammonium hydroxide, and tetraalkylammonium hydroxides.

12. The continuous flow reactor according to claim 11 further comprising:
a reactor configured and adapted to converting dihydroartemisinin to the artemisinin derivative of the following formula

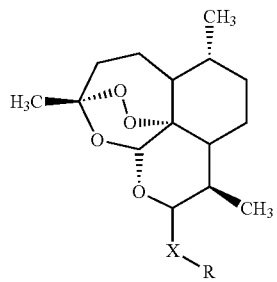

wherein X is O or S;

R is —$R^1$, —$COR^1$, —$CONHR^1$, —$CSNHR^1$, or —$SO_2R^1$; and $R^1$ represents a $C_1$-$C_{10}$ alkyl, $C_1$-$C_{10}$ halogenalkyl, $C_1$-$C_{10}$ hydroxyalkyl, $C_2$-$C_{10}$ alkoxyalkyl, $C_2$-$C_{10}$ carboxyalkyl, $C_6$-$C_{14}$ aryl, $C_7$-$C_{16}$ alkylaryl, $C_7$-$C_{16}$ alkoxyaryl, $C_7$-$C_{16}$ arylalkyl, $C_8$-$C_{16}$ arylalkoxyalkyl, $C_8$-$C_{16}$ alkylarylalkyl, $C_8$-$C_{16}$ alkylarylalkoxyalkyl, $C_2$-$C_{10}$ alkenyl, $C_2$-$C_{10}$ alkynyl, $C_3$-$C_8$ cycloalkyl, $C_4$-$C_{10}$ alkylcycloalkyl, $C_4$-$C_{10}$ alkoxyalkylcycloalkyl, $C_4$-$C_{12}$ cycloalkylalkyl, $C_4$-$C_{16}$ cycloalkylalkoxyalkyl, $C_1$-$C_5$ heterocyclyl, $C_3$-$C_{10}$ alkoxycarbonylalkyl, $C_2$-$C_{10}$ acyloxyalkyl, $C_3$-$C_{12}$ heterocyclylalkyl, $C_3$-$C_{10}$ alkylcarbonylaminoalkyl, $C_3$-$C_{10}$ alkoxycarbonylaminoalkyl, $C_1$-$C_{10}$ aminoalkyl, $C_2$-$C_{10}$ alkylaminoalkyl, $C_3$-$C_{10}$ dialkylaminoalkyl, $C_3$-$C_{10}$ alkylaminocarbonylalkyl, or $C_4$-$C_{10}$ dialkylaminocarbonylalkyl.

13. The continuous flow reactor according to claim 11, wherein the activator is selected from a group consisting of LiF, LiCl, LiBr, LiI, $CaCl_2$, $InCl_3$, $Ni(bpy)Cl_2$, $PbF_2$, $PbCl_2$, $PbBr_2$, $PbI_2$, $RuCl_3$, $Ru(NO)(NO_3)_3$, $CoCl_2$ and a mixture thereof.

14. The continuous flow reactor according to claim 11, wherein the solid base is selected from a group consisting of $Li_2CO_3$, $Na_2CO_3$, $K_2CO_3$, $CaCO_3$, $MgCO_3$, LiOH, NaOH, KOH, $Ca(OH)_2$, $Mg(OH)_2$, and mixtures thereof.

15. The method according to claim 2 further comprising the following steps A) and B) before step 1):
A) providing dihydroartemisinic acid represented by the following formula

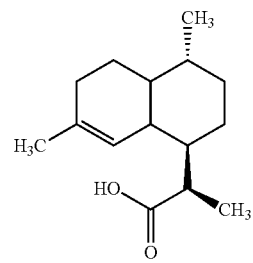

B) performing the following reactions
i) photooxidation of dihydroartemisinic acid with singlet oxygen, ii) followed by an acid mediated cleavage, and
iii) subsequent oxidation with triplet oxygen
and obtaining artemisinin of the following formula:

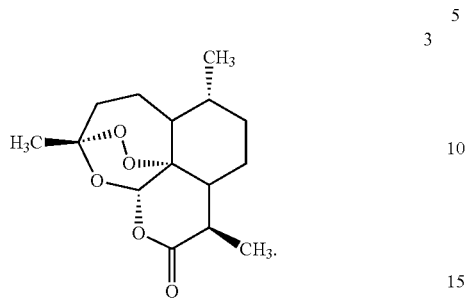

16. The method according to claim 1, wherein the activator is Li salts.

17. The method according to claim 1, wherein the metal hydroxides are alkaline metal hydroxides or alkaline earth metal hydroxides.

18. The continuous flow reactor according to claim 11, wherein the activator is Li salts.

19. The continuous flow reactor according to claim 11, wherein the metal hydroxides are alkaline metal hydroxides or alkaline earth metal hydroxides.

* * * * *